US009492497B2

(12) United States Patent
Zweytick et al.

(10) Patent No.: US 9,492,497 B2
(45) Date of Patent: Nov. 15, 2016

(54) PEPTIDES FOR THE TREATMENT OF CANCER

(71) Applicant: ÖSTERREICHISCHE AKADEMIE DER WISSENSCHAFTEN, Vienna (AT)

(72) Inventors: Dagmar Zweytick, Graz (AT); Karl Lohner, Graz (AT); Sabrina Riedl, Frauental an der Lassnitz (AT)

(73) Assignee: NEWFIELD THERAPEUTICS CORPORATION, Charlotte, NC (US)

( * ) Notice: Subject to any disclaimer, the term of this patent is extended or adjusted under 35 U.S.C. 154(b) by 0 days.

(21) Appl. No.: 14/760,445

(22) PCT Filed: Jan. 9, 2014

(86) PCT No.: PCT/EP2014/050330
§ 371 (c)(1),
(2) Date: Jul. 10, 2015

(87) PCT Pub. No.: WO2014/108475
PCT Pub. Date: Jul. 17, 2014

(65) Prior Publication Data
US 2016/0045562 A1    Feb. 18, 2016

(30) Foreign Application Priority Data
Jan. 11, 2013  (EP) .................................. 13150974

(51) Int. Cl.
A61K 38/10      (2006.01)
A61K 38/40      (2006.01)
C07K 14/79      (2006.01)
C07K 7/08       (2006.01)

(52) U.S. Cl.
CPC .............. *A61K 38/10* (2013.01); *A61K 38/40* (2013.01); *C07K 7/08* (2013.01); *C07K 14/79* (2013.01)

(58) Field of Classification Search
None
See application file for complete search history.

(56) References Cited

FOREIGN PATENT DOCUMENTS

WO    WO00/12542      3/2000
WO    WO2008/006125   1/2008
WO    WO2008/079030   7/2008

OTHER PUBLICATIONS

Gifford, J.L. et al.: "Lactoferricin: a lactoferrin-derived peptide with antimicrobial, antiviral, antitumor and immunological properties", Cellular and Molecular Life Sciences vol. 62, No. 22 (Nov. 2, 2005), pp. 2588-2598.

Eliassen, L.T. et al.: "Evidence for a Direct Antitumor Mechanism of Action of Bovine Lactoferricin", Anticancer Research, International Institute of Anticancer Research, vol. 22, No. 5, (2002), pp. 2703-2710.

Yoo, Y-C et al.: "Bovine Lactoferrin and Lactoferricin, a Peptide Derived From Bovine Lactoferrin, Inhibit Tumor Metastasis in Mice", Japanese Journal of Cancer Research, Japanese Cancer Association, Tokyo, JP, vol. 88, No. 2, (Feb. 1997), pp. 184-190.

Furlong, S.J. et al.: "Bovine lactoferricin induces caspase-independent apoptosis in human B-lymphoma cells and extends the survival of immune-deficient mice bearing B-lymphoma xenografts", Experimental and Molecular Pathology, vol. 88, No. 3, (Feb. 8, 2010), pp. 371-375.

Lizzi, A.R. et al.: "Lactoferrin Derived Peptides: Mechanisms of Action and their Perspectives as Antimicrobial and Antitumoral Agents", Mini-Reviews in Medicinal Chemistry. vol. 9, No. 6, (Jun. 2009), pp. 687-695.

Mader, J.S. et al.: "Cationic antimicrobial peptides as novel cytotoxic agents for cancer treatment", Expert Opinion on Investigational Drugs, vol. 15, No. 8, (Aug. 2006), pp. 933-946.

Yang, N. et al.: "The effects of shortening lactoferrin derived peptides against tumour cells, bacteria and normal human cells". Journal of Peptide Science, vol. 10, No. 1, (Jan. 16, 2004), pp. 37-46.

(Continued)

*Primary Examiner* — Christina Bradley
(74) *Attorney, Agent, or Firm* — Norton Rose Fulbright US LLP

(57) ABSTRACT

The present invention relates to an isolated peptide for use in the treatment of cancer consisting of 12 to 50 amino acid residues comprising—at least two beta-strands, or—at least two alpha-helices or—at least one beta-strand and at least one alpha-helix, —wherein said beta-strands and/or alpha-helices are preferably separated from each other by at least one turn, wherein the peptide has a net positive charge of +7 or more; —wherein said peptide comprises at least one peptide moiety having amino acid sequence $(X_1)_M$-$X_2$-$(X_3)_P$-$X_4$-$(X_5)_Q$-$X_6$-$(X_7)_S$ or the reverse sequence thereof, wherein $X_1$ is a hydrophobic amino acid, preferably selected from the group consisting of phenylalanine (Phe), alanine (Ala), leucine (Leu) and valine (Val), $X_2$ is a hydrophobic amino acid, preferably tryptophan (Trp), $X_3$ is selected from the group consisting of alanine (Ala), arginine (Arg), glutamine (Gln), asparagine (Asn), proline (Pro), isoleucine (Ile), leucine (Leu) and valine (Val), $X_4$ is selected from the group consisting of isoleucine (Ile), phenylalanine (Phe), tryptophan (Trp) and tyrosine (Tyr), $X_5$ is selected from the group consisting of arginine (Arg), lysine (Lys), tyrosine (Tyr) and phenylalanine (Phe), $X_6$ is a hydrophobic amino acid, preferably selected from the group consisting of isoleucine (Ile), tryptophan (Trp), valine (Val) and leucine (Leu), and $X_7$ is selected from the group consisting of arginine (Arg), lysine (Lys), isoleucine (Ile) and serine (Ser), and wherein M is 1 or 2, Q is 1 or 2, P is 2 or 3, and S is 1, 2, 3 or 4 under the proviso that if $(X_5)_Q$ is Arg-Arg S is 1; and wherein said peptide is devoid of intramolecular disulfide bonds.

2 Claims, 19 Drawing Sheets

(56) References Cited

OTHER PUBLICATIONS

Yang, N. et al.: "Enhanced Antitumor Activity and Selectivity of Lactoferrin-Derived Peptides", Journal of Peptide Research, vol. 60, No. 4, (Oct. 2002), pp. 187-197.
Yang, N. et al.: "Antitumour activity and specificity as a function of substitutions in the lipophilic sector of helical lactoferrin-derived peptide", Journal of Peptide Science, vol. 9, No. 5, (May 2003), pp. 300-311.
Bartlett, G.R.: "Colorimetric Assay Methods for Free and Phosphorylated Glyceric Acids", J. Biol.Chem, vol. 234, (1959), pp. 469-471.
Broekhuyse, R.M.: "Phospholipids in Tissues of the Eye: I. Isolation, Characterization, and Quantitative Analysis by Two-Dimensional This-Layer Chromatography of Diacyl and Vinyl-ether Phospholipids", Biochim. Biophys. Acta, vol. 152 (1968), pp. 307-315.
Chou, P.Y. et al.: "Empirical Predictions of Protein Conformation", Ann. Rev. Biochem,, vol. 47, (1978), pp. 251-276.
Coligan, J.E.: "Peptides: Introduction", Current Protocols in Immunology, (2002), pp. 9.0.1-9.0.2.
Deutscher, M.: "Rethinking Your Purification Procedure", Methods in Enzymology, vol. 182, (1990) pp. 779-780.
Fields, G.B.: "Introduction to Peptide Synthesis: Development of Solid-Phase Peptide Synthesis Methodology", Current Protocols in Immunology, (2002), pp. 9.1.1-9.1.9.
Harwig, Sylvia S. et al.: "Intramolecular disulfide bonds enhance the antimicrobial and lytic activities of protegrins at physiological sodium chloride concentrations", Eur. J. Biochem., vol. 240, (1996), pp. 352-357.
Jimenez-Monreal, A.M. et al.: "The phase behavior of aqueous dispersions of unsaturated mixtures of diacylglycerols and phospholipids", Biochimica et Biophysica Acta 1373, (1998), pp. 209-219.
Jing, W. et al.: "Headgroup structure and fatty acid chain length of the acidic phospholipids modulate the interaction of membrane mimetic vesicles with the antimicrobial peptide protegrin-1", Journal of Peptide Science, vol. 11, (2005), pp. 735-743.
Last, N.B. et al.: "A common landscape for membrane active peptides", Protein Science, vol. 22, (2013), pp. 870-882.
Lohner, K. et al.: "Molecular Mechanisms of Membrane Perturbation by Antimicrobial Peptides and the Use of Biophysical Studies in the Design of Novel Peptide Antibiotics", Combinatorial Chemistry & High Throughput Screening, vol. 8, No. 3, (2005), pp. 241-256.
Matsuzaki, K. et al.: "Role of Disulfide Linkages in Tachyplesin-Lipid Interactions", Biochemistry, vol. 32, (1993), pp. 11704-11710.
Maupetit, J. et al.: "PEP-FOLD: an online resource for de novo peptide structure prediction", Nucleic Acids Research, vol. 37, (2009), Web Server Issue, pp. 498-503.
McElhaney, R.N.: "The Use of Differential Scanning Calorimetry and Differential Thermal Analysis in Studies of Model and Biological Membranes", Chemistry and Physics of Lipids, vol. 30, (1982), pp. 229-259.
Merrifield, R.B.: "Solid Phase Peptide Synthesis: The Synthesis of a Tetrapeptide", (Jul. 1963), pp. 2149-2154.
Rekdal, O. et al.: "Relative Spatial Positions of Tryptophan and Cationic Residues in Helical Membrane-active Peptides Determine Their Cytotoxicity", The Journal of Biological Chemistry, vol. 281, No. 1, pp. 233-244.
Riedl, S. et al.: "In search of a novel target—Phosphatidylserine exposed by non-apoptotic tumor cells and metastases of malignancies with poor treatment efficacy", Biochimica et Biophysica Acta, vol. 1808, (2011), pp. 2638-2645.
Schroeder-Borm, H. et al.: "The NK-lysin derived peptide NK-2 preferentially kills cancer cells with increased surface levels of negatively charged phosphatidylserine", FEDS Letters, vol. 579, (2005), pp. 6128-6134.
Sevcsik, E. et al.: "How lipids influence the mode of action of membrane-active peptides", Biochimica et Biophysica Acta, vol. 1768, (2007), pp. 2586-2595.
Stewart, J.M. et al.: "Solid Phase Peptide Synthesis", (W.H. Freeman and Company, 1969).
Tamamura, H. et al.: "Synthesis of Protegrin-Related Peptides and Their Antibacterial and Anti-human Immunodeficiency Virus Activity", Chem. Pharm. Bull. vol. 43, No. 5, (1995), pp. 853-858.
Tao, T. et al.: "Fluorescence Lifetime Quenching Studies on the Accessibilities of Actin Sulfhydryl Sites", Actin Sulfhydryl Accessibilities, vol. 18, No. 13, (1979), pp. 2759-2765.
Thevenet, P. et al.: "PEP-FOLD: an updated de novo structure prediction server for both linear and disulfide bonded cyclic peptides", Nucleic Acids Research, vol. 40, (May 2012), Web Server Issue, pp. 288-293.
Toniolo, C. et al.: "Intramolecularly Hydrogen-Bonded Peptide Conformation", CRC Critical Reviews in Biochemistry, vol. 9, No. 1, (1980), pp. 1-44.
Wang, Q. et al.: "Biophysical Properties of Membrane-Active Peptides Based on Micelle Modeling: A Case Study of Cell-Penetrating and Antimicrobial Peptides", J. Phys. Chem., vol. 114, (2010), pp. 13726-13735.
Wimley, W. et al.: "Solvation Energies of Amino Acid Side Chains and Backbone in a Family of Host-Guest Pentapeptides", Biochemistry, vol. 35, (1996), pp. 5109-5124.
Whitmore, L. et al.: "DICHROWEB, an online server for protein secondary structure analyses from circular dichroism spectroscopic data", Nucleic Acids Research, vol. 32, (2004) Web Server Issue, pp. 668-673.
Whitmore, L. et al.: "Protein Secondary Structure Analyses from Circular Dichroism Spectroscopy: Methods and Reference Databases", Biopolymers, vol. 89, No. 5, (2007), pp. 392-400.
Zweytick, D. et al.: "Studies on Lactoferricin-derived *Escherichia coli* Membrane-active Peptides Reveal Differences in the Mechanism of N-Acylated Versus Nonacylated Peptides", The Journal of Biological Chemistry, vol. 286, No. 24, pp. 21266-21276.

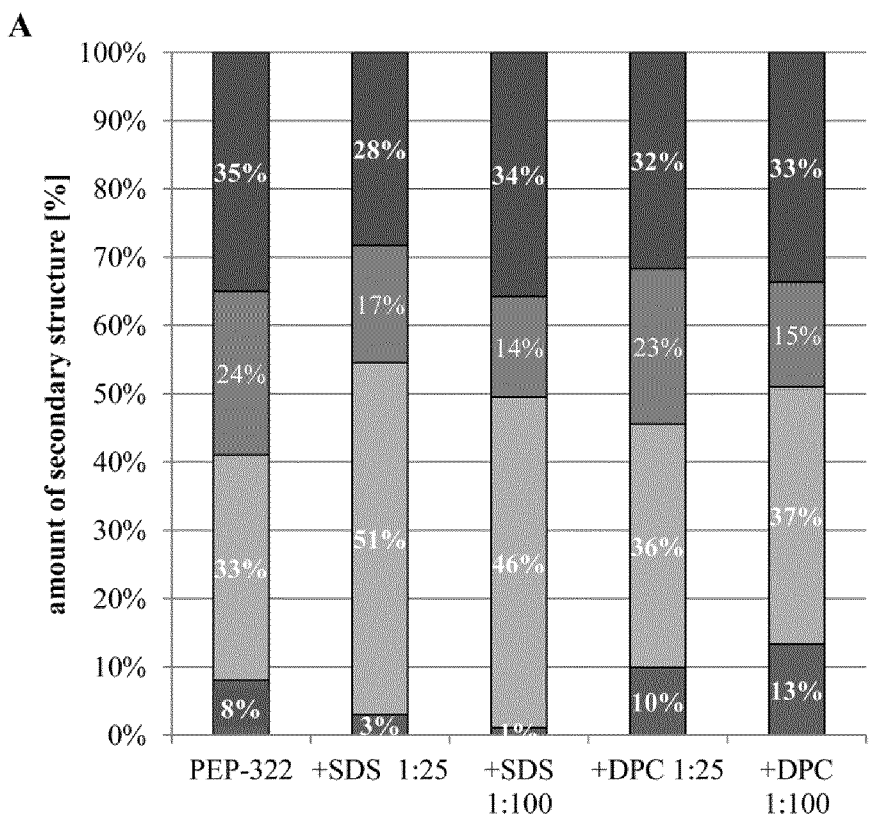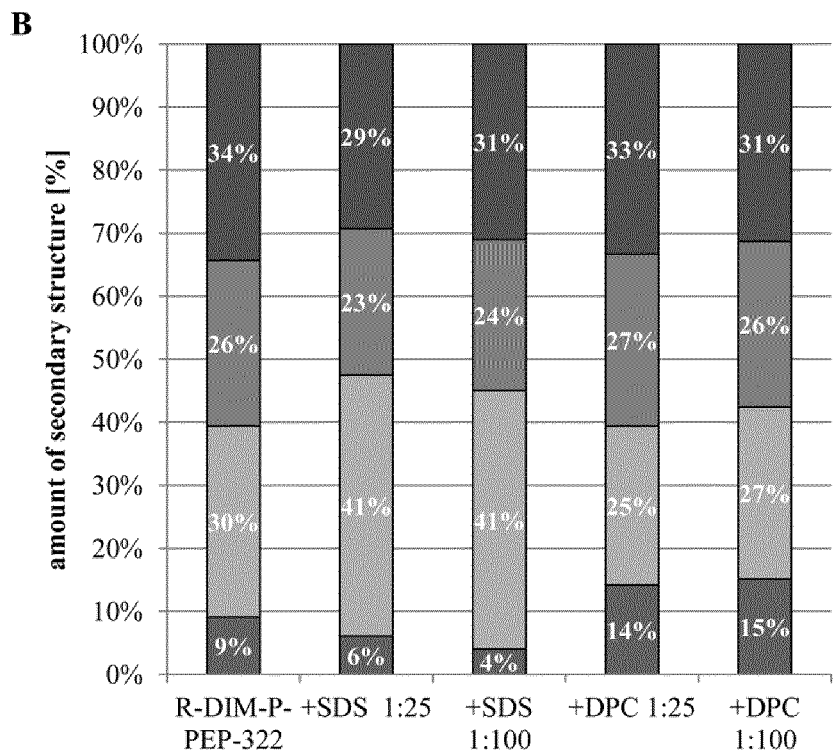
Fig. 1

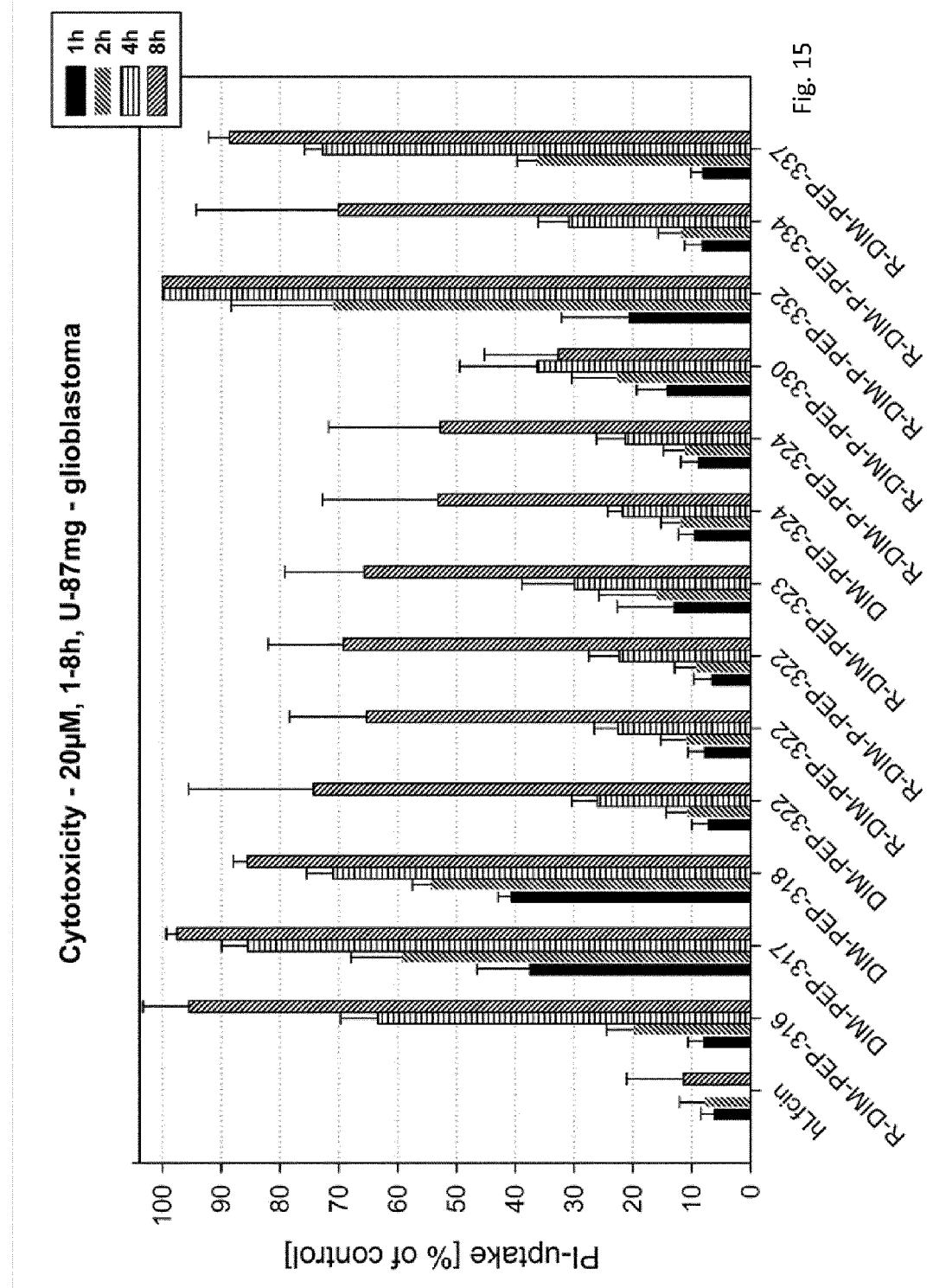

SEQUENCE LISTING

```
<160> NUMBER OF SEQ ID NOS: 207

<210> SEQ ID NO 1
<211> LENGTH: 9
<212> TYPE: PRT
<213> ORGANISM: Artificial Sequence
<220> FEATURE:
<223> OTHER INFORMATION: artificial peptide

<400> SEQUENCE: 1

Phe Trp Gln Arg Ile Arg Lys Val Arg
1               5

<210> SEQ ID NO 2
<211> LENGTH: 11
<212> TYPE: PRT
<213> ORGANISM: Artificial Sequence
<220> FEATURE:
<223> OTHER INFORMATION: artificial peptide

<400> SEQUENCE: 2

Phe Trp Gln Arg Arg Ile Arg Lys Val Arg Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: artificial peptide

<400> SEQUENCE: 3

Phe Trp Gln Arg Lys Ile Arg Lys Val Arg Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: artificial peptide

<400> SEQUENCE: 4
```

Phe Trp Gln Arg Asn Ile Arg Ile Arg Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: artificial peptide

<400> SEQUENCE: 5

Phe Trp Gln Arg Asn Ile Arg Lys Val Arg
1               5                   10

<210> SEQ ID NO 6
<211> LENGTH: 9
<212> TYPE: PRT
<213> ORGANISM: Artificial Sequence
<220> FEATURE:
<223> OTHER INFORMATION: artificial peptide

<400> SEQUENCE: 6

Phe Trp Gln Arg Asn Ile Arg Val Arg
1               5

<210> SEQ ID NO 7
<211> LENGTH: 11
<212> TYPE: PRT
<213> ORGANISM: Artificial Sequence
<220> FEATURE:
<223> OTHER INFORMATION: artificial peptide

<400> SEQUENCE: 7

Phe Trp Gln Arg Asn Ile Arg Lys Val Arg Arg
1               5                   10

<210> SEQ ID NO 8
<211> LENGTH: 11
<212> TYPE: PRT
<213> ORGANISM: Artificial Sequence
<220> FEATURE:
<223> OTHER INFORMATION: artificial peptide

<400> SEQUENCE: 8

Phe Trp Gln Arg Asn Ile Arg Lys Val Lys Lys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: artificial peptide

<400> SEQUENCE: 9

Phe Trp Gln Arg Asn Ile Arg Lys Val Arg Arg Arg
1               5                   10

<210> SEQ ID NO 10
<211> LENGTH: 12
<212> TYPE: PRT
<213> ORGANISM: Artificial Sequence
<220> FEATURE:
<223> OTHER INFORMATION: artificial peptide

<400> SEQUENCE: 10

```
Phe Trp Gln Arg Asn Ile Arg Lys Val Lys Lys Lys
1               5                   10

<210> SEQ ID NO 11
<211> LENGTH: 13
<212> TYPE: PRT
<213> ORGANISM: Artificial Sequence
<220> FEATURE:
<223> OTHER INFORMATION: artificial peptide

<400> SEQUENCE: 11

Phe Trp Gln Arg Asn Ile Arg Lys Val Arg Arg Arg
1               5                   10

<210> SEQ ID NO 12
<211> LENGTH: 13
<212> TYPE: PRT
<213> ORGANISM: Artificial Sequence
<220> FEATURE:
<223> OTHER INFORMATION: artificial peptide

<400> SEQUENCE: 12

Phe Trp Gln Arg Asn Ile Arg Lys Val Arg Arg Arg Ile
1               5                   10

<210> SEQ ID NO 13
<211> LENGTH: 13
<212> TYPE: PRT
<213> ORGANISM: Artificial Sequence
<220> FEATURE:
<223> OTHER INFORMATION: artificial peptide

<400> SEQUENCE: 13

Phe Trp Gln Arg Asn Ile Arg Lys Val Lys Lys Lys Lys
1               5                   10

<210> SEQ ID NO 14
<211> LENGTH: 13
<212> TYPE: PRT
<213> ORGANISM: Artificial Sequence
<220> FEATURE:
<223> OTHER INFORMATION: artificial peptide

<400> SEQUENCE: 14

Phe Trp Gln Arg Asn Ile Arg Lys Val Lys Lys Lys Ile
1               5                   10

<210> SEQ ID NO 15
<211> LENGTH: 10
<212> TYPE: PRT
<213> ORGANISM: Artificial Sequence
<220> FEATURE:
<223> OTHER INFORMATION: artificial peptide

<400> SEQUENCE: 15

Phe Trp Gln Arg Asn Ile Arg Lys Ile Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: artificial peptide

<400> SEQUENCE: 16

Phe Trp Gln Arg Asn Ile Arg Lys Leu Arg
```

```
<210> SEQ ID NO 17
<211> LENGTH: 10
<212> TYPE: PRT
<213> ORGANISM: Artificial Sequence
<220> FEATURE:
<223> OTHER INFORMATION: artificial peptide

<400> SEQUENCE: 17

Phe Trp Gln Arg Asn Ile Arg Lys Trp Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: artificial peptide

<400> SEQUENCE: 18

Phe Trp Gln Arg Asn Trp Arg Lys Val Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: artificial peptide

<400> SEQUENCE: 19

Phe Trp Gln Arg Asn Phe Arg Lys Val Arg
1               5                   10

<210> SEQ ID NO 20
<211> LENGTH: 10
<212> TYPE: PRT
<213> ORGANISM: Artificial Sequence
<220> FEATURE:
<223> OTHER INFORMATION: artificial peptide

<400> SEQUENCE: 20

Phe Trp Gln Arg Asn Tyr Arg Lys Val Arg
1               5                   10

<210> SEQ ID NO 21
<211> LENGTH: 10
<212> TYPE: PRT
<213> ORGANISM: Artificial Sequence
<220> FEATURE:
<223> OTHER INFORMATION: artificial peptide

<400> SEQUENCE: 21

Phe Trp Gln Arg Asn Ile Arg Lys Val Ser
1               5                   10

<210> SEQ ID NO 22
<211> LENGTH: 10
<212> TYPE: PRT
<213> ORGANISM: Artificial Sequence
<220> FEATURE:
<223> OTHER INFORMATION: artificial peptide

<400> SEQUENCE: 22

Phe Trp Gln Arg Arg Ile Arg Ile Arg Arg
1               5                   10
```

<210> SEQ ID NO 23
<211> LENGTH: 10
<212> TYPE: PRT
<213> ORGANISM: Artificial Sequence
<220> FEATURE:
<223> OTHER INFORMATION: artificial peptide

<400> SEQUENCE: 23

Phe Trp Gln Arg Pro Ile Arg Lys Val Arg
1               5                   10

<210> SEQ ID NO 24
<211> LENGTH: 10
<212> TYPE: PRT
<213> ORGANISM: Artificial Sequence
<220> FEATURE:
<223> OTHER INFORMATION: artificial peptide

<400> SEQUENCE: 24

Phe Trp Gln Arg Arg Ile Arg Lys Trp Arg
1               5                   10

<210> SEQ ID NO 25
<211> LENGTH: 11
<212> TYPE: PRT
<213> ORGANISM: Artificial Sequence
<220> FEATURE:
<223> OTHER INFORMATION: artificial peptide

<400> SEQUENCE: 25

Phe Trp Gln Arg Arg Ile Arg Arg Trp Arg Arg
1               5                   10

<210> SEQ ID NO 26
<211> LENGTH: 10
<212> TYPE: PRT
<213> ORGANISM: Artificial Sequence
<220> FEATURE:
<223> OTHER INFORMATION: artificial peptide

<400> SEQUENCE: 26

Phe Trp Pro Arg Asn Ile Arg Lys Val Arg
1               5                   10

<210> SEQ ID NO 27
<211> LENGTH: 10
<212> TYPE: PRT
<213> ORGANISM: Artificial Sequence
<220> FEATURE:
<223> OTHER INFORMATION: artificial peptide

<400> SEQUENCE: 27

Phe Trp Ala Arg Asn Ile Arg Lys Val Arg
1               5                   10

<210> SEQ ID NO 28
<211> LENGTH: 10
<212> TYPE: PRT
<213> ORGANISM: Artificial Sequence
<220> FEATURE:
<223> OTHER INFORMATION: artificial peptide

<400> SEQUENCE: 28

Phe Trp Ile Arg Asn Ile Arg Lys Val Arg
1               5                   10

<210> SEQ ID NO 29
<211> LENGTH: 10
<212> TYPE: PRT
<213> ORGANISM: Artificial Sequence
<220> FEATURE:
<223> OTHER INFORMATION: artificial peptide

<400> SEQUENCE: 29

Phe Trp Leu Arg Asn Ile Arg Lys Val Arg
1               5                   10

<210> SEQ ID NO 30
<211> LENGTH: 10
<212> TYPE: PRT
<213> ORGANISM: Artificial Sequence
<220> FEATURE:
<223> OTHER INFORMATION: artificial peptide

<400> SEQUENCE: 30

Phe Trp Val Arg Asn Ile Arg Lys Val Arg
1               5                   10

<210> SEQ ID NO 31
<211> LENGTH: 10
<212> TYPE: PRT
<213> ORGANISM: Artificial Sequence
<220> FEATURE:
<223> OTHER INFORMATION: artificial peptide

<400> SEQUENCE: 31

Phe Trp Gln Arg Asn Ile Phe Lys Val Arg
1               5                   10

<210> SEQ ID NO 32
<211> LENGTH: 10
<212> TYPE: PRT
<213> ORGANISM: Artificial Sequence
<220> FEATURE:
<223> OTHER INFORMATION: artificial peptide

<400> SEQUENCE: 32

Phe Trp Gln Arg Asn Ile Tyr Lys Val Arg
1               5                   10

<210> SEQ ID NO 33
<211> LENGTH: 11
<212> TYPE: PRT
<213> ORGANISM: Artificial Sequence
<220> FEATURE:
<223> OTHER INFORMATION: artificial peptide

<400> SEQUENCE: 33

Phe Ala Trp Gln Arg Asn Ile Arg Lys Val Arg
1               5                   10

<210> SEQ ID NO 34
<211> LENGTH: 11
<212> TYPE: PRT
<213> ORGANISM: Artificial Sequence
<220> FEATURE:
<223> OTHER INFORMATION: artificial peptide

<400> SEQUENCE: 34

Phe Ile Trp Gln Arg Asn Ile Arg Lys Val Arg
1               5                   10

```
<210> SEQ ID NO 35
<211> LENGTH: 11
<212> TYPE: PRT
<213> ORGANISM: Artificial Sequence
<220> FEATURE:
<223> OTHER INFORMATION: artificial peptide

<400> SEQUENCE: 35

Phe Leu Trp Gln Arg Asn Ile Arg Lys Val Arg
1               5                   10

<210> SEQ ID NO 36
<211> LENGTH: 11
<212> TYPE: PRT
<213> ORGANISM: Artificial Sequence
<220> FEATURE:
<223> OTHER INFORMATION: artificial peptide

<400> SEQUENCE: 36

Phe Val Trp Gln Arg Asn Ile Arg Lys Val Arg
1               5                   10

<210> SEQ ID NO 37
<211> LENGTH: 8
<212> TYPE: PRT
<213> ORGANISM: Artificial Sequence
<220> FEATURE:
<223> OTHER INFORMATION: artificial peptide

<400> SEQUENCE: 37

Phe Trp Arg Ile Arg Lys Trp Arg
1               5

<210> SEQ ID NO 38
<211> LENGTH: 8
<212> TYPE: PRT
<213> ORGANISM: Artificial Sequence
<220> FEATURE:
<223> OTHER INFORMATION: artificial peptide

<400> SEQUENCE: 38

Phe Trp Arg Ile Arg Lys Val Arg
1               5

<210> SEQ ID NO 39
<211> LENGTH: 6
<212> TYPE: PRT
<213> ORGANISM: Artificial Sequence
<220> FEATURE:
<223> OTHER INFORMATION: artificial peptide

<400> SEQUENCE: 39

Phe Trp Arg Trp Arg Arg
1               5

<210> SEQ ID NO 40
<211> LENGTH: 7
<212> TYPE: PRT
<213> ORGANISM: Artificial Sequence
<220> FEATURE:
<223> OTHER INFORMATION: artificial peptide

<400> SEQUENCE: 40

Phe Trp Arg Arg Trp Arg Arg
1               5

<210> SEQ ID NO 41
```

```
<211> LENGTH: 8
<212> TYPE: PRT
<213> ORGANISM: Artificial Sequence
<220> FEATURE:
<223> OTHER INFORMATION: artificial peptide

<400> SEQUENCE: 41

Phe Trp Arg Arg Trp Ile Arg Arg
1               5

<210> SEQ ID NO 42
<211> LENGTH: 9
<212> TYPE: PRT
<213> ORGANISM: Artificial Sequence
<220> FEATURE:
<223> OTHER INFORMATION: artificial peptide

<400> SEQUENCE: 42

Phe Trp Arg Gly Trp Arg Ile Arg Arg
1               5

<210> SEQ ID NO 43
<211> LENGTH: 8
<212> TYPE: PRT
<213> ORGANISM: Artificial Sequence
<220> FEATURE:
<223> OTHER INFORMATION: artificial peptide

<400> SEQUENCE: 43

Phe Trp Arg Arg Phe Trp Arg Arg
1               5

<210> SEQ ID NO 44
<211> LENGTH: 7
<212> TYPE: PRT
<213> ORGANISM: Artificial Sequence
<220> FEATURE:
<223> OTHER INFORMATION: artificial peptide

<400> SEQUENCE: 44

Phe Trp Arg Trp Arg Trp Arg
1               5

<210> SEQ ID NO 45
<211> LENGTH: 8
<212> TYPE: PRT
<213> ORGANISM: Artificial Sequence
<220> FEATURE:
<223> OTHER INFORMATION: artificial peptide

<400> SEQUENCE: 45

Phe Trp Arg Ile Trp Arg Trp Arg
1               5

<210> SEQ ID NO 46
<211> LENGTH: 9
<212> TYPE: PRT
<213> ORGANISM: Artificial Sequence
<220> FEATURE:
<223> OTHER INFORMATION: artificial peptide

<400> SEQUENCE: 46

Phe Trp Arg Ile Trp Arg Ile Trp Arg
1               5

<210> SEQ ID NO 47
<211> LENGTH: 9
```

```
<212> TYPE: PRT
<213> ORGANISM: Artificial Sequence
<220> FEATURE:
<223> OTHER INFORMATION: artificial peptide

<400> SEQUENCE: 47

Phe Trp Arg Asn Ile Arg Lys Trp Arg
1               5

<210> SEQ ID NO 48
<211> LENGTH: 10
<212> TYPE: PRT
<213> ORGANISM: Artificial Sequence
<220> FEATURE:
<223> OTHER INFORMATION: artificial peptide

<400> SEQUENCE: 48

Phe Trp Arg Arg Arg Ile Arg Ile Arg Arg
1               5                   10

<210> SEQ ID NO 49
<211> LENGTH: 8
<212> TYPE: PRT
<213> ORGANISM: Artificial Sequence
<220> FEATURE:
<223> OTHER INFORMATION: artificial peptide

<400> SEQUENCE: 49

Phe Ile Trp Arg Trp Arg Trp Arg
1               5

<210> SEQ ID NO 50
<211> LENGTH: 9
<212> TYPE: PRT
<213> ORGANISM: Artificial Sequence
<220> FEATURE:
<223> OTHER INFORMATION: artificial peptide

<400> SEQUENCE: 50

Pro Phe Trp Arg Trp Arg Ile Trp Arg
1               5

<210> SEQ ID NO 51
<211> LENGTH: 9
<212> TYPE: PRT
<213> ORGANISM: Artificial Sequence
<220> FEATURE:
<223> OTHER INFORMATION: artificial peptide

<400> SEQUENCE: 51

Pro Phe Trp Arg Ile Arg Ile Arg Arg
1               5

<210> SEQ ID NO 52
<211> LENGTH: 9
<212> TYPE: PRT
<213> ORGANISM: Artificial Sequence
<220> FEATURE:
<223> OTHER INFORMATION: artificial peptide

<400> SEQUENCE: 52

Pro Phe Trp Arg Gln Arg Ile Arg Arg
1               5

<210> SEQ ID NO 53
<211> LENGTH: 9
<212> TYPE: PRT
```

<213> ORGANISM: Artificial Sequence
<220> FEATURE:
<223> OTHER INFORMATION: artificial peptide

<400> SEQUENCE: 53

Pro Phe Trp Arg Ala Arg Ile Arg Arg
1               5

<210> SEQ ID NO 54
<211> LENGTH: 9
<212> TYPE: PRT
<213> ORGANISM: Artificial Sequence
<220> FEATURE:
<223> OTHER INFORMATION: artificial peptide

<400> SEQUENCE: 54

Pro Phe Trp Arg Lys Arg Ile Arg Arg
1               5

<210> SEQ ID NO 55
<211> LENGTH: 9
<212> TYPE: PRT
<213> ORGANISM: Artificial Sequence
<220> FEATURE:
<223> OTHER INFORMATION: artificial peptide

<400> SEQUENCE: 55

Pro Phe Trp Arg Lys Arg Leu Arg Arg
1               5

<210> SEQ ID NO 56
<211> LENGTH: 9
<212> TYPE: PRT
<213> ORGANISM: Artificial Sequence
<220> FEATURE:
<223> OTHER INFORMATION: artificial peptide

<400> SEQUENCE: 56

Pro Phe Trp Arg Lys Arg Trp Arg Arg
1               5

<210> SEQ ID NO 57
<211> LENGTH: 9
<212> TYPE: PRT
<213> ORGANISM: Artificial Sequence
<220> FEATURE:
<223> OTHER INFORMATION: artificial peptide

<400> SEQUENCE: 57

Pro Phe Trp Arg Arg Arg Ile Arg Arg
1               5

<210> SEQ ID NO 58
<211> LENGTH: 9
<212> TYPE: PRT
<213> ORGANISM: Artificial Sequence
<220> FEATURE:
<223> OTHER INFORMATION: artificial peptide

<400> SEQUENCE: 58

Pro Phe Trp Arg Arg Arg Trp Arg Arg
1               5

<210> SEQ ID NO 59
<211> LENGTH: 10
<212> TYPE: PRT
<213> ORGANISM: Artificial Sequence

```
<220> FEATURE:
<223> OTHER INFORMATION: artificial peptide

<400> SEQUENCE: 59

Pro Phe Trp Arg Ile Arg Ile Arg Arg Asp
1               5                   10

<210> SEQ ID NO 60
<211> LENGTH: 10
<212> TYPE: PRT
<213> ORGANISM: Artificial Sequence
<220> FEATURE:
<223> OTHER INFORMATION: artificial peptide

<400> SEQUENCE: 60

Pro Phe Phe Trp Arg Ile Arg Ile Arg Arg
1               5                   10

<210> SEQ ID NO 61
<211> LENGTH: 8
<212> TYPE: PRT
<213> ORGANISM: Artificial Sequence
<220> FEATURE:
<223> OTHER INFORMATION: artificial peptide

<400> SEQUENCE: 61

Pro Trp Arg Ile Arg Ile Arg Arg
1               5

<210> SEQ ID NO 62
<211> LENGTH: 12
<212> TYPE: PRT
<213> ORGANISM: Artificial Sequence
<220> FEATURE:
<223> OTHER INFORMATION: artificial peptide

<400> SEQUENCE: 62

Arg Phe Trp Gln Arg Asn Ile Arg Lys Val Arg Arg
1               5                   10

<210> SEQ ID NO 63
<211> LENGTH: 11
<212> TYPE: PRT
<213> ORGANISM: Artificial Sequence
<220> FEATURE:
<223> OTHER INFORMATION: artificial peptide

<400> SEQUENCE: 63

Arg Phe Trp Gln Arg Asn Ile Arg Lys Tyr Arg
1               5                   10

<210> SEQ ID NO 64
<211> LENGTH: 11
<212> TYPE: PRT
<213> ORGANISM: Artificial Sequence
<220> FEATURE:
<223> OTHER INFORMATION: artificial peptide

<400> SEQUENCE: 64

Pro Phe Trp Gln Arg Asn Ile Arg Lys Trp Arg
1               5                   10

<210> SEQ ID NO 65
<211> LENGTH: 13
<212> TYPE: PRT
<213> ORGANISM: Artificial Sequence
<220> FEATURE:
```

<223> OTHER INFORMATION: artificial peptide

<400> SEQUENCE: 65

Arg Phe Arg Trp Gln Arg Asn Ile Arg Lys Tyr Arg Arg
1               5                   10

<210> SEQ ID NO 66
<211> LENGTH: 10
<212> TYPE: PRT
<213> ORGANISM: Artificial Sequence
<220> FEATURE:
<223> OTHER INFORMATION: artificial peptide

<400> SEQUENCE: 66

Arg Trp Lys Arg Ile Asn Arg Gln Trp Phe
1               5                   10

<210> SEQ ID NO 67
<211> LENGTH: 7
<212> TYPE: PRT
<213> ORGANISM: Artificial Sequence
<220> FEATURE:
<223> OTHER INFORMATION: artificial peptide

<400> SEQUENCE: 67

Lys Arg Phe Cys Phe Lys Lys
1               5

<210> SEQ ID NO 68
<211> LENGTH: 8
<212> TYPE: PRT
<213> ORGANISM: Artificial Sequence
<220> FEATURE:
<223> OTHER INFORMATION: artificial peptide

<400> SEQUENCE: 68

Lys Arg Phe Ser Phe Lys Lys Cys
1               5

<210> SEQ ID NO 69
<211> LENGTH: 7
<212> TYPE: PRT
<213> ORGANISM: Artificial Sequence
<220> FEATURE:
<223> OTHER INFORMATION: artificial peptide

<400> SEQUENCE: 69

Lys Arg Trp Ser Trp Lys Lys
1               5

<210> SEQ ID NO 70
<211> LENGTH: 7
<212> TYPE: PRT
<213> ORGANISM: Artificial Sequence
<220> FEATURE:
<223> OTHER INFORMATION: artificial peptide

<400> SEQUENCE: 70

Phe Arg Phe Ser Phe Lys Lys
1               5

<210> SEQ ID NO 71
<211> LENGTH: 7
<212> TYPE: PRT
<213> ORGANISM: Artificial Sequence
<220> FEATURE:
<223> OTHER INFORMATION: artificial peptide

<400> SEQUENCE: 71

Arg Arg Phe Trp Phe Arg Arg
1               5

<210> SEQ ID NO 72
<211> LENGTH: 9
<212> TYPE: PRT
<213> ORGANISM: Artificial Sequence
<220> FEATURE:
<223> OTHER INFORMATION: artificial peptide

<400> SEQUENCE: 72

Phe Trp Arg Asn Ile Arg Ile Arg Arg
1               5

<210> SEQ ID NO 73
<211> LENGTH: 9
<212> TYPE: PRT
<213> ORGANISM: Artificial Sequence
<220> FEATURE:
<223> OTHER INFORMATION: artificial peptide

<400> SEQUENCE: 73

Phe Trp Gln Arg Ile Arg Ile Arg Arg
1               5

<210> SEQ ID NO 74
<211> LENGTH: 8
<212> TYPE: PRT
<213> ORGANISM: Artificial Sequence
<220> FEATURE:
<223> OTHER INFORMATION: artificial peptide

<400> SEQUENCE: 74

Phe Trp Arg Trp Arg Ile Trp Arg
1               5

<210> SEQ ID NO 75
<211> LENGTH: 8
<212> TYPE: PRT
<213> ORGANISM: Artificial Sequence
<220> FEATURE:
<223> OTHER INFORMATION: artificial peptide

<400> SEQUENCE: 75

Phe Trp Arg Ile Arg Ile Arg Arg
1               5

<210> SEQ ID NO 76
<211> LENGTH: 10
<212> TYPE: PRT
<213> ORGANISM: Artificial Sequence
<220> FEATURE:
<223> OTHER INFORMATION: artificial peptide

<400> SEQUENCE: 76

Phe Trp Arg Asn Ile Arg Ile Trp Arg Arg
1               5                   10

<210> SEQ ID NO 77
<211> LENGTH: 9
<212> TYPE: PRT
<213> ORGANISM: Artificial Sequence
<220> FEATURE:
<223> OTHER INFORMATION: artificial peptide

```
<400> SEQUENCE: 77

Phe Trp Arg Asn Ile Arg Ile Arg Arg
1               5

<210> SEQ ID NO 78
<211> LENGTH: 11
<212> TYPE: PRT
<213> ORGANISM: Artificial Sequence
<220> FEATURE:
<223> OTHER INFORMATION: artificial peptide

<400> SEQUENCE: 78

Arg Phe Trp Gln Arg Asn Ile Arg Ile Arg Arg
1               5                   10

<210> SEQ ID NO 79
<211> LENGTH: 10
<212> TYPE: PRT
<213> ORGANISM: Artificial Sequence
<220> FEATURE:
<223> OTHER INFORMATION: artificial peptide

<400> SEQUENCE: 79

Arg Trp Gln Arg Asn Ile Arg Ile Arg Arg
1               5                   10

<210> SEQ ID NO 80
<211> LENGTH: 10
<212> TYPE: PRT
<213> ORGANISM: Artificial Sequence
<220> FEATURE:
<223> OTHER INFORMATION: artificial peptide

<400> SEQUENCE: 80

Arg Arg Ile Arg Ile Asn Arg Gln Trp Phe
1               5                   10

<210> SEQ ID NO 81
<211> LENGTH: 9
<212> TYPE: PRT
<213> ORGANISM: Artificial Sequence
<220> FEATURE:
<223> OTHER INFORMATION: artificial peptide

<400> SEQUENCE: 81

Pro Phe Trp Arg Arg Gln Ile Arg Arg
1               5

<210> SEQ ID NO 82
<211> LENGTH: 9
<212> TYPE: PRT
<213> ORGANISM: Artificial Sequence
<220> FEATURE:
<223> OTHER INFORMATION: artificial peptide

<400> SEQUENCE: 82

Pro Phe Trp Arg Lys Lys Leu Lys Arg
1               5

<210> SEQ ID NO 83
<211> LENGTH: 7
<212> TYPE: PRT
<213> ORGANISM: Artificial Sequence
<220> FEATURE:
<223> OTHER INFORMATION: artificial peptide

<400> SEQUENCE: 83
```

```
Pro Trp Arg Arg Ile Arg Arg
1               5

<210> SEQ ID NO 84
<211> LENGTH: 8
<212> TYPE: PRT
<213> ORGANISM: Artificial Sequence
<220> FEATURE:
<223> OTHER INFORMATION: artificial peptide

<400> SEQUENCE: 84

Pro Trp Arg Arg Lys Ile Arg Arg
1               5

<210> SEQ ID NO 85
<211> LENGTH: 11
<212> TYPE: PRT
<213> ORGANISM: Artificial Sequence
<220> FEATURE:
<223> OTHER INFORMATION: artificial peptide

<400> SEQUENCE: 85

Pro Phe Trp Arg Arg Arg Ile Arg Ile Arg Arg
1               5                   10

<210> SEQ ID NO 86
<211> LENGTH: 7
<212> TYPE: PRT
<213> ORGANISM: Artificial Sequence
<220> FEATURE:
<223> OTHER INFORMATION: artificial peptide

<400> SEQUENCE: 86

Arg Arg Trp Phe Trp Arg Arg
1               5

<210> SEQ ID NO 87
<211> LENGTH: 11
<212> TYPE: PRT
<213> ORGANISM: Artificial Sequence
<220> FEATURE:
<223> OTHER INFORMATION: artificial peptide

<400> SEQUENCE: 87

Phe Gln Trp Gln Arg Asn Ile Arg Lys Val Arg
1               5                   10

<210> SEQ ID NO 88
<211> LENGTH: 22
<212> TYPE: PRT
<213> ORGANISM: Artificial Sequence
<220> FEATURE:
<223> OTHER INFORMATION: artificial peptide

<400> SEQUENCE: 88

Phe Gln Trp Gln Arg Asn Ile Arg Lys Val Arg Phe Gln Trp Gln Arg
1               5                   10                  15

Asn Ile Arg Lys Val Arg
            20

<210> SEQ ID NO 89
<211> LENGTH: 25
<212> TYPE: PRT
<213> ORGANISM: Artificial Sequence
<220> FEATURE:
<223> OTHER INFORMATION: artificial peptide
```

```
<220> FEATURE:
<221> NAME/KEY: MISC_FEATURE
<222> LOCATION: (12)..(14)
<223> OTHER INFORMATION: Xaa = (Pro and/or, preferably or, Gly), wherein
      up to two of these positions may be absent

<400> SEQUENCE: 89

Phe Gln Trp Gln Arg Asn Ile Arg Lys Val Arg Xaa Xaa Xaa Phe Gln
1               5                   10                  15

Trp Gln Arg Asn Ile Arg Lys Val Arg
            20                  25

<210> SEQ ID NO 90
<211> LENGTH: 22
<212> TYPE: PRT
<213> ORGANISM: Artificial Sequence
<220> FEATURE:
<223> OTHER INFORMATION: artificial peptide

<400> SEQUENCE: 90

Phe Gln Trp Gln Arg Asn Ile Arg Lys Val Arg Val Lys Arg Ile
1               5                   10                  15

Asn Arg Gln Trp Gln Phe
            20

<210> SEQ ID NO 91
<211> LENGTH: 25
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (12)..(14)
<223> OTHER INFORMATION: Xaa = (Pro and/or, preferably or, Gly), wherein
      up to two of these positions may be absent

<400> SEQUENCE: 91

Phe Gln Trp Gln Arg Asn Ile Arg Lys Val Arg Xaa Xaa Xaa Arg Val
1               5                   10                  15

Lys Arg Ile Asn Arg Gln Trp Gln Phe
            20                  25

<210> SEQ ID NO 92
<211> LENGTH: 20
<212> TYPE: PRT
<213> ORGANISM: Artificial Sequence
<220> FEATURE:
<223> OTHER INFORMATION: artificial peptide

<400> SEQUENCE: 92

Phe Trp Gln Arg Asn Ile Arg Ile Arg Arg Phe Trp Gln Arg Asn Ile
1               5                   10                  15

Arg Ile Arg Arg
            20

<210> SEQ ID NO 93
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent
```

<400> SEQUENCE: 93

Phe Trp Gln Arg Asn Ile Arg Ile Arg Arg Xaa Xaa Xaa Phe Trp Gln
1               5                   10                  15

Arg Asn Ile Arg Ile Arg Arg
            20

<210> SEQ ID NO 94
<211> LENGTH: 20
<212> TYPE: PRT
<213> ORGANISM: Artificial Sequence
<220> FEATURE:
<223> OTHER INFORMATION: artificial peptide

<400> SEQUENCE: 94

Phe Trp Gln Arg Asn Ile Arg Ile Arg Arg Arg Arg Ile Arg Ile Asn
1               5                   10                  15

Arg Gln Trp Phe
            20

<210> SEQ ID NO 95
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 95

Phe Trp Gln Arg Asn Ile Arg Ile Arg Arg Xaa Xaa Xaa Arg Arg Ile
1               5                   10                  15

Arg Ile Asn Arg Gln Trp Phe
            20

<210> SEQ ID NO 96
<211> LENGTH: 20
<212> TYPE: PRT
<213> ORGANISM: Artificial Sequence
<220> FEATURE:
<223> OTHER INFORMATION: artificial peptide

<400> SEQUENCE: 96

Arg Arg Ile Arg Ile Asn Arg Gln Trp Phe Arg Arg Ile Arg Ile Asn
1               5                   10                  15

Arg Gln Trp Phe
            20

<210> SEQ ID NO 97
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 97

Arg Arg Ile Arg Ile Asn Arg Gln Trp Phe Xaa Xaa Xaa Arg Arg Ile
1               5                   10                  15

Arg Ile Asn Arg Gln Trp Phe
            20

<210> SEQ ID NO 98
<211> LENGTH: 20
<212> TYPE: PRT
<213> ORGANISM: Artificial Sequence
<220> FEATURE:
<223> OTHER INFORMATION: artificial peptide

<400> SEQUENCE: 98

Arg Arg Ile Arg Ile Asn Arg Gln Trp Phe Phe Trp Gln Arg Asn Ile
1               5                   10                  15

Arg Ile Arg Arg
            20

<210> SEQ ID NO 99
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 99

Arg Arg Ile Arg Ile Asn Arg Gln Trp Phe Xaa Xaa Xaa Phe Trp Gln
1               5                   10                  15

Arg Asn Ile Arg Ile Arg Arg
            20

<210> SEQ ID NO 100
<211> LENGTH: 20
<212> TYPE: PRT
<213> ORGANISM: Artificial Sequence
<220> FEATURE:
<223> OTHER INFORMATION: artificial peptide

<400> SEQUENCE: 100

Phe Trp Gln Arg Asn Ile Arg Lys Trp Arg Phe Trp Gln Arg Asn Ile
1               5                   10                  15

Arg Lys Trp Arg
            20

<210> SEQ ID NO 101
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 101

Phe Trp Gln Arg Asn Ile Arg Lys Trp Arg Xaa Xaa Xaa Phe Trp Gln
1               5                   10                  15

Arg Asn Ile Arg Lys Trp Arg
            20

```
<210> SEQ ID NO 102
<211> LENGTH: 20
<212> TYPE: PRT
<213> ORGANISM: Artificial Sequence
<220> FEATURE:
<223> OTHER INFORMATION: artificial peptide

<400> SEQUENCE: 102

Phe Trp Gln Arg Asn Ile Arg Lys Trp Arg Arg Trp Lys Arg Ile Asn
1               5                   10                  15

Arg Gln Trp Phe
            20

<210> SEQ ID NO 103
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 103

Phe Trp Gln Arg Asn Ile Arg Lys Trp Arg Xaa Xaa Xaa Arg Trp Lys
1               5                   10                  15

Arg Ile Asn Arg Gln Trp Phe
            20

<210> SEQ ID NO 104
<211> LENGTH: 20
<212> TYPE: PRT
<213> ORGANISM: Artificial Sequence
<220> FEATURE:
<223> OTHER INFORMATION: artificial peptide

<400> SEQUENCE: 104

Arg Trp Lys Arg Ile Asn Arg Gln Trp Phe Arg Trp Lys Arg Ile Asn
1               5                   10                  15

Arg Gln Trp Phe
            20

<210> SEQ ID NO 105
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 105

Arg Trp Lys Arg Ile Asn Arg Gln Trp Phe Xaa Xaa Xaa Arg Trp Lys
1               5                   10                  15

Arg Ile Asn Arg Gln Trp Phe
            20

<210> SEQ ID NO 106
<211> LENGTH: 20
<212> TYPE: PRT
<213> ORGANISM: Artificial Sequence
<220> FEATURE:
```

<223> OTHER INFORMATION: artificial peptide

<400> SEQUENCE: 106

Arg Trp Lys Arg Ile Asn Arg Gln Trp Phe Phe Trp Gln Arg Asn Ile
1               5                   10                  15
Arg Lys Trp Arg
            20

<210> SEQ ID NO 107
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 107

Arg Trp Lys Arg Ile Asn Arg Gln Trp Phe Xaa Xaa Xaa Phe Trp Gln
1               5                   10                  15
Arg Asn Ile Arg Lys Trp Arg
            20

<210> SEQ ID NO 108
<211> LENGTH: 20
<212> TYPE: PRT
<213> ORGANISM: Artificial Sequence
<220> FEATURE:
<223> OTHER INFORMATION: artificial peptide

<400> SEQUENCE: 108

Phe Trp Gln Arg Arg Ile Arg Lys Trp Arg Phe Trp Gln Arg Arg Ile
1               5                   10                  15
Arg Lys Trp Arg
            20

<210> SEQ ID NO 109
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 109

Phe Trp Gln Arg Arg Ile Arg Lys Trp Arg Xaa Xaa Xaa Phe Trp Gln
1               5                   10                  15
Arg Arg Ile Arg Lys Trp Arg
            20

<210> SEQ ID NO 110
<211> LENGTH: 20
<212> TYPE: PRT
<213> ORGANISM: Artificial Sequence
<220> FEATURE:
<223> OTHER INFORMATION: artificial peptide

<400> SEQUENCE: 110

Phe Trp Gln Arg Arg Ile Arg Lys Trp Arg Arg Trp Lys Arg Ile Arg

```
                            1               5                   10                  15

Arg Gln Trp Phe
                20

<210> SEQ ID NO 111
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 111

Phe Trp Gln Arg Arg Ile Arg Lys Trp Arg Xaa Xaa Xaa Arg Trp Lys
1               5                   10                  15

Arg Ile Arg Arg Gln Trp Phe
                20

<210> SEQ ID NO 112
<211> LENGTH: 11
<212> TYPE: PRT
<213> ORGANISM: Artificial Sequence
<220> FEATURE:
<223> OTHER INFORMATION: artificial peptide

<400> SEQUENCE: 112

Phe Trp Gln Arg Arg Ile Arg Arg Trp Arg Arg
1               5                   10

<210> SEQ ID NO 113
<211> LENGTH: 22
<212> TYPE: PRT
<213> ORGANISM: Artificial Sequence
<220> FEATURE:
<223> OTHER INFORMATION: artificial peptide

<400> SEQUENCE: 113

Phe Trp Gln Arg Arg Ile Arg Arg Trp Arg Arg Phe Trp Gln Arg Arg
1               5                   10                  15

Ile Arg Arg Trp Arg Arg
                20

<210> SEQ ID NO 114
<211> LENGTH: 25
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (12)..(14)
<223> OTHER INFORMATION: Xaa = (Pro and/or, preferably or, Gly), wherein
      up to two of these positions may be absent

<400> SEQUENCE: 114

Phe Trp Gln Arg Arg Ile Arg Arg Trp Arg Arg Xaa Xaa Xaa Phe Trp
1               5                   10                  15

Gln Arg Arg Ile Arg Arg Trp Arg Arg
                20                  25

<210> SEQ ID NO 115
<211> LENGTH: 22
```

```
<212> TYPE: PRT
<213> ORGANISM: Artificial Sequence
<220> FEATURE:
<223> OTHER INFORMATION: artificial peptide

<400> SEQUENCE: 115

Phe Trp Gln Arg Arg Ile Arg Arg Trp Arg Arg Arg Arg Trp Arg Arg
1               5                   10                  15

Ile Arg Arg Gln Trp Phe
            20

<210> SEQ ID NO 116
<211> LENGTH: 25
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (12)..(14)
<223> OTHER INFORMATION: Xaa = (Pro and/or, preferably or, Gly), wherein
      up to two of these positions may be absent

<400> SEQUENCE: 116

Phe Trp Gln Arg Arg Ile Arg Arg Trp Arg Arg Xaa Xaa Xaa Arg Arg
1               5                   10                  15

Trp Arg Arg Ile Arg Arg Gln Trp Phe
            20                  25

<210> SEQ ID NO 117
<211> LENGTH: 22
<212> TYPE: PRT
<213> ORGANISM: Artificial Sequence
<220> FEATURE:
<223> OTHER INFORMATION: artificial peptide

<400> SEQUENCE: 117

Pro Phe Trp Gln Arg Asn Ile Arg Lys Trp Arg Pro Phe Trp Gln Arg
1               5                   10                  15

Asn Ile Arg Lys Trp Arg
            20

<210> SEQ ID NO 118
<211> LENGTH: 25
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (12)..(14)
<223> OTHER INFORMATION: Xaa = (Pro and/or, preferably or, Gly), wherein
      up to two of these positions may be absent

<400> SEQUENCE: 118

Pro Phe Trp Gln Arg Asn Ile Arg Lys Trp Arg Xaa Xaa Xaa Pro Phe
1               5                   10                  15

Trp Gln Arg Asn Ile Arg Lys Trp Arg
            20                  25

<210> SEQ ID NO 119
<211> LENGTH: 22
<212> TYPE: PRT
<213> ORGANISM: Artificial Sequence
<220> FEATURE:
<223> OTHER INFORMATION: artificial peptide
```

```
<400> SEQUENCE: 119

Pro Phe Trp Gln Arg Asn Ile Arg Lys Trp Arg Arg Trp Lys Arg Ile
1               5                   10                  15

Asn Arg Gln Trp Phe Pro
            20

<210> SEQ ID NO 120
<211> LENGTH: 25
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (12)..(14)
<223> OTHER INFORMATION: Xaa = (Pro and/or, preferably or, Gly), wherein
      up to two of these positions may be absent

<400> SEQUENCE: 120

Pro Phe Trp Gln Arg Asn Ile Arg Lys Trp Arg Xaa Xaa Xaa Arg Trp
1               5                   10                  15

Lys Arg Ile Asn Arg Gln Trp Phe Pro
            20                  25

<210> SEQ ID NO 121
<211> LENGTH: 18
<212> TYPE: PRT
<213> ORGANISM: Artificial Sequence
<220> FEATURE:
<223> OTHER INFORMATION: artificial peptide

<400> SEQUENCE: 121

Phe Trp Arg Asn Ile Arg Lys Trp Arg Phe Trp Arg Asn Ile Arg Lys
1               5                   10                  15

Trp Arg

<210> SEQ ID NO 122
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 122

Phe Trp Arg Asn Ile Arg Lys Trp Arg Xaa Xaa Xaa Phe Trp Arg Asn
1               5                   10                  15

Ile Arg Lys Trp Arg
            20

<210> SEQ ID NO 123
<211> LENGTH: 18
<212> TYPE: PRT
<213> ORGANISM: Artificial Sequence
<220> FEATURE:
<223> OTHER INFORMATION: artificial peptide

<400> SEQUENCE: 123

Phe Trp Arg Asn Ile Arg Lys Trp Arg Arg Trp Lys Arg Ile Asn Arg
1               5                   10                  15

Trp Phe
```

<210> SEQ ID NO 124
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 124

Phe Trp Arg Asn Ile Arg Lys Trp Arg Xaa Xaa Xaa Arg Trp Lys Arg
1               5                   10                  15

Ile Asn Arg Trp Phe
            20

<210> SEQ ID NO 125
<211> LENGTH: 18
<212> TYPE: PRT
<213> ORGANISM: Artificial Sequence
<220> FEATURE:
<223> OTHER INFORMATION: artificial peptide

<400> SEQUENCE: 125

Pro Phe Trp Arg Ile Arg Ile Arg Arg Pro Phe Trp Arg Ile Arg Ile
1               5                   10                  15

Arg Arg

<210> SEQ ID NO 126
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 126

Pro Phe Trp Arg Ile Arg Ile Arg Arg Xaa Xaa Xaa Pro Phe Trp Arg
1               5                   10                  15

Ile Arg Ile Arg Arg
            20

<210> SEQ ID NO 127
<211> LENGTH: 18
<212> TYPE: PRT
<213> ORGANISM: Artificial Sequence
<220> FEATURE:
<223> OTHER INFORMATION: artificial peptide

<400> SEQUENCE: 127

Pro Phe Trp Arg Ile Arg Ile Arg Arg Arg Ile Arg Ile Arg Trp
1               5                   10                  15

Phe Pro

<210> SEQ ID NO 128
<211> LENGTH: 21
<212> TYPE: PRT
<213> ORGANISM: Artificial Sequence
<220> FEATURE:

```
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 128

Pro Phe Trp Arg Ile Arg Ile Arg Arg Xaa Xaa Xaa Arg Arg Ile Arg
1               5                   10                  15

Ile Arg Trp Phe Pro
            20

<210> SEQ ID NO 129
<211> LENGTH: 16
<212> TYPE: PRT
<213> ORGANISM: Artificial Sequence
<220> FEATURE:
<223> OTHER INFORMATION: artificial peptide

<400> SEQUENCE: 129

Phe Trp Arg Ile Arg Ile Arg Arg Phe Trp Arg Ile Arg Ile Arg Arg
1               5                   10                  15

<210> SEQ ID NO 130
<211> LENGTH: 19
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (9)..(11)
<223> OTHER INFORMATION: Xaa = (Pro and/or, preferably or, Gly), wherein
      up to two of these positions may be absent

<400> SEQUENCE: 130

Phe Trp Arg Ile Arg Ile Arg Arg Xaa Xaa Xaa Phe Trp Arg Ile Arg
1               5                   10                  15

Ile Arg Arg

<210> SEQ ID NO 131
<211> LENGTH: 16
<212> TYPE: PRT
<213> ORGANISM: Artificial Sequence
<220> FEATURE:
<223> OTHER INFORMATION: artificial peptide

<400> SEQUENCE: 131

Phe Trp Arg Ile Arg Ile Arg Arg Arg Arg Ile Arg Ile Arg Trp Phe
1               5                   10                  15

<210> SEQ ID NO 132
<211> LENGTH: 19
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (9)..(11)
<223> OTHER INFORMATION: Xaa = (Pro and/or, preferably or, Gly), wherein
      up to two of these positions may be absent

<400> SEQUENCE: 132

Phe Trp Arg Ile Arg Ile Arg Arg Xaa Xaa Xaa Arg Arg Ile Arg Ile
1               5                   10                  15
```

Arg Trp Phe

<210> SEQ ID NO 133
<211> LENGTH: 16
<212> TYPE: PRT
<213> ORGANISM: Artificial Sequence
<220> FEATURE:
<223> OTHER INFORMATION: artificial peptide

<400> SEQUENCE: 133

Phe Trp Arg Arg Phe Trp Arg Arg Phe Trp Arg Arg Phe Trp Arg Arg
1               5                   10                  15

<210> SEQ ID NO 134
<211> LENGTH: 17
<212> TYPE: PRT
<213> ORGANISM: Artificial Sequence
<220> FEATURE:
<223> OTHER INFORMATION: artificial peptide
<220> FEATURE:
<221> NAME/KEY: misc_feature
<222> LOCATION: (9)..(9)
<223> OTHER INFORMATION: Xaa can be any naturally occurring amino acid

<400> SEQUENCE: 134

Phe Trp Arg Arg Phe Trp Arg Arg Xaa Phe Trp Arg Arg Phe Trp Arg
1               5                   10                  15

Arg

<210> SEQ ID NO 135
<211> LENGTH: 16
<212> TYPE: PRT
<213> ORGANISM: Artificial Sequence
<220> FEATURE:
<223> OTHER INFORMATION: artificial peptide

<400> SEQUENCE: 135

Phe Trp Arg Arg Phe Trp Arg Arg Arg Arg Trp Phe Arg Arg Trp Phe
1               5                   10                  15

<210> SEQ ID NO 136
<211> LENGTH: 19
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (9)..(11)
<223> OTHER INFORMATION: Xaa = (Pro and/or, preferably or, Gly), wherein
      up to two of these positions may be absent

<400> SEQUENCE: 136

Phe Trp Arg Arg Phe Trp Arg Arg Xaa Xaa Xaa Arg Arg Trp Phe Arg
1               5                   10                  15

Arg Trp Phe

<210> SEQ ID NO 137
<211> LENGTH: 20
<212> TYPE: PRT
<213> ORGANISM: Artificial Sequence
<220> FEATURE:
<223> OTHER INFORMATION: artificial peptide

<400> SEQUENCE: 137

Pro Phe Trp Arg Ile Arg Ile Arg Arg Asp Pro Phe Trp Arg Ile Arg
1               5                   10                  15

```
Ile Arg Arg Asp
            20

<210> SEQ ID NO 138
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 138

Pro Phe Trp Arg Ile Arg Ile Arg Arg Asp Xaa Xaa Xaa Pro Phe Trp
1               5                   10                  15

Arg Ile Arg Ile Arg Arg Asp
            20

<210> SEQ ID NO 139
<211> LENGTH: 20
<212> TYPE: PRT
<213> ORGANISM: Artificial Sequence
<220> FEATURE:
<223> OTHER INFORMATION: artificial peptide

<400> SEQUENCE: 139

Pro Phe Trp Arg Ile Arg Ile Arg Arg Asp Asp Arg Arg Ile Arg Ile
1               5                   10                  15

Arg Trp Phe Pro
            20

<210> SEQ ID NO 140
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 140

Pro Phe Trp Arg Ile Arg Ile Arg Arg Asp Xaa Xaa Xaa Asp Arg Arg
1               5                   10                  15

Ile Arg Ile Arg Trp Phe Pro
            20

<210> SEQ ID NO 141
<211> LENGTH: 20
<212> TYPE: PRT
<213> ORGANISM: Artificial Sequence
<220> FEATURE:
<223> OTHER INFORMATION: artificial peptide

<400> SEQUENCE: 141

Pro Phe Phe Trp Arg Ile Arg Ile Arg Pro Phe Phe Trp Arg Ile
1               5                   10                  15

Arg Ile Arg Arg
            20
```

```
<210> SEQ ID NO 142
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 142

Pro Phe Phe Trp Arg Ile Arg Ile Arg Xaa Xaa Xaa Pro Phe Phe
1               5                   10                  15

Trp Arg Ile Arg Ile Arg Arg
            20

<210> SEQ ID NO 143
<211> LENGTH: 20
<212> TYPE: PRT
<213> ORGANISM: Artificial Sequence
<220> FEATURE:
<223> OTHER INFORMATION: artificial peptide

<400> SEQUENCE: 143

Pro Phe Phe Trp Arg Ile Arg Ile Arg Arg Arg Ile Arg Ile Arg
1               5                   10                  15

Trp Phe Phe Pro
            20

<210> SEQ ID NO 144
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (11)..(13)
<223> OTHER INFORMATION: Xaa = (Pro and/or, preferably or, Gly), wherein
      up to two of these positions may be absent

<400> SEQUENCE: 144

Pro Phe Phe Trp Arg Ile Arg Ile Arg Xaa Xaa Xaa Arg Arg Ile
1               5                   10                  15

Arg Ile Arg Trp Phe Phe Pro
            20

<210> SEQ ID NO 145
<211> LENGTH: 18
<212> TYPE: PRT
<213> ORGANISM: Artificial Sequence
<220> FEATURE:
<223> OTHER INFORMATION: artificial peptide

<400> SEQUENCE: 145

Pro Phe Trp Arg Gln Arg Ile Arg Arg Pro Phe Trp Arg Gln Arg Ile
1               5                   10                  15

Arg Arg

<210> SEQ ID NO 146
<211> LENGTH: 21
<212> TYPE: PRT
<213> ORGANISM: Artificial Sequence
<220> FEATURE:
<223> OTHER INFORMATION: artificial peptide
```

```
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 146

Pro Phe Trp Arg Gln Arg Ile Arg Arg Xaa Xaa Xaa Pro Phe Trp Arg
1               5                   10                  15

Gln Arg Ile Arg Arg
            20

<210> SEQ ID NO 147
<211> LENGTH: 18
<212> TYPE: PRT
<213> ORGANISM: Artificial Sequence
<220> FEATURE:
<223> OTHER INFORMATION: artificial peptide

<400> SEQUENCE: 147

Pro Phe Trp Arg Gln Arg Ile Arg Arg Arg Ile Arg Gln Arg Trp
1               5                   10                  15

Phe Pro

<210> SEQ ID NO 148
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 148

Pro Phe Trp Arg Gln Arg Ile Arg Arg Xaa Xaa Xaa Arg Arg Ile Arg
1               5                   10                  15

Gln Arg Trp Phe Pro
            20

<210> SEQ ID NO 149
<211> LENGTH: 18
<212> TYPE: PRT
<213> ORGANISM: Artificial Sequence
<220> FEATURE:
<223> OTHER INFORMATION: artificial peptide

<400> SEQUENCE: 149

Pro Phe Trp Arg Arg Gln Ile Arg Arg Pro Phe Trp Arg Arg Gln Ile
1               5                   10                  15

Arg Arg

<210> SEQ ID NO 150
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 150
```

```
Pro Phe Trp Arg Arg Gln Ile Arg Arg Xaa Xaa Xaa Pro Phe Trp Arg
1               5                   10                  15

Arg Gln Ile Arg Arg
            20

<210> SEQ ID NO 151
<211> LENGTH: 18
<212> TYPE: PRT
<213> ORGANISM: Artificial Sequence
<220> FEATURE:
<223> OTHER INFORMATION: artificial peptide

<400> SEQUENCE: 151

Pro Phe Trp Arg Arg Gln Ile Arg Arg Arg Arg Ile Gln Arg Arg Trp
1               5                   10                  15

Phe Pro

<210> SEQ ID NO 152
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 152

Pro Phe Trp Arg Arg Gln Ile Arg Arg Xaa Xaa Xaa Arg Arg Ile Gln
1               5                   10                  15

Arg Arg Trp Phe Pro
            20

<210> SEQ ID NO 153
<211> LENGTH: 18
<212> TYPE: PRT
<213> ORGANISM: Artificial Sequence
<220> FEATURE:
<223> OTHER INFORMATION: artificial peptide

<400> SEQUENCE: 153

Pro Phe Trp Arg Ala Arg Ile Arg Arg Pro Phe Trp Arg Ala Arg Ile
1               5                   10                  15

Arg Arg

<210> SEQ ID NO 154
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 154

Pro Phe Trp Arg Ala Arg Ile Arg Arg Xaa Xaa Xaa Pro Phe Trp Arg
1               5                   10                  15

Ala Arg Ile Arg Arg
            20
```

<210> SEQ ID NO 155
<211> LENGTH: 18
<212> TYPE: PRT
<213> ORGANISM: Artificial Sequence
<220> FEATURE:
<223> OTHER INFORMATION: artificial peptide

<400> SEQUENCE: 155

Pro Phe Trp Arg Ala Arg Ile Arg Arg Arg Arg Ile Arg Ala Arg Trp
1               5                   10                  15

Phe Pro

<210> SEQ ID NO 156
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 156

Pro Phe Trp Arg Ala Arg Ile Arg Arg Xaa Xaa Xaa Arg Arg Ile Arg
1               5                   10                  15

Ala Arg Trp Phe Pro
            20

<210> SEQ ID NO 157
<211> LENGTH: 18
<212> TYPE: PRT
<213> ORGANISM: Artificial Sequence
<220> FEATURE:
<223> OTHER INFORMATION: artificial peptide

<400> SEQUENCE: 157

Pro Phe Trp Arg Lys Arg Ile Arg Arg Pro Phe Trp Arg Lys Arg Ile
1               5                   10                  15

Arg Arg

<210> SEQ ID NO 158
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 158

Pro Phe Trp Arg Lys Arg Ile Arg Arg Xaa Xaa Xaa Pro Phe Trp Arg
1               5                   10                  15

Lys Arg Ile Arg Arg
            20

<210> SEQ ID NO 159
<211> LENGTH: 18
<212> TYPE: PRT
<213> ORGANISM: Artificial Sequence
<220> FEATURE:
<223> OTHER INFORMATION: artificial peptide

<400> SEQUENCE: 159

Pro Phe Trp Arg Lys Arg Ile Arg Arg Arg Arg Ile Arg Lys Arg Trp
1               5                   10                  15

Phe Pro

<210> SEQ ID NO 160
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 160

Pro Phe Trp Arg Lys Arg Ile Arg Arg Xaa Xaa Xaa Arg Arg Ile Arg
1               5                   10                  15

Lys Arg Trp Phe Pro
            20

<210> SEQ ID NO 161
<211> LENGTH: 18
<212> TYPE: PRT
<213> ORGANISM: Artificial Sequence
<220> FEATURE:
<223> OTHER INFORMATION: artificial peptide

<400> SEQUENCE: 161

Pro Phe Trp Arg Lys Arg Leu Arg Arg Pro Phe Trp Arg Lys Arg Leu
1               5                   10                  15

Arg Arg

<210> SEQ ID NO 162
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 162

Pro Phe Trp Arg Lys Arg Leu Arg Arg Xaa Xaa Xaa Pro Phe Trp Arg
1               5                   10                  15

Lys Arg Leu Arg Arg
            20

<210> SEQ ID NO 163
<211> LENGTH: 18
<212> TYPE: PRT
<213> ORGANISM: Artificial Sequence
<220> FEATURE:
<223> OTHER INFORMATION: artificial peptide

<400> SEQUENCE: 163

Pro Phe Trp Arg Lys Arg Leu Arg Arg Arg Arg Leu Arg Lys Arg Trp
1               5                   10                  15

Phe Pro

<210> SEQ ID NO 164
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 164

Pro Phe Trp Arg Lys Arg Leu Arg Arg Xaa Xaa Xaa Arg Arg Leu Arg
1               5                   10                  15

Lys Arg Trp Phe Pro
            20

<210> SEQ ID NO 165
<211> LENGTH: 18
<212> TYPE: PRT
<213> ORGANISM: Artificial Sequence
<220> FEATURE:
<223> OTHER INFORMATION: artificial peptide

<400> SEQUENCE: 165

Pro Phe Trp Arg Lys Lys Leu Lys Arg Pro Phe Trp Arg Lys Lys Leu
1               5                   10                  15

Lys Arg

<210> SEQ ID NO 166
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 166

Pro Phe Trp Arg Lys Lys Leu Lys Arg Xaa Xaa Xaa Pro Phe Trp Arg
1               5                   10                  15

Lys Lys Leu Lys Arg
            20

<210> SEQ ID NO 167
<211> LENGTH: 18
<212> TYPE: PRT
<213> ORGANISM: Artificial Sequence
<220> FEATURE:
<223> OTHER INFORMATION: artificial peptide

<400> SEQUENCE: 167

Pro Phe Trp Arg Lys Lys Leu Lys Arg Lys Leu Lys Lys Arg Trp
1               5                   10                  15

Phe Pro

<210> SEQ ID NO 168
<211> LENGTH: 21
<212> TYPE: PRT
<213> ORGANISM: Artificial Sequence
<220> FEATURE:

```
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 168

Pro Phe Trp Arg Lys Lys Leu Lys Arg Xaa Xaa Xaa Arg Lys Leu Lys
1               5                   10                  15

Lys Arg Trp Phe Pro
            20

<210> SEQ ID NO 169
<211> LENGTH: 18
<212> TYPE: PRT
<213> ORGANISM: Artificial Sequence
<220> FEATURE:
<223> OTHER INFORMATION: artificial peptide

<400> SEQUENCE: 169

Pro Phe Trp Arg Lys Arg Trp Arg Arg Pro Phe Trp Arg Lys Arg Trp
1               5                   10                  15

Arg Arg

<210> SEQ ID NO 170
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 170

Pro Phe Trp Arg Lys Arg Trp Arg Arg Xaa Xaa Xaa Pro Phe Trp Arg
1               5                   10                  15

Lys Arg Trp Arg Arg
            20

<210> SEQ ID NO 171
<211> LENGTH: 18
<212> TYPE: PRT
<213> ORGANISM: Artificial Sequence
<220> FEATURE:
<223> OTHER INFORMATION: artificial peptide

<400> SEQUENCE: 171

Pro Phe Trp Arg Lys Arg Trp Arg Arg Arg Arg Trp Arg Lys Arg Trp
1               5                   10                  15

Phe Pro

<210> SEQ ID NO 172
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent
```

```
<400> SEQUENCE: 172

Pro Phe Trp Arg Lys Arg Trp Arg Arg Xaa Xaa Xaa Arg Arg Trp Arg
1               5                   10                  15

Lys Arg Trp Phe Pro
            20

<210> SEQ ID NO 173
<211> LENGTH: 18
<212> TYPE: PRT
<213> ORGANISM: Artificial Sequence
<220> FEATURE:
<223> OTHER INFORMATION: artificial peptide

<400> SEQUENCE: 173

Pro Phe Trp Arg Arg Arg Ile Arg Arg Pro Phe Trp Arg Arg Arg Ile
1               5                   10                  15

Arg Arg

<210> SEQ ID NO 174
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 174

Pro Phe Trp Arg Arg Arg Ile Arg Arg Xaa Xaa Xaa Pro Phe Trp Arg
1               5                   10                  15

Arg Arg Ile Arg Arg
            20

<210> SEQ ID NO 175
<211> LENGTH: 18
<212> TYPE: PRT
<213> ORGANISM: Artificial Sequence
<220> FEATURE:
<223> OTHER INFORMATION: artificial peptide

<400> SEQUENCE: 175

Pro Phe Trp Arg Arg Arg Ile Arg Arg Arg Arg Ile Arg Arg Arg Trp
1               5                   10                  15

Phe Pro

<210> SEQ ID NO 176
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 176

Pro Phe Trp Arg Arg Arg Ile Arg Arg Xaa Xaa Xaa Arg Arg Ile Arg
1               5                   10                  15

Arg Arg Trp Phe Pro
            20
```

<210> SEQ ID NO 177
<211> LENGTH: 18
<212> TYPE: PRT
<213> ORGANISM: Artificial Sequence
<220> FEATURE:
<223> OTHER INFORMATION: artificial peptide

<400> SEQUENCE: 177

Pro Phe Trp Arg Arg Arg Trp Arg Arg Pro Phe Trp Arg Arg Arg Trp
1               5                   10                  15

Arg Arg

<210> SEQ ID NO 178
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 178

Pro Phe Trp Arg Arg Arg Trp Arg Arg Xaa Xaa Xaa Pro Phe Trp Arg
1               5                   10                  15

Arg Arg Trp Arg Arg
            20

<210> SEQ ID NO 179
<211> LENGTH: 18
<212> TYPE: PRT
<213> ORGANISM: Artificial Sequence
<220> FEATURE:
<223> OTHER INFORMATION: artificial peptide

<400> SEQUENCE: 179

Pro Phe Trp Arg Arg Arg Trp Arg Arg Arg Arg Trp Arg Arg Arg Trp
1               5                   10                  15

Phe Pro

<210> SEQ ID NO 180
<211> LENGTH: 21
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (10)..(12)
<223> OTHER INFORMATION: Xaa = (Pro and/or, preferably or, Gly), wherein
      up to two of these positions may be absent

<400> SEQUENCE: 180

Pro Phe Trp Arg Arg Arg Trp Arg Arg Xaa Xaa Xaa Arg Arg Trp Arg
1               5                   10                  15

Arg Arg Trp Phe Pro
            20

<210> SEQ ID NO 181
<211> LENGTH: 16
<212> TYPE: PRT
<213> ORGANISM: Artificial Sequence
<220> FEATURE:

<223> OTHER INFORMATION: artificial peptide

<400> SEQUENCE: 181

Pro Trp Arg Ile Arg Ile Arg Arg Pro Trp Arg Ile Arg Ile Arg Arg
1               5                   10                  15

<210> SEQ ID NO 182
<211> LENGTH: 19
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (9)..(11)
<223> OTHER INFORMATION: Xaa = (Pro and/or, preferably or, Gly), wherein
      up to two of these positions may be absent

<400> SEQUENCE: 182

Pro Trp Arg Ile Arg Ile Arg Arg Xaa Xaa Xaa Pro Trp Arg Ile Arg
1               5                   10                  15

Ile Arg Arg

<210> SEQ ID NO 183
<211> LENGTH: 16
<212> TYPE: PRT
<213> ORGANISM: Artificial Sequence
<220> FEATURE:
<223> OTHER INFORMATION: artificial peptide

<400> SEQUENCE: 183

Pro Trp Arg Ile Arg Ile Arg Arg Arg Ile Arg Ile Arg Trp Pro
1               5                   10                  15

<210> SEQ ID NO 184
<211> LENGTH: 19
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (9)..(11)
<223> OTHER INFORMATION: Xaa = (Pro and/or, preferably or, Gly), wherein
      up to two of these positions may be absent

<400> SEQUENCE: 184

Pro Trp Arg Ile Arg Ile Arg Arg Xaa Xaa Xaa Arg Arg Ile Arg Ile
1               5                   10                  15

Arg Trp Pro

<210> SEQ ID NO 185
<211> LENGTH: 14
<212> TYPE: PRT
<213> ORGANISM: Artificial Sequence
<220> FEATURE:
<223> OTHER INFORMATION: artificial peptide

<400> SEQUENCE: 185

Pro Trp Arg Arg Ile Arg Arg Pro Trp Arg Arg Ile Arg Arg
1               5                   10

<210> SEQ ID NO 186
<211> LENGTH: 17
<212> TYPE: PRT
<213> ORGANISM: Artificial Sequence
<220> FEATURE:

```
<223> OTHER INFORMATION: artificial peptide
<220> FEATURE:
<221> NAME/KEY: MISC_FEATURE
<222> LOCATION: (8)..(10)
<223> OTHER INFORMATION: Xaa = (Pro and/or, preferably or, Gly), wherein
      up to two of these positions may be absent

<400> SEQUENCE: 186

Pro Trp Arg Arg Ile Arg Arg Xaa Xaa Xaa Pro Trp Arg Arg Ile Arg
1               5                  10                  15

Arg

<210> SEQ ID NO 187
<211> LENGTH: 14
<212> TYPE: PRT
<213> ORGANISM: Artificial Sequence
<220> FEATURE:
<223> OTHER INFORMATION: artificial peptide

<400> SEQUENCE: 187

Pro Trp Arg Arg Ile Arg Arg Arg Ile Arg Arg Trp Pro
1               5                  10

<210> SEQ ID NO 188
<211> LENGTH: 17
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (8)..(10)
<223> OTHER INFORMATION: Xaa = (Pro and/or, preferably or, Gly), wherein
      up to two of these positions may be absent

<400> SEQUENCE: 188

Pro Trp Arg Arg Ile Arg Arg Xaa Xaa Xaa Arg Arg Ile Arg Arg Trp
1               5                  10                  15

Pro

<210> SEQ ID NO 189
<211> LENGTH: 16
<212> TYPE: PRT
<213> ORGANISM: Artificial Sequence
<220> FEATURE:
<223> OTHER INFORMATION: artificial peptide

<400> SEQUENCE: 189

Pro Trp Arg Arg Lys Ile Arg Arg Pro Trp Arg Arg Lys Ile Arg Arg
1               5                  10                  15

<210> SEQ ID NO 190
<211> LENGTH: 19
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (9)..(11)
<223> OTHER INFORMATION: Xaa = (Pro and/or, preferably or, Gly), wherein
      up to two of these positions may be absent

<400> SEQUENCE: 190

Pro Trp Arg Arg Lys Ile Arg Arg Xaa Xaa Xaa Pro Trp Arg Arg Lys
1               5                  10                  15

Ile Arg Arg
```

<210> SEQ ID NO 191
<211> LENGTH: 16
<212> TYPE: PRT
<213> ORGANISM: Artificial Sequence
<220> FEATURE:
<223> OTHER INFORMATION: artificial peptide

<400> SEQUENCE: 191

Pro Trp Arg Arg Lys Ile Arg Arg Arg Ile Lys Arg Arg Trp Pro
1               5                   10                  15

<210> SEQ ID NO 192
<211> LENGTH: 19
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (9)..(11)
<223> OTHER INFORMATION: Xaa = (Pro and/or, preferably or, Gly), wherein
      up to two of these positions may be absent

<400> SEQUENCE: 192

Pro Trp Arg Arg Lys Ile Arg Arg Xaa Xaa Xaa Arg Arg Ile Lys Arg
1               5                   10                  15

Arg Trp Pro

<210> SEQ ID NO 193
<211> LENGTH: 11
<212> TYPE: PRT
<213> ORGANISM: Artificial Sequence
<220> FEATURE:
<223> OTHER INFORMATION: artificial peptide

<400> SEQUENCE: 193

Pro Phe Trp Arg Arg Arg Ile Arg Ile Arg Arg
1               5                   10

<210> SEQ ID NO 194
<211> LENGTH: 22
<212> TYPE: PRT
<213> ORGANISM: Artificial Sequence
<220> FEATURE:
<223> OTHER INFORMATION: artificial peptide

<400> SEQUENCE: 194

Pro Phe Trp Arg Arg Arg Ile Arg Ile Arg Arg Pro Phe Trp Arg Arg
1               5                   10                  15

Arg Ile Arg Ile Arg Arg
            20

<210> SEQ ID NO 195
<211> LENGTH: 25
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (12)..(14)
<223> OTHER INFORMATION: Xaa = (Pro and/or, preferably or, Gly), wherein
      up to two of these positions may be absent

<400> SEQUENCE: 195

Pro Phe Trp Arg Arg Arg Ile Arg Ile Arg Arg Xaa Xaa Xaa Pro Phe

```
                 1               5                  10                 15
Trp Arg Arg Arg Ile Arg Ile Arg Arg
                 20                 25

<210> SEQ ID NO 196
<211> LENGTH: 22
<212> TYPE: PRT
<213> ORGANISM: Artificial Sequence
<220> FEATURE:
<223> OTHER INFORMATION: artificial peptide

<400> SEQUENCE: 196

Pro Phe Trp Arg Arg Arg Ile Arg Ile Arg Arg Arg Arg Ile Arg Ile
1               5                   10                  15

Arg Arg Arg Trp Phe Pro
            20

<210> SEQ ID NO 197
<211> LENGTH: 25
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (12)..(14)
<223> OTHER INFORMATION: Xaa = (Pro and/or, preferably or, Gly), wherein
      up to two of these positions may be absent

<400> SEQUENCE: 197

Arg Arg Ile Arg Ile Arg Arg Arg Trp Phe Pro Xaa Xaa Xaa Arg Arg
1               5                   10                  15

Ile Arg Ile Arg Arg Arg Trp Phe Pro
            20                  25

<210> SEQ ID NO 198
<211> LENGTH: 8
<212> TYPE: PRT
<213> ORGANISM: Artificial Sequence
<220> FEATURE:
<223> OTHER INFORMATION: artificial peptide

<400> SEQUENCE: 198

Arg Arg Trp Phe Phe Trp Arg Arg
1               5

<210> SEQ ID NO 199
<211> LENGTH: 16
<212> TYPE: PRT
<213> ORGANISM: Artificial Sequence
<220> FEATURE:
<223> OTHER INFORMATION: artificial peptide

<400> SEQUENCE: 199

Arg Arg Trp Phe Phe Trp Arg Arg Arg Arg Trp Phe Phe Trp Arg Arg
1               5                   10                  15

<210> SEQ ID NO 200
<211> LENGTH: 19
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (9)..(11)
<223> OTHER INFORMATION: Xaa = (Pro and/or, preferably or, Gly), wherein
``` up to two of these positions may be absent

<400> SEQUENCE: 200

Arg Arg Trp Phe Phe Trp Arg Arg Xaa Xaa Xaa Arg Arg Trp Phe Phe
1               5                   10                  15

Trp Arg Arg

<210> SEQ ID NO 201
<211> LENGTH: 14
<212> TYPE: PRT
<213> ORGANISM: Artificial Sequence
<220> FEATURE:
<223> OTHER INFORMATION: artificial peptide

<400> SEQUENCE: 201

Arg Arg Trp Phe Trp Arg Arg Arg Arg Trp Phe Trp Arg Arg
1               5                   10

<210> SEQ ID NO 202
<211> LENGTH: 17
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (8)..(10)
<223> OTHER INFORMATION: Xaa = (Pro and/or, preferably or, Gly), wherein
      up to two of these positions may be absent

<400> SEQUENCE: 202

Arg Arg Trp Phe Trp Arg Arg Xaa Xaa Xaa Arg Arg Trp Phe Trp Arg
1               5                   10                  15

Arg

<210> SEQ ID NO 203
<211> LENGTH: 7
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (1)..(1)
<223> OTHER INFORMATION: Xaa are one or two hydrophobic amino acids,
      preferably selected from the group consisting of phenylalanine
      (Phe), alanine (Ala), leucine (Leu) and valine (Val)
<220> FEATURE:
<221> NAME/KEY: MISC_FEATURE
<222> LOCATION: (2)..(2)
<223> OTHER INFORMATION: Xaa is a hydrophobic amino acid, preferably
      tryptophan (Trp)
<220> FEATURE:
<221> NAME/KEY: MISC_FEATURE
<222> LOCATION: (3)..(3)
<223> OTHER INFORMATION: Xaa are two or thre amino acids selected from
      the group consisting of alanine (Ala), arginine (Arg), glutamine
      (Gln), asparagine (Asn), proline (Pro), isoleucine (Ile), leucine
      (Leu) and valine (Val)
<220> FEATURE:
<221> NAME/KEY: MISC_FEATURE
<222> LOCATION: (4)..(4)
<223> OTHER INFORMATION: Xaa is selected from the group consisting of
      isoleucine (Ile), phenylalanine (Phe), tryptophan (Trp) and
      tyrosine (Tyr)
<220> FEATURE:
<221> NAME/KEY: MISC_FEATURE
<222> LOCATION: (5)..(5)
<223> OTHER INFORMATION: Xaa are one or two amino acids selected from
      the group consisting of arginine (Arg), lysine (Lys), tyrosine
      (Tyr) and phenylalanine (Phe)

```
<220> FEATURE:
<221> NAME/KEY: MISC_FEATURE
<222> LOCATION: (6)..(6)
<223> OTHER INFORMATION: Xaa is a hydrophobic amino acid, preferably
      selected from the group consisting of isoleucine (Ile), tryptophan
      (Trp), valine (Val) and leucine (Leu)
<220> FEATURE:
<221> NAME/KEY: MISC_FEATURE
<222> LOCATION: (7)..(7)
<223> OTHER INFORMATION: Xaa are 1, 2, 3 or 4  (Xaa is 1 under the
      proviso that if Xaa at position 5 is Arg-Arg) amino acids selected
      from the group consisting of arginine (Arg), lysine (Lys),
      isoleucine (Ile) and serine (Ser)

<400> SEQUENCE: 203

Xaa Xaa Xaa Xaa Xaa Xaa Xaa
1               5

<210> SEQ ID NO 204
<211> LENGTH: 7
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (1)..(1)
<223> OTHER INFORMATION: Xaa are one or two hydrophobic amino acids,
      preferably selected from the group consisting of phenylalanine
      (Phe) and isoleucine (Ile)
<220> FEATURE:
<221> NAME/KEY: MISC_FEATURE
<222> LOCATION: (2)..(2)
<223> OTHER INFORMATION: Xaa is a hydrophobic amino acid, preferably
      tryptophan (Trp)
<220> FEATURE:
<221> NAME/KEY: MISC_FEATURE
<222> LOCATION: (3)..(3)
<223> OTHER INFORMATION: Xaa are 1, 2 or 3 amino acids selected from the
      group consisting of glycine (Gly), asparagine (Asn), isoleucine
      (Ile) and phenylalanin (Phe)
<220> FEATURE:
<221> NAME/KEY: MISC_FEATURE
<222> LOCATION: (4)..(4)
<223> OTHER INFORMATION: Xaa is isoleucine (Ile) or tryptophan (Trp)
<220> FEATURE:
<221> NAME/KEY: MISC_FEATURE
<222> LOCATION: (5)..(5)
<223> OTHER INFORMATION: Xaa are one or two amino acids selected from
      the group consisting of arginine (Arg) or lysine (Lys)
<220> FEATURE:
<221> NAME/KEY: MISC_FEATURE
<222> LOCATION: (6)..(6)
<223> OTHER INFORMATION: Xaa is a hydrophobic amino acid, preferably
      selected from the group consisting of isoleucine (Ile), tryptophan
      (Trp) and valine (Val) or no amino acid residue
<220> FEATURE:
<221> NAME/KEY: MISC_FEATURE
<222> LOCATION: (7)..(7)
<223> OTHER INFORMATION: Xaa are one or two arginine (Arg) residues or
      no amino acid residue

<400> SEQUENCE: 204

Xaa Xaa Xaa Xaa Xaa Xaa Xaa
1               5

<210> SEQ ID NO 205
<211> LENGTH: 6
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (1)..(1)
```

```
<223> OTHER INFORMATION: Xaa are one or two or three hydrophobic amino
      acids, preferably selected from the group consisting of proline
      (Pro) and phenylalanine (Phe) or no amino acid residue
<220> FEATURE:
<221> NAME/KEY: MISC_FEATURE
<222> LOCATION: (2)..(2)
<223> OTHER INFORMATION: Xaa is a hydrophobic amino acid, preferably
      tryptophan (Trp)
<220> FEATURE:
<221> NAME/KEY: MISC_FEATURE
<222> LOCATION: (3)..(3)
<223> OTHER INFORMATION: Xaa are one or two or three hydrophobic amino
      acids selected from the group consisting of alanine (Ala),
      arginine (Arg), glutamine (Gln), lysine (Lys), tryptophan (Trp)
      and isoleucine (Ile)
<220> FEATURE:
<221> NAME/KEY: MISC_FEATURE
<222> LOCATION: (4)..(4)
<223> OTHER INFORMATION: Xaa are one or two or three hydrophobic amino
      acids selected from the group consisting of arginine (Arg) and
      aspartate (Asp) or no amino acid residue
<220> FEATURE:
<221> NAME/KEY: MISC_FEATURE
<222> LOCATION: (5)..(5)
<223> OTHER INFORMATION: Xaa are one or two hydrophobic amino acids,
      preferably selected from the group consisting of isoleucine (Ile),
      tryptophan (Trp), phenylalanine (Phe), valine (Val) and leucine
      (Leu)
<220> FEATURE:
<221> NAME/KEY: MISC_FEATURE
<222> LOCATION: (6)..(6)
<223> OTHER INFORMATION: Xaa are one or two or three amino acids
      selected from the group consisting of arginine (Arg), lysine
      (Lys), isoleucine (Ile), serine (Ser) and aspartate (Asp)

<400> SEQUENCE: 205

Xaa Xaa Xaa Xaa Xaa Xaa
1               5

<210> SEQ ID NO 206
<211> LENGTH: 8
<212> TYPE: PRT
<213> ORGANISM: Artificial Sequence
<220> FEATURE:
<223> OTHER INFORMATION: artificial peptide
<220> FEATURE:
<221> NAME/KEY: MISC_FEATURE
<222> LOCATION: (1)..(1)
<223> OTHER INFORMATION: Xaa are one or two or three hydrophobic amino
      acids, preferably selected from the group consisting of proline
      (Pro) and phenylalanine (Phe) or no amino acid residue
<220> FEATURE:
<221> NAME/KEY: MISC_FEATURE
<222> LOCATION: (2)..(2)
<223> OTHER INFORMATION: Xaa is a basic amino acid, preferably arginine
      (Arg), or no amino acid residue
<220> FEATURE:
<221> NAME/KEY: MISC_FEATURE
<222> LOCATION: (3)..(3)
<223> OTHER INFORMATION: Xaa is a hydrophobic amino acid, preferably
      tryptophan (Trp)
<220> FEATURE:
<221> NAME/KEY: MISC_FEATURE
<222> LOCATION: (4)..(4)
<223> OTHER INFORMATION: Xaa are one or two or three amino acids
      selected from the group consisting of alanine (Ala), arginine
      (Arg), glutamine (Gln), asparagine (Asn) and lysine (Lys)
<220> FEATURE:
<221> NAME/KEY: MISC_FEATURE
<222> LOCATION: (5)..(5)
<223> OTHER INFORMATION: Xaa are one or two amino acids selected from
      the group consisting of isoleucine (Ile), phenylalanine (Phe) and
      tryptophan (Trp)
<220> FEATURE:
<221> NAME/KEY: MISC_FEATURE
<222> LOCATION: (6)..(6)
<223> OTHER INFORMATION: Xaa are one or two or three amino acids
```

```
        selected from the group consisting of glutamine (Gln), arginine
        (Arg) and asparagine (Asn) or no amino acid residue
<220> FEATURE:
<221> NAME/KEY: MISC_FEATURE
<222> LOCATION: (7)..(7)
<223> OTHER INFORMATION: Xaa are one or two hydrophobic amino acids,
        preferably selected from the group consisting of isoleucine (Ile),
        tryptophan (Trp) and phe-nylalanine (Phe), or no amino acid
        residue
<220> FEATURE:
<221> NAME/KEY: MISC_FEATURE
<222> LOCATION: (8)..(8)
<223> OTHER INFORMATION: Xaa are one or two arginine residues or no
        amino acid residue

<400> SEQUENCE: 206

Xaa Xaa Xaa Xaa Xaa Xaa Xaa Xaa
1               5

<210> SEQ ID NO 207
<211> LENGTH: 25
<212> TYPE: PRT
<213> ORGANISM: Homo sapiens

<400> SEQUENCE: 207

Thr Lys Cys Phe Gln Trp Gln Arg Asn Met Arg Lys Val Arg Gly Pro
1               5                   10                  15

Pro Val Ser Cys Ile Lys Arg Asp Ser
            20                  25
```

PEPTIDES FOR THE TREATMENT OF CANCER

CROSS-REFERENCE TO RELATED APPLICATIONS

This application is a national phase application under 35 U.S.C. §371 of International Application No. PCT/EP2014/050330 filed 9 Jan. 2014, which claims priority to European Patent Application No. 13150974.7 filed 11 Jan. 2013. The entire contents of each of the above-referenced disclosures is specifically incorporated by reference herein without disclaimer.

The present invention relates to an isolated peptide exhibiting antitumoral effects.

Every year millions of people are diagnosed with cancer worldwide. Notwithstanding in the last decades much progress has been achieved in cancer therapy, nevertheless cancer remains a leading cause of death. Nowadays, surgery, chemotherapy, radiation, hormone ablation therapy and targeted therapy are the standard treatments, but in the year 2008 these were not curative in more than 50% of the cases. Furthermore, the use of these types of therapy is limited due to resistance and is accompanied by potential toxicity and diverse side effects due to inadequate specificity for tumor cells. Obviously, the discovery of new and more specific targets, together with the design of specific antitumor drugs, is one of the major interests in cancer research.

Cancer cells are often well characterized, but little is known about the plasma cell membrane, or to be more precise, the arising differences in the lipid composition in carcinogenesis. Eukaryotic plasma membranes usually comprise an overall neutral charge on the outer leaflet due to the zwitterionic phosphatidylcholine (PC) and sphingomyelin (SM). The negatively charged phospholipid phosphatidylserine (PS) together with the major part of phosphatidylethanolamine (PE) normally only assembles in the inner leaflet of eukaryotic plasma membranes. This asymmetric distribution of phospholipids is well documented and is maintained by an ATP-dependent aminophospholipid translocase. This asymmetry can get lost due to exposure of the negatively charged phosphatidylserine on the surface of cancerous and other pathological cells, apoptotic cells, as well as platelets and erythrocytes upon activation.

Based on the knowledge of PS exposure, new strategies for the design of anticancer drugs can be considered, especially cationic host defense derived peptides interacting with negatively charged phospholipids. Host defense peptides have emerged as potential alternative anticancer therapeutics offering many advantages over other therapies (Mader et al., Exp. Op. Investig. Drugs 15 (2006), 933-946). Because of their mode of action and specificity—the cell membrane being the major target—resistance and cytotoxicity are less likely to occur and thus, they are also expected to cause fewer side effects. Furthermore, these peptides mostly damage cell membranes within minutes, which would hinder formation of resistance. Host defense peptides being part of the innate immune system of many diverse species (e.g. mammals, insects, amphibians) were initially discovered because of their antimicrobial activity. Currently, the antimicrobial peptide database lists more than 100 natural host defense peptides with antitumor activity. Examples for antimicrobial peptides are disclosed in WO 2008/002165 A1.

One prominent member of anticancer peptides is bovine lactoferricin (bLFcin), which is generated from lactoferrin through pepsin cleavage. bLFcin possesses an acyclic twisted antiparallel β-sheet structure due to a disulfide bridge between two cysteine residues. This peptide is able to inhibit liver and lung metastasis in mice. In vivo studies with bLFcin on fibrosarcoma, melanoma and colon carcinoma tumors revealed massive necrosis of the tumor tissue after exposure to the peptide (Yoo et al. Jpn. J Cancer Res. 88 (1997): 184-190). Furthermore, it is known that bLFcin inhibits the tumor growth of neuroblastoma xenografts in nude rats. Clarification of the mechanism revealed that bLFcin induces apoptosis in human tumor cells through a pathway mediated by production of the intracellular ROS and activation of $Ca^{2+}/Mg^{2+}$-dependent endonucleases.

It is an object of the present invention to provide compounds and preparations which can be used to treat cancer.

Therefore the present invention relates to an isolated peptide to be used in the treatment of cancer consisting of 12 to 50 amino acid residues comprising at least two beta-strands, or
at least two alpha-helices or
at least one beta-strand and at least one alpha-helix, wherein said beta-strands and/or alpha-helices are preferably separated from each other by at least one turn, wherein the peptide has a net positive charge of +7 or more;

wherein said peptide comprises at least one peptide moiety having amino acid sequence $(X_1)_M$-$X_2$-$(X_3)_P$-$X_4$-$(X_5)_Q$-$X_6$-$(X_7)_S$ or the reverse sequence thereof, wherein $X_1$ is a hydrophobic amino acid, preferably selected from the group consisting of phenylalanine (Phe), alanine (Ala), leucine (Leu) and valine (Val), $X_2$ is a hydrophobic amino acid, preferably tryptophan (Trp), $X_3$ is selected from the group consisting of alanine (Ala), arginine (Arg), glutamine (Gln), asparagine (Asn), proline (Pro), isoleucine (Ile), leucine (Leu) and valine (Val), $X_4$ is selected from the group consisting of isoleucine (Ile), phenylalanine (Phe), tryptophan (Trp) and tyrosine (Tyr), $X_5$ is selected from the group consisting of arginine (Arg), lysine (Lys), tyrosine (Tyr) and phenylalanine (Phe), $X_6$ is a hydrophobic amino acid, preferably selected from the group consisting of isoleucine (Ile), tryptophan (Trp), valine (Val) and leucine (Leu), and $X_7$ is selected from the group consisting of arginine (Arg), lysine (Lys), isoleucine (Ile) and serine (Ser), and wherein M is 1 or 2,
Q is 1 or 2,
P is 2 or 3, and
S is 1, 2, 3 or 4 under the proviso that if $(X_5)_Q$ is Arg-Arg S is 1; and wherein said peptide is devoid of intramolecular disulfide bonds, preferably, said peptide being selected from the group consisting of PFWRIRIRRXRRIRIRWFP (SEQ ID. No. 128), PWRIRIRRXRRIRIRWP (SEQ ID No. 184), RWKRIN-RQWFFWQRNIRKWR (SEQ ID. No. 106), PFWRIRIR-RPFWRIRIRR (SEQ ID. No. 125), PFFWRIRIRRPFF-WRIRIRR (SEQ ID. No. 141) and PFWRIRIRRRRIRIRWFP (SEQ ID. No. 127), especially SEQ ID. Nos. 128, 184 and 106, wherein "X" is proline (Pro) and/or glycine $(Gly)_{1-3}$.

It turned out that peptides having a net positive charge of +7 and comprising at least two beta-strands or at least two alpha-helices or at least one beta-strand and at least one alpha-helix and are preferably separated by at least one turn exhibit cytotoxic effects on cancerous/tumor cells in mammals. This means that the peptides of the present invention are able to affect the viability of such cells leading to their destruction. The cytotoxic effects of the peptides of the present invention are highly specific for cancerous/tumor cells. This means that these peptides affect healthy cells to a much lower extent (preferably to at least 10%, more preferably to at least 20%, even more preferably to at least 50%, in particular at least 90 to 100%) compared to cancerous/tumor cells. This high specificity of the peptides of the present invention allows treating mammals, in particular humans, with a much higher efficacy reducing commonly known side-effects regularly described for anti-cancer compounds. The cytotoxic effect of such compounds is usually unspecific resulting in the destruction not only of cancerous/tumor cells but also of healthy cells.

The antitumour properties of the peptides according to the present invention are specifically surprising, because the present peptides are, by their definition, devoid of disulfide bonds, i.e. devoid of intramolecular S—S bonds (due to the absence of (at least) two cysteine residues in the amino acid sequence that form this bond). The molecules of the present invention have been derived from human lactoferricin (hLFcin: TKCFQWQRNMRKVRGPPVSCIKRDS (SEQ ID No. 207)), a peptide that contains two cysteins that form an intramolecular disulfide bond. One of the staring compounds of the developments of the present invention was a part of hLFcin that lacks the cysteins and wherein the methionine has been replaced by isoleucine (FQWQRNIRKVR; SEQ ID NO. 87; "PEP parent"). In contrast to other membrane active peptides, PEP parent therefore was devoid of intramolecular disulfide bonds (and even devoid of cysteine residues) that were thought to be important for membrane active (antimicrobial) function (see e.g. Harwig et al., Eur. J. Biochem. 240 (1996), 352-357). In fact, eliminating the disulfide bonds from such molecules significantly reduced membrane permeabilising activity of such peptides (Matsuzaki et al., Biochemistry 32 (1993), 11704-11710; Tamamura et al., Chem. Pharm. Bull. 43 (5) (1995), 853-858). It was known to a person with average skill in the art that disulfide bonds are of significant importance for membrane active peptides. It was therefore surprising that the peptides according to the present invention that are also membrane active, do not contain intramolecular disulfide bonds. In fact, the preferred peptide moieties which are responsible for the antitumor effect of the peptides according to the present invention are completely free of cysteine residues. The antitumour peptide according to the present invention is therefore usually cysteine-free. Cysteine residues can, however, if necessary, be used to couple the present peptide to other molecules (e.g. to carriers (e.g. carrier proteins)) which are preferably released from the peptides according to the present invention before administration or (after administration) in the body of a patient. In such cases, the disulfide bond is not located within the peptide defined by the present invention but between the peptide according to the present invention (that is defined by a continuous peptide bond connection (amino acid sequence)) and another chemical compound. That the peptides according to the present invention are devoid of intramolecular disulfide bonds is specifically surprising with regard to the fact that the peptides according to the present invention are derived from human lactoferricin (hLFcin) for which the disulfide bond has been disclosed as being essential for the antimicrobial activity and also held relevant for the antitumor activity (Gifford et al., Cell. Mol. Life Sci. 62 (2005), 2588-2598). Also for bovine lactoferricin (LFcinB), the disulfide bond was regarded as necessary for the antitumoral activity (Eliassen et al., Anticancer. Res. 22 (2002), 2703-2710).

This also shows that the antitumor activity of the peptides of the present invention is not dependent on a specifically stabilised (i.e. by disulfide bonds) secondary structure, but that the beta-strand and alpha-helix folding is sufficient for the peptides defined e.g. by the consensus sequences of the peptide moieties present in the peptide according to the present invention.

Preferably, the isolated peptides according to the present invention contain at least one turn. A "turn" is an element of secondary structure in polypeptides where the polypeptide chain reverses its overall direction. A "turn" may, in a structurally more precise manner, be defined as a "structural motif where the Cα atoms of two residues separated by few (usually 1 to 5) peptide bonds are in close approach (<7 Å), while the corresponding residues do not form a regular secondary structure element such as an alpha helix or beta sheet". The turn according to the present invention may consist also of amino acids from the peptide moieties (specifically, of course, if no separate linker is located between the moieties). However, the turn according to the present invention may also be a loop (an "ω-loop being a catch-all term for a longer, extended or disordered loop without fixed internal hydrogen bonding; see also Toniolo et al., CRC Crit. Rev. Biochem. 9 (1980): 1-44).

According to the present invention the at least two beta-strands or at least two alpha-helices or the at least one beta-strand or the at least one alpha-helix are preferably separated by at least one turn resulting in peptides with alpha-helix and/or beta-strand moieties having the following general basic structures:
  a) beta-strand-(turn)-beta-strand
  b) alpha-helix-(turn)-alpha-helix
  c) beta-strand-(turn)-alpha-helix
  d) alpha-helix-(turn)-beta-strand According to the present invention the peptides disclosed herein may also comprise 3, 4 or even 5 beta-strands or alpha-helices as peptide moieties. In such a case the beta-strands or alpha-helices of the peptide can be grouped (e.g. two beta strands are located adjacent to each other) and preferably separated by one or more (e.g. 2, 3 or 4) turns or every single strand or helix is preferably separated by one or more turns. The isolated peptide of the present invention may therefore comprise also more than one stretches having the above general basic structure.

The peptides of the present invention have a net positive charge of +7 or more (for the purpose of a formal definition for the present invention, the net positive charge can be regarded as being defined at pH 7.4 in PBS buffer (phosphate buffered saline: 20 mM NaPi, 130 mM NaCl, pH 7.4)). This means that the peptides of the present invention may have preferably a net positive charge of +8, +9, +10, +11, +12, +13, +14, +15 or even of +20. A net positive charge of at least +7 of the peptides of the present invention results in a better adsorption to the target membrane (negatively charged) and better stabilization of the secondary structure by hydrogen bridge bonds. Calculation of net charges of a peptide is performed by adding the positive charges in a polypeptide (and, if present, subtracting the negative net charges). For example, a peptide with three lysine and four arginine residues has a net positive charge of +7 at a pH below 10.5 (pK lysine~10.5; arginine would even be positively charged at pH 12.5!). Amidating the C-terminal carboxylate group of a peptide adds one additional positive charge (see e.g. Yang et al., J. Pep. Sci. 10 (2004), 37-46). Another possibility to arrive at the net charge Z of a peptide at a certain pH can be estimated by calculation $$Z = \sum_i N_i \frac{10^{pKa_i}}{10^{pH} + 10^{pKa_i}} - \sum_j N_j \frac{10^{pH}}{10^{pH} + 10^{pKa_j}}$$

where $N_i$ are the number, and $pKa_i$ the pKa values, of the N-terminus and the side chains of Arginine, Lysine, and Histidine. The j-index pertain to the C-terminus and the Aspartic Acid, Glutamic Acid, Cysteine, Tyrosine amino acids.

The present peptides are preferably designed as "membrane active peptides", i.e. peptides that have—due to their physicochemical properties—an affinity to membranes. Common properties of membrane active peptides are disclosed e.g. in Last et al., Protein Science 22 (2013), 870-882 or Wang et al. J. Biol. Chem. 114 (2010), 13726-13735). Membrane active peptides are able to perturb the structural barrier function of cell membranes, which may eventually lead to cell lysis and cell death; these peptides share two common features: amphipathicity and a net positive charge (see Rekdal at al., Journal of Biological Chemistry 287 (2012), 233-244). They share common features as cationic residues being reported to be important for the initial electrostatic interaction and hydrophobic residues being important for membrane disruption (see Lohner et al., Combinatorial Chemistry & High Throughput Screening, 2005, 8, 241-256). Presence of membrane active properties can be determined by a variety of methods. Preferred methods for verifying membrane active property according to the present invention are permeability studies (dye release) using liposomes composed of phosphatidylserine, naturally exposed by cancer cells (Riedl et al., BBA 1808 (2011) 2638-2645) and thus relevant for cancer cells, as well as membrane permeabilization of tumor cells (propidium iodide (PI)-uptake). A membrane active peptide, especially a cancer membrane active peptide of the present invention should therefore preferably exhibit at least a membrane permeabilizing activity (ANTS/DPX-release) on PS-liposomes of more than 20% at a peptide concentration of 8 μM (test according to Zweytick et al., J. Biol. Chem. 286 (2011), 21266-21276). The PI-uptake of $10^5$ tumor cells should preferably be at least 20% after 8 hours of peptide incubation at a concentration of 20 μM of the membrane active peptide (test according to Schroder-Borm et al., J. FEBS Lett. 2005 Nov. 7; 579(27):6128-34).

Alpha helix (α-helix) is a common motif in the secondary structure of proteins, polypeptides and peptides. Alpha helices have a right-handed coiled or spiral conformation, in which every backbone N—H group donates a hydrogen bond to the backbone C=O group of the amino acid four residues earlier. The beta sheet (β-sheet) is the second form of regular secondary structure in proteins, polypeptides and peptides. Beta-sheets consist of beta strands connected laterally by at least two or three backbone hydrogen bonds, forming a generally twisted, pleated sheet. A turn is a structural motif where the Cα atoms of two residues separated by one or more peptide bonds are in close approach (approx. <7 Å), while the corresponding residues do not form a regular secondary structure element such as an alpha-helix or beta-sheet (Chou P Y et al., Annual Review of Biochemistry 47 (1978): 251-276). The secondary structure of putative membrane active isolated peptides can accurately be predicted by the online program PEP-FOLD: E.g. http://bioserv.rpbs.univ-paris-diderot.fr/PEP-FOLD/ (see Maupetit et al., Nucleic Acids Res. 37 (2009), W498-W503 and/or Thévenet et al., Nucleic Acid Res. 40 (2012), W288-W293).

The person skilled in the art is able to identify peptides exhibiting the properties as described herein using known methods. The secondary structure can be identified as described above. The net charge can be calculated by summing up the positive and negative charges of the amino acid residues present in a peptide.

One skilled in the art can easily synthesize the peptides of the present invention. Standard procedures for preparing synthetic peptides are well known in the art. Peptides of the present invention can be synthesized by commonly used methods as t-BOC or FMOC protection, preferably FMOC protection, of alpha-amino groups. Both methods involve stepwise syntheses whereby a single amino acid is added at each step starting from the carboxyl-terminus of the peptide (See, Coligan et al., Current Protocols in Immunology, Wiley Interscience, 2002, Unit 9). Peptides of the invention can also be synthesized by the solid phase peptide synthesis methods well known in the art. (Merrifield, J. Am. Chem. Soc., 85:2149, 1963), and Stewart and Young, Solid Phase Peptides Synthesis, (1969). Peptides can be synthesized using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about 0.25 to 1 hour at 0° C. After evaporation of the reagents, the peptides are extracted from the polymer with 1% acetic acid solution which is then lyophilized to yield the crude material. This can typically be purified by such techniques as gel filtration on Sephadex G-15 using 5% acetic acid as a solvent, by high pressure liquid chromatography, and the like. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and assessed by the solid phase Edman degradation (see e.g Protein Purification, M. P. Deutscher, ed. Methods in Enzymology, Vol 182, Academic Press, 1990). Automated synthesis using FMOC solid phase synthetic methods can be achieved using an automated peptide synthesizer (Model 432A, Applied Biosystems, Inc.).

The peptides/polypeptides of the present invention can also be synthesized using a fusion protein microbial method in which an anionic carrier peptide is fused to a cationic peptide. A method for such microbial production of cationic peptides having anti-microbial activity is provided in U.S. Pat. No. 5,593,866.

The peptides of the present invention thus produced can be purified by isolation/purification methods for proteins generally known in the field of protein chemistry. More particularly, there can be mentioned, for example, extraction, recrystallization, salting out with ammonium sulfate, sodium sulfate, etc., centrifugation, dialysis, ultrafiltration, adsorption chromatography, ion exchange chromatography, hydrophobic chromatography, normal phase chromatography, reversed-phase chromatography, gel filtration method, gel permeation chromatography, affinity chromatography, electrophoresis, countercurrent distribution, etc. and combinations of these. Most effective is a method by reversed-phase high performance liquid chromatography.

The peptides of the present invention may form a salt by addition of an acid. Examples of the acid include inorganic acids (such as trifluoroacetic acid, hydrochloric acid, hydrobromic acid, phosphoric acid, nitric acid, and sulfuric acid) or organic carboxylic acids (such as acetic acid, propionic acid, maleic acid, succinic acid, malic acid, citric acid, tartaric acid, and salicylic acid), acidic sugars such as glucuronic acid, galacturonic acid, gluconic acid, ascorbic acid, etc., acidic polysaccharides such as hyaluronic acid, chondroitin sulfates, alginic acid, or organic sulfonic acids (such as methanesulfonic acid, and p-toluenesulfonic acid), and the like. Of these salts, preferred is a pharmaceutically acceptable salt.

The peptides of the present invention may form a salt with a basic substance. Examples of the salt include, for example, pharmaceutically acceptable salts selected from salts with inorganic bases such as alkali metal salts (sodium salt, lithium salt, potassium salt etc.), alkaline earth metal salts, ammonium salts, and the like or salts with organic bases, such as diethanolamine salts, cyclohexylamine salts and the like.

The term "amino acid" and "amino acid residue" as used herein means L-amino acids. However, also D-amino acids may be employed in the manufacturing of the peptides according to the present invention.

The peptide of the present invention preferably exhibits amphipathic properties. This means that the peptide of the present invention may comprise hydrophobic and hydrophilic regions. Methods to determine amphipathic properties are well known in the art.

According to the present invention the isolated peptide comprises at least one peptide moiety having amino acid sequence $(X_1)_M$-$X_2$-$(X_3)_P$-$X_4$-$(X_5)_Q$-$X_6$-$(X_7)_S$ (SEQ ID No. 203) or the reverse sequence thereof, wherein $X_1$ is a hydrophobic amino acid, preferably selected from the group consisting of phenylalanine (Phe), alanine (Ala), leucine (Leu) and valine (Val), $X_2$ is a hydrophobic amino acid, preferably tryptophan (Trp), $X_3$ is selected from the group consisting of alanine (Ala), arginine (Arg), glutamine (Gln), asparagine (Asn), proline (Pro), isoleucine (Ile), leucine (Leu) and valine (Val), $X_4$ is selected from the group consisting of isoleucine (Ile), phenylalanine (Phe), tryptophan (Trp) and tyrosine (Tyr), $X_5$ is selected from the group consisting of arginine (Arg), lysine (Lys), tyrosine (Tyr) and phenylalanine (Phe), $X_6$ is a hydrophobic amino acid, preferably selected from the group consisting of isoleucine (Ile), tryptophan (Trp), valine (Val) and leucine (Leu), and $X_7$ is selected from the group consisting of arginine (Arg), lysine (Lys), isoleucine (Ile) and serine (Ser), and wherein M is 1 or 2,
Q is 1 or 2,
P is 2 or 3, and
S is 1, 2, 3 or 4 under the proviso that if $(X_5)_Q$ is Arg-Arg S is 1.

As used herein the term "reverse sequence" of an amino acid sequence means that a specific sequence is reversed. For instance, the reverse sequence of the amino acid sequence ABCDEFG is GFEDCBA.

The at least one peptide moiety has preferably an amino acid sequence selected from the group consisting of FWQRIRKVR (SEQ ID No. 1), FWQRRIRKVRR (SEQ ID No. 2), FWQRKIRKVRK (SEQ ID No. 3), FWQRNIRIRR (SEQ ID No. 4), FWQRNIRKVR (SEQ ID No. 5), FWQRNIRVR (SEQ ID No. 6), FWQRNIRKVRR (SEQ ID No. 7), FWQRNIRKVKK (SEQ ID No. 8), FWQRNIRKVRRR (SEQ ID No. 9), FWQRNIRKVKKK (SEQ ID No. 10), FWQRNIRKVRRRR (SEQ ID No. 11), FWQRNIRKVRRRI (SEQ ID No. 12), FWQRNIRKVKKKK (SEQ ID No. 13), FWQRNIRKVKKKI (SEQ ID No. 14), FWQRNIRKIR (SEQ ID No. 15), FWQRNIRKLR (SEQ ID No. 16), FWQRNIRKWR (SEQ ID No. 17), FWQRNWRKVR (SEQ ID No. 18), FWQRNFRKVR (SEQ ID No. 19), FWQRNYRKVR (SEQ ID No. 20), FWQRNIRKVS (SEQ ID No. 21), FWQRRIRIRR (SEQ ID No. 22), FWQRPIRKVR (SEQ ID No. 23), FWQRRIRKWR (SEQ ID No. 24), FWPRNIRKVR (SEQ ID No. 26), FWARNIRKVR (SEQ ID No. 27), FWIRNIRKVR (SEQ ID No. 28), FWLRNIRKVR (SEQ ID No. 29), FWVRNIRKVR (SEQ ID No. 30), FWQRNIFKVR (SEQ ID No. 31), FWQRNIYKVR (SEQ ID No. 32), FAWQRNIRKVR (SEQ ID No. 33), FLWQRNIRKVR (SEQ ID No. 35) and FVWQRNIRKVR (SEQ ID No. 36) or the reverse sequence thereof.

According to another preferred embodiment of the present invention the isolated peptide comprises at least one peptide moiety having amino acid sequence $(X_{1'})_{M'}$-$X_{2'}$-$(X_{3'})_{P'}$-$(X_{4'})_{Q'}$-$(X_{5'})_{T'}$-$(X_{6'})_{R'}$-$(X_{7'})_{S'}$ (SEQ ID No. 204) or the reverse sequence thereof, wherein $X_{1'}$ is a hydrophobic amino acid, preferably selected from the group consisting of phenylalanine (Phe) and isoleucine (Ile), $X_{2'}$ is a hydrophobic amino acid, preferably tryptophan (Trp), $X_{3'}$ is selected from the group consisting of glycine (Gly), asparagine (Asn), isoleucine (Ile) and phenylalanin (Phe), $X_{4'}$ is isoleucine (Ile) or tryptophan (Trp), $X_{5'}$ is arginine (Arg) or lysine (Lys), $X_{6'}$ is a hydrophobic amino acid, preferably selected from the group consisting of isoleucine (Ile), tryptophan (Trp) and valine (Val) and $X_{7'}$ is arginine (Arg), and wherein M' is 1 or 2,
T' is 1 or 2,
R' is 0 or 1,
P' is 1, 2 or 3,
Q' is 1, and
S' is 0, 1 or 2.

The at least one peptide moiety in the peptide of the present invention may have an amino acid sequence selected from the group consisting of FWRIRKWR (SEQ ID No. 37), FWRIRKVR (SEQ ID No. 38), FWRWRR (SEQ ID No. 39), FWRRWRR (SEQ ID No. 40), FWRRWIRR (SEQ ID No. 41), FWRGWRIRR (SEQ ID No. 42), FWRRFWRR (SEQ ID No. 43), FWRWRWR (SEQ ID No. 44), FWRIWRWR (SEQ ID No. 45), FWRIWRIWR (SEQ ID No. 46), FWRNIRKWR (SEQ ID No. 47) and FWRRRIRIRR (SEQ ID No. 48) or the reverse sequence thereof.

According to a further preferred embodiment of the present invention the isolated peptide comprises at least one peptide moiety having amino acid sequence $(X_{1''})_{M''}$-$X_{2''}$-$(X_{3''})_{P''}$-$(X_{4''})_{Q''}$-$(X_{5''})_{R''}$-$(X_{6''})_{S''}$ (SEQ ID No. 205) or the reverse sequence thereof, wherein $X_{1''}$ is a hydrophobic amino acid, preferably selected from the group consisting of proline (Pro) and phenylalanine (Phe), $X_{2''}$ is a hydrophobic amino acid, preferably tryptophan (Trp), $X_{3''}$ is selected from the group consisting of alanine (Ala), arginine (Arg), glutamine (Gln), lysine (Lys), tryptophan (Trp) and isoleucine (Ile), $X_{4''}$ is selected from the group consisting of arginine (Arg) and aspartate (Asp), X₅‴ is a hydrophobic amino acid, preferably selected from the group consisting of isoleucine (Ile), tryptophan (Trp), phenylalanine (Phe), valine (Val) and leucine (Leu), and X₆‴ is selected from the group consisting of arginine (Arg), lysine (Lys), isoleucine (Ile), serine (Ser) and aspartate (Asp), and wherein M″ is 0, 1, 2 or 3,
Q″ is 0, 1, 2 or 3,
R″ is 1 or 2,
P″ is 1, 2 or 3, and
S″ is 1, 2 or 3.

The at least one peptide moiety has preferably an amino acid sequence selected from the group consisting of PFWRWRIWR (SEQ ID No. 50), PFWRIRIRR (SEQ ID No. 51), PFWRQRIRR (SEQ ID No. 52), PFWRARIRR (SEQ ID No. 53), PFWRKRIRR (SEQ ID No. 54), PFWRKRLRR (SEQ ID No. 55), PFWRKRWRR (SEQ ID No. 56), PFWRRRIRR (SEQ ID No. 57), PFWRRRWRR (SEQ ID No. 58), PFWRIRIRRD (SEQ ID No. 59), PFFWRIRIRR (SEQ ID No. 60), PWRIRIRR (SEQ ID No. 61), PFWRRQIRR (SEQ ID No. 81), PFWRKKLKR (SEQ ID No. 82), PWRRIRR (SEQ ID No. 83), PWRRKIRR (SEQ ID No. 84) and PFWRRIRIRR (SEQ ID No. 85) or the reverse sequence thereof.

According to a preferred embodiment of the present invention the isolated peptide comprises at least one peptide moiety having amino acid sequence (X₁‴)_{M‴}-(X₂‴)_{O‴}-X₃‴-(X₄‴)_{P‴}—(X₅‴)_{Q‴}-(X₆‴)_{T‴}-(X₇‴)_{R‴}-(X₈‴)_{S‴} (SEQ ID No. 206) or the reverse sequence thereof, wherein X₁‴ is a hydrophobic amino acid, preferably selected from the group consisting of proline (Pro) and phenylalanine (Phe), X₂‴ is a basic amino acid, preferably arginine (Arg), X₃‴ is a hydrophobic amino acid, preferably tryptophan (Trp), X₄‴ is selected from the group consisting of alanine (Ala), arginine (Arg), glutamine (Gln), asparagine (Asn) and lysine (Lys), X₅‴ is selected from the group consisting of isoleucine (Ile), phenylalanine (Phe) and tryptophan (Trp), X₆‴ is selected from the group consisting of glutamine (Gln), arginine (Arg) and asparagine (Asn), X₇‴ is a hydrophobic amino acid, preferably selected from the group consisting of isoleucine (Ile), tryptophan (Trp) and phenylalanine (Phe), and X₈‴ is arginine (Arg), and wherein M‴ is 0, 1, 2 or 3,
T‴ is 0, 1, 2 or 3,
O‴ is 0 or 1,
P‴ is 1, 2 or 3,
Q‴ is 1 or 2, and
R‴ and S‴ are 0, 1 or 2.

The at least one peptide may have an amino acid sequence selected from the group consisting of FWRNIRIRR (SEQ ID No. 72), FWQRIRIRR (SEQ ID No. 73), FWRWRIWR (SEQ ID No. 74), FWRIRIRR (SEQ ID No. 75), FWRNIRIWRR (SEQ ID No. 76) and FWRNIRIRR (SEQ ID No. 77) or the reverse sequence thereof.

The isolated peptide comprises preferably at least one peptide moiety having an amino acid sequence selected from the group consisting of RFWQRNIRKVRR (SEQ ID No. 62), RFWQRNIRKYR (SEQ ID No. 63), PFWQRNIRKWR (SEQ ID No. 64), RFRWQRNIRKYRR (SEQ ID No. 65), RWKRINRQWF (SEQ ID No. 66), KRFCFKK (SEQ ID No. 67), KRFSFKKC (SEQ ID No. 68), KRWSWKK (SEQ ID No. 69), FRFSFKK (SEQ ID No. 70), RRFWFRR (SEQ ID No. 71), RFWQRNIRIRR (SEQ ID No. 78), RWQRNIRIRR (SEQ ID No. 79) and RRWFWRR (SEQ ID No. 86) or the reverse sequence thereof.

According to a further embodiment of the present invention the isolated peptide comprises at least one peptide moiety having an amino acid sequence selected from the group consisting of FIWQRNIRKVR (SEQ ID No. 34), FIWRWRWR (SEQ ID No. 49) and RRIRINRQWF (SEQ ID No. 80) or the reverse sequence thereof.

The isolated peptide of the present invention may comprise a single peptide moiety or the reverse sequence thereof as defined above. However, the isolated peptide may also comprise a multiplicity (at least two, at least three, at least four etc.) of said single peptide moieties or peptide moieties having the reversed sequence thereof. According to a very particular preferred embodiment of the present invention the isolated peptide comprises at least two, most preferably two, of the aforementioned peptide moieties with the sequence (X₁)_M-X₂-(X₃)_P-X₄-(X₅)_Q-X₆-(X₇)_S or the reverse sequence thereof.

According to a particularly preferred embodiment of the present invention the peptide of the present invention is selected from the peptides as shown in Table 1 having at least two beta-strands, or at least two alpha-helices or at least one beta-strand and at least one alpha-helix, said beta-strands and/or alpha-helices optionally being separated from each other by at least one turn. Preferred are those peptides having an amino acid sequence selected from the group consisting of SEQ ID. No. 89, SEQ ID. No. 91, SEQ ID. No. 93, SEQ ID. No. 95, SEQ ID. No. 97, SEQ ID. No. 98, SEQ ID. No. 99, SEQ ID. No. 101, SEQ ID. No. 103, SEQ ID. No. 105, SEQ ID. No. 106, SEQ ID. No. 107, SEQ ID. No. 109, SEQ ID. No. 111, SEQ ID. No. 114, SEQ ID. No. 116, SEQ ID. No. 117, SEQ ID. No. 118, SEQ ID. No. 120, SEQ ID. No. 122, SEQ ID. No. 123, SEQ ID. No. 124, SEQ ID. No. 125, SEQ ID. No. 126, SEQ ID. No. 127, SEQ ID. No. 128, SEQ ID. No. 129, SEQ ID. No. 130, SEQ ID. No. 131, SEQ ID. No. 132, SEQ ID. No. 134, SEQ ID. No. 136, SEQ ID. No. 137, SEQ ID. No. 138, SEQ ID. No. 139, SEQ ID. No. 140, SEQ ID. No. 141, SEQ ID. No. 142, SEQ ID. No. 143, SEQ ID. No. 144, SEQ ID. No. 145, SEQ ID. No. 146, SEQ ID. No. 148, SEQ ID. No. 149, SEQ ID. No. 150, SEQ ID. No. 156, SEQ ID. No. 153, SEQ ID. No. 154, SEQ ID. No. 156, SEQ ID. No. 158, SEQ ID. No. 160, SEQ ID. No. 162, SEQ ID. No. 164, SEQ ID. No. 166, SEQ ID. No. 168, SEQ ID. No. 170, SEQ ID. No. 172, SEQ ID. No. 174, SEQ ID. No. 176, SEQ ID. No. 178, SEQ ID. No. 180, SEQ ID. No. 181, SEQ ID. No. 182, SEQ ID. No. 183, SEQ ID. No. 184, SEQ ID. No. 186, SEQ ID. No. 188, SEQ ID. No. 190, SEQ ID. No. 192, SEQ ID. No. 194, SEQ ID. No. 195, SEQ ID. No. 197, SEQ ID. No. 199, SEQ ID. No. 200, SEQ ID. No. 201 and SEQ ID. No. 202. The variable "X" within these sequences can be 1 to 3 (i.e. 1, 2 or 3) glycine or proline residues, preferably 1 proline residue. Particularly preferred peptides are those having a sequence selected from the group consisting of SEQ ID. No. 125, SEQ ID. No. 126, SEQ ID. No. 127, SEQ ID. No. 128, SEQ ID. No. 105, SEQ ID. No. 106, SEQ ID. No. 107, SEQ ID. No. 174, SEQ ID. No. 176, SEQ ID. No. 141, SEQ ID. No. 142, SEQ ID. No. 143, SEQ ID. No. 144, SEQ ID. No. 181, SEQ ID. No. 182, SEQ ID. No. 183 and SEQ ID. No. 184.

According to a preferred embodiment of the present invention the peptide of the present invention has/comprises/consists of a sequence selected from the group consisting of SEQ ID. No. 125, SEQ ID. No. 127, SEQ ID. No. 128, SEQ ID. No. 106 and SEQ ID. No. 141 and No. 184. For example, SEQ ID. Nos. 128, 184 and 106, especially Nos. 128 and 184, are specifically suitable for cancer treatment, especially for the treatment of glioblastoma and malignant melanoma.

Of course the isolated peptide of the present invention may also comprise a combination of at least two of the aforementioned peptides.

According to a preferred embodiment of the present invention at least two peptides having an amino acid sequence as defined herein or the reverse sequence thereof are fused directly or via a linker, wherein said linker is preferably part of the turn, to each other.

According to a further preferred embodiment of the present invention said isolated peptide comprises at least two, preferably two, peptide moieties with the sequence $(X_1)_M$-$X_2$-$(X_3)_P$-$X_4$-$(X_5)_Q$-$X_6$-$(X_7)_S$ or the reverse sequence thereof ("retro" sequence) having the same amino acid sequence and being selected from the peptide moieties having an amino acid sequence as defined above or the reverse sequence thereof, wherein the at least two peptide moieties are fused directly or via a linker to each other (e.g. the "reverse" or "retro" sequence of $X_1X_2X_3X_4$ is $X_4X_3X_2X_1$; e.g. "retro" sequence of PWRIRIRR is RRIRIRWP).

Said isolated peptide may comprise at least two, preferably two, peptide moieties, wherein an at least one first peptide moiety has an amino acid sequence as defined above and the at least one second peptide moiety is the reverse sequence thereof, wherein the at least two peptide moieties are fused directly or via a linker to each other.

The linker comprises preferably 1 to 10, preferably 1 to 8, more preferably 1 to 5, even more preferably 1 to 3, amino acid residues.

According to a particularly preferred embodiment of the present invention the linker, being preferably part of the turn, comprises or consists of proline and/or glycine, preferably proline.

The isolated peptide of the present invention or a pharmaceutical preparation comprising at least one of said isolated peptides can be used to treat cancer of solid and non-solid tumors, including metastases, whereby the cancer is preferably selected from the group consisting of melanoma, rhabdomyosarcoma, glioblastoma, colorectal cancer, breast cancer, lymphoma, prostate cancer, pancreatic cancer, renal cancer, ovarian cancer and lung cancer. Particularly preferred cancers to be treated with the peptides of the present invention are glioblastoma and melanoma, preferably malignant melanoma. The peptides of the present invention are preferably administered to a patient in need thereof in an amount of 100 µg/kg body weight to 100 mg/kg body weight, preferably 1 mg/kg body weight to 50 mg/kg body weight, more preferably 5 mg/kg body weight to 15 mg/kg body weight, in particular 10 mg/kg body weight. Furthermore the peptides of the present invention are preferably administered daily (e.g. three times a day, twice a day or once a day), every $2^{rd}$, every $3^{rd}$, every $4^{th}$ or every $5^{th}$ day.

In order to obtain a pharmaceutical composition with even better anti-cancer or anti-tumor activity additional agents exhibiting similar properties as the peptides according to the present invention are added. Of course it is also possible to add agents with activities other than the peptides according to the present invention. These substances may be helpful in increasing the bioavailability such as for example increasing the stability of the peptides or their delivery.

Such compositions according to the present invention may preferably further comprise a pharmaceutically acceptable excipient.

The pharmaceutical composition of the present invention may consist of the peptide of the present invention alone or may be in the form of a composition comprising the peptide of the present invention and a pharmaceutically acceptable carrier. The pharmaceutically acceptable carrier which can be used is not limited particularly and includes an excipient, a binder, a lubricant, a colorant, a disintegrant, a buffer, an isotonic agent, a preservative, an anesthetic, and the like which can be used in a medical field.

The composition of the present invention can be administered, depending on the cancer to be treated locally or systemically by injection (subcutaneous, intracutaneous, intravenous, intraperitoneal, etc.), eye dropping, instillation, percutaneous administration, oral administration, inhalation, etc. The peptides of the present invention can also be directly injected into the tumor/cancer to be treated.

Also, the dosage form such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointment, suppositories, pessaries, and the like can be appropriately selected depending on the administration method, and the composition of the present invention can be accordingly formulated.

Another aspect of the present invention relates to the use of a peptide as defined above for the manufacturing of a medicament for treating cancer in a mammal, in particular in a human patient.

A further aspect of the present invention relates to a method for treating a mammal, in particular a human patient, suffering from cancer by administering to said mammal an effective amount of a peptide as defined above.

As used herein, the term "therapeutically effective amount" or "effective amount" means that to a mammal an amount of the peptide of the present invention is administered which allows the reduction of the tumor cells within the body of at least 10%, preferably at least 20%, more preferably at least 50%, and more preferably sufficient to reduce by 90%. Generally, the dosage will vary with age, condition and sex, and can be determined by one skilled in the art. The dosage can be adjusted by the individual physician in the event of any contraindications. In any event, the effectiveness of treatment can be determined by monitoring the presence of the cancer cells within the body.

According to a particularly preferred embodiment of the present invention the peptide of the present invention has/comprises/consists of a sequence selected from the group consisting of SEQ ID. No. 125, SEQ ID. No. 127, SEQ ID. No. 128, SEQ ID. No. 106 and SEQ ID. No. 141 and is used in the treatment of glioblastoma and melanoma, preferably malignant melanoma. The peptide of the present invention can be administered by directly injecting the peptide into the tumor/cancer.

Preferably the present invention is defined as in the following embodiments:

1. An isolated peptide to be used in the treatment of cancer consisting of 12 to 50 amino acid residues comprising
   at least two beta-strands, or
   at least two alpha-helices or
   at least one beta-strand and at least one alpha-helix,
wherein said beta-strands and/or alpha-helices are preferably separated from each other by at least one turn, wherein the peptide has a net positive charge of +7 or more.

2. Peptide for use according to embodiment 1, wherein the peptide comprises at least 5 hydrophobic amino acid residues.

3. Peptide for use according to embodiment 1 or 2, wherein the isolated peptide comprises at least one peptide moiety having amino acid sequence $(X_1)_M$-$X_2$-$(X_3)_P$-$X_4$-$(X_5)_Q$-$X_6$-$(X_7)_S$ or the reverse sequence thereof, wherein $X_1$ is a hydrophobic amino acid, preferably selected from the group consisting of phenylalanine (Phe), alanine (Ala), leucine (Leu) and valine (Val), $X_2$ is a hydrophobic amino acid, preferably tryptophan (Trp), $X_3$ is selected from the group consisting of alanine (Ala), arginine (Arg), glutamine (Gln), asparagine (Asn), proline (Pro), isoleucine (Ile), leucine (Leu) and valine (Val), $X_4$ is selected from the group consisting of isoleucine (Ile), phenylalanine (Phe), tryptophan (Trp) and tyrosine (Tyr), $X_5$ is selected from the group consisting of arginine (Arg), lysine (Lys), tyrosine (Tyr) and phenylalanine (Phe), $X_6$ is a hydrophobic amino acid, preferably selected from the group consisting of isoleucine (Ile), tryptophan (Trp), valine (Val) and leucine (Leu), and $X_7$ is selected from the group consisting of arginine (Arg), lysine (Lys), isoleucine (Ile) and serine (Ser), and wherein M is 1 or 2,
Q is 1 or 2,
P is 2 or 3, and
S is 1, 2, 3 or 4 under the proviso that if $(X_5)_Q$ is Arg-Arg S is 1.

4. Peptide for use according to embodiment 3, wherein the at least one peptide moiety has an amino acid sequence selected from the group consisting of FWQRIRKVR (SEQ ID No. 1), FWQRRIRKVRR (SEQ ID No. 2), FWQRKIRKVRK (SEQ ID No. 3), FWQRNIRIRR (SEQ ID No. 4), FWQRNIRKVR (SEQ ID No. 5), FWQRNIRVR (SEQ ID No. 6), FWQRNIRKVRR (SEQ ID No. 7), FWQRNIRKVKK (SEQ ID No. 8), FWQRNIRKVRRR (SEQ ID No. 9), FWQRNIRKVKKK (SEQ ID No. 10), FWQRNIRKVRRRR (SEQ ID No. 11), FWQRNIRKVR-RRI (SEQ ID No. 12), FWQRNIRKVKKKK (SEQ ID No. 13), FWQRNIRKVKKKI (SEQ ID No. 14), FWQRNIRKIR (SEQ ID No. 15), FWQRNIRKLR (SEQ ID No. 16), FWQRNIRKWR (SEQ ID No. 17), FWQRNWRKVR (SEQ ID No. 18), FWQRNFRKVR (SEQ ID No. 19), FWQRNYRKVR (SEQ ID No. 20), FWQRNIRKVS (SEQ ID No. 21), FWQRRIRIRR (SEQ ID No. 22), FWQRPIRKVR (SEQ ID No. 23), FWQRRIRKWR (SEQ ID No. 24), FWPRNIRKVR (SEQ ID No. 26), FWARNIRKVR (SEQ ID No. 27), FWIRNIRKVR (SEQ ID No. 28), FWLRNIRKVR (SEQ ID No. 29), FWVRNIRKVR (SEQ ID No. 30), FWQRNIFKVR (SEQ ID No. 31), FWQRNIYKVR (SEQ ID No. 32), FAWQRNIRKVR (SEQ ID No. 33), FLWQRNIRKVR (SEQ ID No. 35) and FVWQRNIRKVR (SEQ ID No. 36) or the reverse sequence thereof.

5. Peptide for use according to any one of embodiments 1 to 4, wherein the isolated peptide comprises at least one peptide moiety having amino acid sequence $(X_{1'})_{M'}$-$X_{2'}$-$(X_{3'})$-$(X_{4'})_{Q'}$-$(X_{5'})_{T'}$-$(X_{6'})_{R'}$-$(X_{7'})_{S'}$ or the reverse sequence thereof, wherein $X_{1'}$ is a hydrophobic amino acid, preferably selected from the group consisting of phenylalanine (Phe) and isoleucine (Ile), $X_{2'}$ is a hydrophobic amino acid, preferably tryptophan (Trp), $X_{3'}$ is selected from the group consisting of glycine (Gly), asparagine (Asn), isoleucine (Ile) and phenylalanin (Phe), $X_{4'}$ is isoleucine (Ile) or tryptophan (Trp), $X_{5'}$ is arginine (Arg) or lysine (Lys), $X_{6'}$ is a hydrophobic amino acid, preferably selected from the group consisting of isoleucine (Ile), tryptophan (Trp) and valine (Val) and $X_{7'}$ is arginine (Arg), and wherein M' is 1 or 2,
T' is 1 or 2,
R' is 0 or 1,
P' is 1, 2 or 3,
Q' is 1, and
S' is 0, 1 or 2.

6. Peptide for use according to embodiment 5, wherein the at least one peptide moiety has an amino acid sequence selected from the group consisting of FWRIRKWR (SEQ ID No. 37), FWRIRKVR (SEQ ID No. 38), FWRWRR (SEQ ID No. 39), FWRRWRR (SEQ ID No. 40), FWRRWIRR (SEQ ID No. 41), FWRGWRIRR (SEQ ID No. 42), FWR-RFWRR (SEQ ID No. 43), FWRWRWR (SEQ ID No. 44), FWRIWRWR (SEQ ID No. 45), FWRIWRIWR (SEQ ID No. 46), FWRNIRKWR (SEQ ID No. 47) and FWRR-RIRIRR (SEQ ID No. 48) or the reverse sequence thereof.

7. Peptide for use according to any one of embodiments 1 to 6, wherein the isolated peptide comprises at least one peptide moiety having amino acid sequence $(X_{1''})_{M''}$-$X_{2''}$-$(X_{3''})_{P''}$-$(X_{4''})_{Q''}$-$(X_{5''})_{R''}$-$(X_{6''})_{S''}$ or the reverse sequence thereof, wherein $X_{1''}$ is a hydrophobic amino acid, preferably selected from the group consisting of proline (Pro) and phenylalanine (Phe), $X_{2''}$ is a hydrophobic amino acid, preferably tryptophan (Trp), $X_{3''}$ is selected from the group consisting of alanine (Ala), arginine (Arg), glutamine (Gln), lysine (Lys), tryptophan (Trp) and isoleucine (Ile), $X_{4''}$ is selected from the group consisting of arginine (Arg) and aspartate (Asp), $X_{5''}$ is a hydrophobic amino acid, preferably selected from the group consisting of isoleucine (Ile), tryptophan (Trp), phenylalanine (Phe), valine (Val) and leucine (Leu), and $X_{6''}$ is selected from the group consisting of arginine (Arg), lysine (Lys), isoleucine (Ile), serine (Ser) and aspartate (Asp), and wherein M" is 0, 1, 2 or 3,
Q" is 0, 1, 2 or 3,
R" is 1 or 2,
P" is 1, 2 or 3, and
S" is 1, 2 or 3.

8. Peptide for use according to embodiment 7, wherein the at least one peptide moiety has an amino acid sequence selected from the group consisting of PFWRWRIWR (SEQ ID No. 50), PFWRIRIRR (SEQ ID No. 51), PFWRQRIRR (SEQ ID No. 52), PFWRARIRR (SEQ ID No. 53), PFWRKRIRR (SEQ ID No. 54), PFWRKRLRR (SEQ ID No. 55), PFWRKRWRR (SEQ ID No. 56), PFWRRRIRR (SEQ ID No. 57), PFWRRRWRR (SEQ ID No. 58), PFWRIRIRRD (SEQ ID No. 59), PFFWRIRIRR (SEQ ID No. 60), PWRIRIRR (SEQ ID No. 61), PFWRRQIRR (SEQ ID No. 81), PFWRKKLKR (SEQ ID No. 82), PWRRIRR (SEQ ID No. 83), PWRRKIRR (SEQ ID No. 84) and PFWRRIRIRR (SEQ ID No. 85) or the reverse sequence thereof.

9. Peptide for use according to any one of embodiments 1 to 8, wherein the isolated peptide comprises at least one peptide moiety having amino acid sequence $(X_{1'''})_{M'''}$-$(X_{2'''})_{O'''}$-$X_{3'''}$-$(X_{4'''})_{P'''}$-$(X_{5'''})_{Q'''}$-$(X_{6'''})_{T'''}$-$(X_{7'''})_{R'''}$-$(X_{8'''})_{S'''}$ or the reverse sequence thereof, wherein $X_{1'''}$ is a hydrophobic amino acid, preferably selected from the group consisting of proline (Pro) and phenylalanine (Phe), $X_{2'''}$ is a basic amino acid, preferably arginine (Arg), $X_{3'''}$ is a hydrophobic amino acid, preferably tryptophan (Trp), $X_{4'''}$ is selected from the group consisting of alanine (Ala), arginine (Arg), glutamine (Gln), asparagine (Asn) and lysine (Lys), $X_{5'''}$ is selected from the group consisting of isoleucine (Ile), phenylalanine (Phe) and tryptophan (Trp), $X_{6'''}$ is selected from the group consisting of glutamine (Gln), arginine (Arg) and asparagine (Asn), $X_{7'''}$ is a hydrophobic amino acid, preferably selected from the group consisting of isoleucine (Ile), tryptophan (Trp) and phenylalanine (Phe), and $X_{8'''}$ is arginine (Arg), and wherein M''' is 0, 1, 2 or 3, T''' is 0, 1, 2 or 3, O''' is 0 or 1, P''' is 1, 2 or 3, Q''' is 1 or 2, and R''' and S''' are 0, 1 or 2.

10. Peptide for use according to embodiment 9, wherein the at least one peptide moiety has an amino acid sequence selected from the group consisting of FWRNIRIRR (SEQ ID No. 72), FWQRIRIRR (SEQ ID No. 73), FWRWRIWR (SEQ ID No. 74), FWRIRIRR (SEQ ID No. 75), FWRNIRI-WRR (SEQ ID No. 76) and FWRNIRIRR (SEQ ID No. 77) or the reverse sequence thereof.

11. Peptide for use according to any one of embodiments 1 to 10, wherein the isolated peptide comprises at least one peptide moiety having an amino acid sequence selected from the group consisting of RFWQRNIRKVRR (SEQ ID No. 62), RFWQRNIRKYR (SEQ ID No. 63), PFWQRNIRKWR (SEQ ID No. 64), RFRWQRNIRKYRR (SEQ ID No. 65), RWKRINRQWF (SEQ ID No. 66), KRFCFKK (SEQ ID No. 67), KRFSFKKC (SEQ ID No. 68), KRWSWKK (SEQ ID No. 69), FRFSFKK (SEQ ID No. 70), RRFWFRR (SEQ ID No. 71), RFWQRNIRIRR (SEQ ID No. 78), RWQRNIRIRR (SEQ ID No. 79) and RRWFWRR (SEQ ID No. 86) or the reverse sequence thereof.

12. Peptide for use according to any one of embodiments 1 to 11, wherein the isolated peptide comprises at least one peptide moiety having an amino acid sequence selected from the group consisting of FIWQRNIRKVR (SEQ ID No. 34), FIWRWRWR (SEQ ID No. 49) and RRIRINRQWF (SEQ ID No. 80) or the reverse sequence thereof.

13. Peptide for use according to any one of embodiments 1 to 12, wherein at least two peptide moieties having an amino acid sequence as defined in any one of embodiments 4 to 13 or the reverse sequence thereof are fused directly or via a linker to each other.

14. Peptide for use according to any one of embodiments 1 to 12, wherein said isolated peptide comprises at least two, preferably two, peptide moieties having the same amino acid sequence and being selected from the peptide moieties having an amino acid sequence as defined in any one of embodiments 4 to 13 or the reverse sequence thereof, wherein the at least two peptide moieties are fused directly or via a linker to each other.

15. Peptide for use according to any one of embodiments 1 to 12, wherein said isolated peptide comprises at least two, preferably two, peptide moieties, wherein an at least one first peptide moiety has an amino acid sequence as defined in any one of embodiments 4 to 13 and the at least one second peptide moiety is the reverse sequence thereof, wherein the at least two peptide moieties are fused directly or via a linker to each other.

16. Peptide for use according to any one of embodiments 13 to 15, wherein the linker comprises 1 to 10, preferably 1 to 8, more preferably 1 to 5, even more preferably 1 to 3, amino acid residues.

17. Peptide for use according to any one of embodiments 13 to 16, wherein the linker comprises proline and/or glycine residues.

18. Peptide for use according to any one of embodiments 13 to 17, wherein the linker consists of one, two or three, preferably one, proline residue.

19. Peptide for use according to any one of embodiments 1 to 18, wherein the cancer is selected from solid and non-solid tumors, including metastases.

20. Peptide for use according to any one of embodiments 1 to 19, wherein the cancer is selected from the group consisting of melanoma, rhabdomyosarcoma, glioblastoma, colorectal cancer, breast cancer, lymphoma, prostate cancer, pancreatic cancer, renal cancer, ovarian cancer and lung cancer.

21. Use of a peptide as defined in any one of embodiments 1 to 18 for the manufacturing of a medicament for treating cancer in a mammal, in particular in a human patient.

22. Method for treating a mammal, in particular a human patient, suffering from cancer by administering to said mammal an effective amount of a peptide as defined in any one of embodiments 1 to 18.

The present invention is further illustrated by the following figures and examples, however, without being restricted thereto.

BRIEF DESCRIPTION OF THE DRAWINGS

FIG. 1 shows the secondary structures of PEP-322 (A) and R-DIM-P-PEP-322 (B) in Hepes buffer (first bar) or presence of SDS and DPC at peptide to surfactant ratios of 1:25 and 1:100, determined using CD spectroscopy. Bottom shows α-helical content in dark gray; second from bottom shows β-sheet in light grey; third from bottom shows turns in middle grey; random coil structures are shown in dark grey at the top.

FIG. 15 shows cytotoxicity of peptides R-DIM-P-PEP-316, DIM-PEP-317, DIM-PEP-318, DIM-PEP-322, R-DIM-PEP-322, R-DIM-P-PEP-322, R-DIM-PEP-323, DIM-PEP-324, R-DIM-PEP-324, R-DIM-P-PEP-330, R-DIM-P-PEP-332, R-DIM-P-PEP-334 and R-DIM-PEP-337 and human Lactoferricin (hLFcin)(37-61) after 1 h, 2 h, 4 h and h of incubation, respectively, against U87 mg glioblastoma cell line.

EXAMPLES

Experimental Procedures

Figure 2:
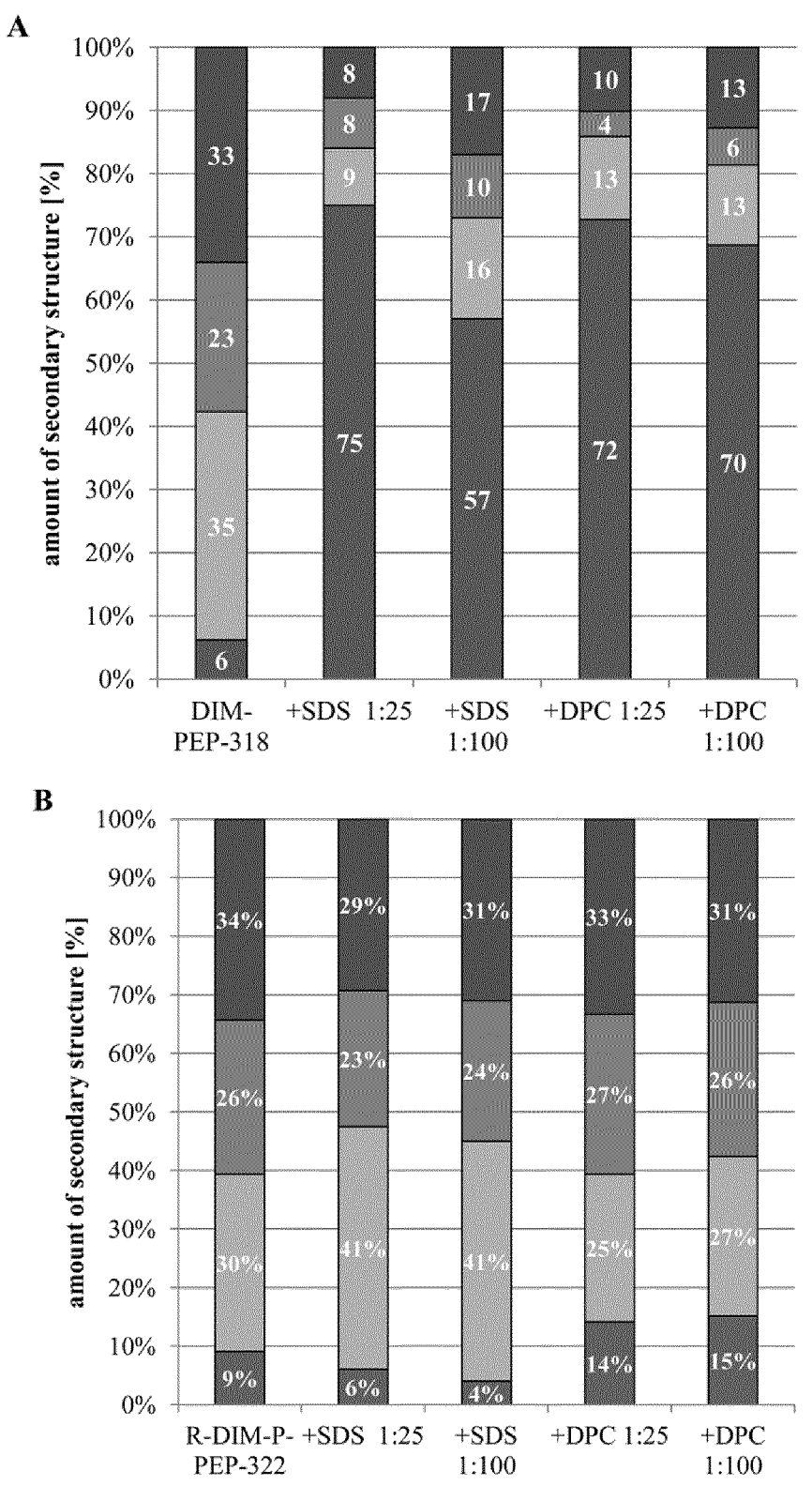
FIG. 2 shows the secondary structures of DIM-PEP-318 (A) and R-DIM-P-PEP-322 (B) in the absence and presence of SDS and DPC at peptide to surfactant ratios of 1:25 and 1:100, determined using CD spectroscopy. Bottom shows α-helical content in dark gray; second from bottom shows β-sheet in light grey; third from bottom shows turns in middle grey; random coil structures are shown in dark grey at the top.

Materials and Peptide Synthesis 1,2-Dihexadecanoyl-sn-glycero-3-phosphocholine (DPPC), 1-Hexadecanoyl-2-(9Z-octadecenoyl)-sn-glycero-3-phosphocholine (POPC), 1,2-Dihexadecanoyl-sn-glycero-3-phospho-L-serine (Na-salt) (DPPS) and 1-Hexadecanoyl-2-(9Z-octadecenoyl)-sn-glycero-3-phospho-L-serine (Na-salt) (POPS) were purchased from Avanti Polar Lipids, Inc. (USA), and used without further purification. Stock solutions of DPPC and POPC were prepared in $CHCl_3/CH_3OH$ (2:1, v/v), stock solutions of DPPS and POPS were prepared in $CHCl_3/CH_3OH$ (9:1, v/v) and stored at −18° C.

The amidated peptides PEP-322 (PFWRIRIRR-$NH_2$ (SEQ ID NO: 51), M=1298.6 g/mole, DIM-PEP-322 (2580.2), M=g/mole, R-DIM-PEP-322 (2580.2), M=g/mole, R-DIM-P-PEP-322 (PFWRIRIRRPRRIRIRWFP-$NH_2$ (SEQ ID NO: 128), M=2677.4 g/mole), PEP-318 (FWQR-RIRRWRR-$NH_2$ (SEQ ID NO: 112), M=1715.0 g/mol), DIM-PEP-318 (FWQRRIRRWRRFWQRRIRRWRR-$NH_2$ (SEQ ID NO: 113), M=3413.1 g/mol), PEP-324 (PFF-WRIRIRR-$NH_2$ (SEQ ID NO: 60), M=1445.8 g/mol), DIM-PEP-324 (PFFWRIRIRRPFFWRIRIRR-$NH_2$ (SEQ ID NO: 141), M=2874.6 g/mol), PEP-316 (RWKRINRQWF-$NH_2$ (SEQ ID NO: 66), M=1488.8 g/mol) and R-DIM-PEP-316 (RWKRINRQWFFWQRNIRKWR-$NH_2$ (SEQ ID NO: 106), M=2960.5 g/mol) were purchased from NeoMPS, Inc. (San Diego, Calif., USA). (Human lactoferricin (hLFcin) 37-61) (TKCFQWQRNMRKVRGPPVSCIKRDS (SEQ ID No. 207), M=3020.5 g/mol) was purchased from Anaspec, Inc (Fremont, Calif., USA). The purities were >95% as determined by RP-HPLC. Peptides were dissolved in acetic acid (0.1%, v/v) at a concentration of 3 mg/ml. Peptide solutions were stored at 4° C. and concentrations were determined photometrically at 280 nm.

ANTS (8-aminonaphthalene-1,3,6-trisulfonic acid, disodium salt) and DPX (p-xylene-bis-pyridinium bromide) used for permeability studies were purchased from Molecular Probes (Eugene, Oreg.).

The peptides of the present invention, which have been used in part in the present example are indicated in Table 1:
Table 1:
List of sequences of peptide moieties and isolated peptides (-retro); the present invention includes all sequences in isolated peptide (The term "DIM-" used hereinafter was used to assign a "di-moiety" peptide according to the present invention) (peptide moietysequence+peptide moietysequence) isolated peptide retro (R-DIM-) (peptide moiety sequence+peptide moiety retro sequence), isolated peptide with linker (DIM-X-) (peptide moiety sequence+X+peptide moiety sequence) isolated peptide retro with linker X (R-DIM-X-) (peptide moiety sequence+X+peptide moiety retro sequence) (X=(Pro and/or, preferably or, Gly)$_{1-3}$, whereby X is preferably a single proline residue); the present invention includes as well trimer and tetrameric derivatives termed as polymeric versions of the isolated peptide according to the present invention, although the more consequent wording would be "poly-moietic peptide" ("tri-moiety peptide", "tetra-moiety peptide", "penta-moiety peptide", etc.); —represents a peptide bond between the peptide moieties and between the peptides and the linker; "retro sequence" or "reverse sequence" refers to an amino acid sequence comprising a sequence which has a reverse order than the amino acid sequence from which it is derived from (e.g. the retro sequence of ABCDE is EDCBA).

| Designation | Sequence | SEQ ID No. |
|---|---|---|
| PEP (parent) | FQWQRNIRKVR | 87 |
| DIM-PEP | FQWQRNIRKVR - FQWQRNIRKVR | 88 |
| DIM-X-PEP | FQWQRNIRKVR X FQWQRNIRKVR | 89 |
| R-DIM-PEP | FQWQRNIRKVR    RVKRINRQWQF | 90 |
| R-DIM-X-PEP | FQWQRNIRKVR X RVKRINRQWQF | 91 |

-continued

| Designation | Sequence | SEQ ID No. |
|---|---|---|
| PEP-313 | FWQRNIRIRR | 4 |
| DIM-PEP-313 | FWQRNIRIRR   FWQRNIRIRR | 92 |
| DIM-X-PEP-313 | FWQRNIRIRR X FWQRNIRIRR | 93 |
| R-DIM-PEP-313 | FWQRNIRIRR   RRIRINRQWF | 94 |
| R-DIM-X-PEP-313 | FWQRNIRIRR X RRIRINRQWF | 95 |
| PEP-314 | RRIRINRQWF | 80 |
| DIM-PEP-314 | RRIRINRQWF   RRIRINRQWF | 96 |
| DIM-X-PEP-314 | RRIRINRQWF X RRIRINRQWF | 97 |
| R-DIM-PEP-314 | RRIRINRQWF   FWQRNIRIRR | 98 |
| R-DIM-X-PEP-314 | RRIRINRQWF X FWQRNIRIRR | 99 |
| PEP-315 | FWQRNIRKWR | 17 |
| DIM-PEP-315 | FWQRNIRKWR   FWQRNIRKWR | 100 |
| DIM-X-PEP-315 | FWQRNIRKWR X FWQRNIRKWR | 101 |
| R-DIM-PEP-315 | FWQRNIRKWR   RWKRINRQWF | 102 |
| R-DIM-X-PEP-315 | FWQRNIRKWR X RWKRINRQWF | 103 |
| PEP-316 | RWKRINRQWF | 66 |
| DIM-PEP-316 | RWKRINRQWF   RWKRINRQWF | 104 |
| DIM-X-PEP-316 | RWKRINRQWF X RWKRINRQWF | 105 |
| R-DIM-PEP-316 | RWKRINRQWF   FWQRNIRKWR | 106 |
| R-DIM-X-PEP-316 | RWKRINRQWF X FWQRNIRKWR | 107 |
| PEP-317 | FWQRRIRKWR | 24 |
| DIM-PEP-317 | FWQRRIRKWR   FWQRRIRKWR | 108 |
| DIM-X-PEP-317 | FWQRRIRKWR X FWQRRIRKWR | 109 |
| R-DIM-PEP-317 | FWQRRIRKWR   RWKRIRRQWF | 110 |
| R-DIM-X-PEP-317 | FWQRRIRKWR X RWKRIRRQWF | 111 |
| PEP-318 | FWQRRIRRWRR | 112 |
| DIM-PEP-318 | FWQRRIRRWRR   FWQRIRRWRR | 113 |
| DIM-X-PEP-318 | FWQRRIRRWRR X FWQRIRRWRR | 114 |
| R-DIM-PEP-318 | FWQRRIRRWRR   RRWRIRRQWF | 115 |
| R-DIM-X-PEP-318 | FWQRRIRRWRR X RRWRIRRQWF | 116 |
| PEP-319 | PFWQRNIRKWR | 64 |
| DIM-PEP-319 | PFWQRNIRKWR   PFWQRNIRKWR | 117 |
| DIM-X-PEP-319 | PFWQRNIRKWR X PFWQRNIRKWR | 118 |
| R-DIM-PEP-319 | PFWQRNIRKWR   RWKRINRQWFP | 119 |
| R-DIM-X-PEP-319 | PFWQRNIRKWR X RWKRINRQWFP | 120 |
| PEP-320 | FWRNIRKWR | 47 |
| DIM-PEP-320 | FWRNIRKWR   FWRNIRKWR | 121 |
| DIM-X-PEP-320 | FWRNIRKWR X FWRNIRKWR | 122 |
| R-DIM-PEP-320 | FWRNIRKWR   RWKRINRWF | 123 |
| R-DIM-X-PEP-320 | FWRNIRKWR X RWKRINRWF | 124 |
| PEP-322 | PFWRIRIRR | 51 |
| DIM-PEP-322 | PFWRIRIRR   PFWRIRIRR | 125 |
| DIM-X-PEP-322 | PFWRIRIRR X PFWRIRIRR | 126 |
| R-DIM-PEP-322 | PFWRIRIRR   RRIRIRWFP | 127 |
| R-DIM-X-PEP-322 | PFWRIRIRR X RRIRIRWFP | 128 |
| PEP-215 | FWRIRIRR | 75 |
| DIM-PEP-215 | FWRIRIRR   FWRIRIRR | 129 |
| DIM-X-PEP-215 | FWRIRIRR X FWRIRIRR | 130 |
| R-DIM-PEP-215 | FWRIRIRR   RRIRIRWF | 131 |
| R-DIM-X-PEP-215 | FWRIRIRR X RRIRIRWF | 132 |
| PEP-227 | FWRRFWRR | 43 |
| DIM-PEP-227 | FWRRFWRR   FWRRFWRR | 133 |
| DIM-X-PEP-227 | FWRRFWRR X FWRRFWRR | 134 |
| R-DIM-PEP-227 | FWRRFWRR   RRWFRRWF | 135 |
| R-DIM-X-PEP-227 | FWRRFWRR X RRWFRRWF | 136 |
| PEP-323 | PFWRIRIRRD | 59 |
| DIM-PEP-323 | PFWRIRIRRD   PFWRIRIRRD | 137 |
| DIM-X-PEP-323 | PFWRIRIRRD X PFWRIRIRRD | 138 |
| R-DIM-PEP-323 | PFWRIRIRRD   DRRIRIRWFP | 139 |
| R-DIM-X-PEP-323 | PFWRIRIRRD X DRRIRIRWFP | 140 |
| PEP-324 | PFFWRIRIRR | 60 |
| DIM-PEP-324 | PFFWRIRIRR   PFFWRIRIRR | 141 |
| DIM-X-PEP-324 | PFFWRIRIRR X PFFWRIRIRR | 142 |
| R-DIM-PEP-324 | PFFWRIRIRR   RRIRIRWFFP | 143 |
| R-DIM-X-PEP-324 | PFFWRIRIRR X RRIRIRWFFP | 144 |
| PEP-325 | PFWRQRIRR | 52 |
| DIM-PEP-325 | PFWRQRIRR   PFWRQRIRR | 145 |
| DIM-X-PEP-325 | PFWRQRIRR X PFWRQRIRR | 146 |
| R-DIM-PEP-325 | PFWRQRIRR   RRIRQRWFP | 147 |
| R-DIM-X-PEP-325 | PFWRQRIRR X RRIRQRWFP | 148 |
| PEP-326 | PFWRRQIRR | 81 |
| DIM-PEP-326 | PFWRRQIRR   PFWRRQIRR | 149 |
| DIM-X-PEP-326 | PFWRRQIRR X PFWRRQIRR | 150 |
| R-DIM-PEP-326 | PFWRRQIRR   RRIQRRWFP | 151 |
| R-DIM-X-PEP-326 | PFWRRQIRR X RRIQRRWFP | 152 |
| PEP-327 | PFWRARIRR | 53 |
| DIM-PEP-327 | PFWRARIRR   PFWRARIRR | 153 |
| DIM-X-PEP-327 | PFWRARIRR X PFWRARIRR | 154 |
| R-DIM-PEP-327 | PFWRARIRR   RRIRARWFP | 155 |
| R-DIM-X-PEP-327 | PFWRARIRR X RRIRARWFP | 156 |
| PEP-328 | PFWRKRIRR | 54 |
| DIM-PEP-328 | PFWRKRIRR   PFWRKRIRR | 157 |
| DIM-X-PEP-328 | PFWRKRIRR X PFWRKRIRR | 158 |
| R-DIM-PEP-328 | PFWRKRIRR   RRIRKRWFP | 159 |
| R-DIM-X-PEP-328 | PFWRKRIRR X RRIRKRWFP | 160 |
| PEP-329 | PFWRKRLRR | 55 |
| DIM-PEP-329 | PFWRKRLRR   PFWRKRLRR | 161 |
| DIM-X-PEP-329 | PFWRKRLRR X PFWRKRLRR | 162 |
| R-DIM-PEP-329 | PFWRKRLRR   RRLRKRWFP | 163 |
| R-DIM-X-PEP-329 | PFWRKRLRR X RRLRKRWFP | 164 |
| PEP-330 | PFWRKKLKR | 82 |
| DIM-PEP-330 | PFWRKKLKR   PFWRKKLKR | 165 |
| DIM-X-PEP-330 | PFWRKKLKR X PFWRKKLKR | 166 |
| R-DIM-PEP-330 | PFWRKKLKR   RKLKKRWFP | 167 |
| R-DIM-X-PEP-330 | PFWRKKLKR X RKLKKRWFP | 168 |
| PEP-331 | PFWRKRWRR | 56 |
| DIM-PEP-331 | PFWRKRWRR   PFWRKRWRR | 169 |
| DIM-X-PEP-331 | PFWRKRWRR X PFWRKRWRR | 170 |
| R-DIM-PEP-331 | PFWRKRWRR   RRWRKRWFP | 171 |
| R-DIM-X-PEP-331 | PFWRKRWRR X RRWRKRWFP | 172 |
| PEP-332 | PFWRRRIRR | 57 |
| DIM-PEP-332 | PFWRRRIRR   PFWRRRIRR | 173 |
| DIM-X-PEP-332 | PFWRRRIRR X PFWRRRIRR | 174 |
| R-DIM-PEP-332 | PFWRRRIRR   RRIRRRWFP | 175 |
| R-DIM-X-PEP-332 | PFWRRRIRR X RRIRRRWFP | 176 |
| PEP-333 | PFWRRRWRR | 58 |
| DIM-PEP-333 | PFWRRRWRR   PFWRRRWRR | 177 |
| DIM-X-PEP-333 | PFWRRRWRR X PFWRRRWRR | 178 |
| R-DIM-PEP-333 | PFWRRRWRR   RRWRRRWFP | 179 |
| R-DIM-X-PE P-333 | PFWRRRWRR X RRWRRRWFP | 180 |
| PEP-334 | PWRIRIRR | 61 |
| DIM-PEP-334 | PWRIRIRR   PWRIRIRR | 181 |
| DIM-X-PEP-334 | PWRIRIRR X PWRIRIRR | 182 |
| R-DIM-PEP-334 | PWRIRIRR   RRIRIRWP | 183 |
| R-DIM-X-PEP-334 | PWRIRIRR X RRIRIRWP | 184 |
| PEP-335 | PWRRIRR | 83 |
| DIM-PEP-335 | PWRRIRR   PWRRIRR | 185 |
| DIM-X-PEP-335 | PWRRIRR X PWRRIRR | 186 |
| R-DIM-PEP-335 | PWRRIRR   RRIRRWP | 187 |
| R-DIM-X-PEP-335 | PWRRIRR X RRIRRWP | 188 |
| PEP-336 | PWRRKIRR | 84 |
| DIM-PEP-336 | PWRRKIRR   PWRRKIRR | 189 |
| DIM-X-PEP-336 | PWRRKIRR X PWRRKIRR | 190 |
| R-DIM-PEP-336 | PWRRKIRR   RRIKRRWP | 191 |
| R-DIM-X-PEP-336 | PWRRKIRR X RRIKRRWP | 192 |

-continued

| Designation | Sequence | SEQ ID No. |
|---|---|---|
| PEP-337 | PFWRRRIRIRR | 193 |
| DIM-PEP-337 | PFWRRRIRIRR PFWRRRIRIRR | 194 |
| DIM-X-PEP-337 | PFWRRRIRIRR X PFWRRRIRIRR | 195 |
| R-DIM-PEP-337 | PFWRRRIRIRR RRIRIRRWFP | 196 |
| R-DIM-X-PEP-337 | RRIRIRRWFP X RRIRIRRWFP | 197 |
| PEP-338 | RRWFFWRR | 198 |
| DIM-PEP-338 | RRWFFWRR RRWFFWRR | 199 |
| DIM-X-PEP-338 | RRWFFWRR X RRWFFWRR | 200 |
| R-DIM-PEP-338 | RRWFFWRR RRWFFWRR | 199 |
| R-DIM-X-PEP-338 | RRWFFWRR X RRWFFWRR | 200 |
| PEP-339 | RRWFWRR | 86 |
| DIM-PEP-339 | RRWFWRR RRWFWRR | 201 |
| DIM-X-PEP-339 | RRWFWRR X RRWFWRR | 202 |
| R-DIM-PEP-339 | RRWFWRR RRWFWRR | 201 |
| R-DIM-X-PEP-339 | RRWFWRR X RRWFWRR | 202 |

Preparation of Liposomes

Appropriate amounts of respective phospholipid stock solution were dried under a stream of nitrogen and stored in vacuum overnight to completely remove organic solvents. The dry lipid film was then dispersed in phosphate buffered saline (PBS, 20 mM NaPi, 130 mM NaCl, pH 7.4) and hydrated at a temperature well above the gel to fluid phase transition of the respective phospholipid under intermittent vigorous vortex-mixing. The lipid concentration was 0.1 weight % for calorimetric experiments. Hydration was carried out in presence or absence of peptides at a lipid to peptide ratio of 25:1 and 12.5:1 using a protocol described for POPS (Jimenez-Monreal, A. M. et al. Biochim Biophys Acta 1373(1998), 209-219), DPPS (Jing, W. et al. J Peptide Sci 11(2005), 735-743) and DPPC (Sevcsik, E. et al. Biochim Biophys Acta 1768 (2007) 2586-2596). The fully hydrated samples were stored at room temperature until measurement.

Differential Scanning Calorimetry (DSC)

DSC experiments were performed with a differential scanning calorimeter (VP-DSC) from MicroCal, Inc. (USA). Heating scans were performed at a scan rate of 30° C./h (pre-scan thermostating 30 min) with a final temperature of approximately 10° C. above the main transition temperature ($T_m$) and cooling scans at the same scan rate (pre-scan thermostating 1 min) with a final temperature approximately 20° C. below $T_m$. The heating/cooling cycle was performed three times. Enthalpies were calculated by integration of the peak areas after normalization to phospholipid concentration and baseline adjustment using the MicroCal Origin software (VP-DSC version). The phase transition temperature was defined as the temperature at the peak maximum (McElhaney, R. N. Chem Phys Lipids 30(1982), 229-259).

Circular Dichroism Spectroscopy

Measurements were performed on a Jasco J 715 Spectropolar-imeter (Jasco, Germany) at room temperature using quartz cuvettes with an optical path length of 0.02 cm. The CD spectra were measured between 260 nm and 180 nm with a 0.2 nm step resolution. To improve accuracy 5 scans were averaged. Peptides were dissolved in 10 mM Hepes (pH 7.4) to a final concentration of 100 µM. Spectra were measured in the absence and presence of 1 mM sodium dodecyl sulfate (SDS) and 1 mM dodecylphosphocholine (DPC) mimicking cancer and healthy mammalian membranes, respectively. The respective peptide to surfactant molar ratios were 1:25 and 1:100. Background signals were abstracted after measurements. Percentage secondary structure calculations were done using Dichroweb, CDSSR Convolution Program using reference set 4 (Whitmore, L. and Wallace, B. A. Biopolymers 89(2008), 392-400 and Nucleic Acids Res. 32 (2004), W668-W673.

Fluorescence Spectroscopy

Fluorescence spectroscopy experiments were performed using a SPEX Fluoro Max-3 spectrofluorimeter (Jobin-Yvon, France) and spectra were analyzed with Datamax software.

ANTS/DPX Leakage

Leakage of aqueous contents from liposomes was determined using the 8-aminonaphthalene-1,3,6-trisulfonic acid/p-xylene-bis-pyridinium bromide (ANTS/DPX) assay. Lipid films were hydrated with 12.5 mM ANTS, 45 mM DPX, 68 mM NaCl, 10 mM HEPES (4-(2-hydroxyethyl)-1-piperazineethanesulfonic acid) at pH 7.4 following a standard procedure.

Subsequently, the dispersions were extruded 20 times through a polycarbonate filter of 0.1 µm pore size to obtain LUVs. Unilamellarity and size were tested by X-ray and dynamic light scattering, respectively. The ANTS/DPX encapsulating vesicles were separated from free ANTS/DPX by exclusion chromatography using a column filled with Sephadex G-75 (Amersham Biosciences) fine gel swollen in an iso-smotic buffer (10 mM HEPES, 140 mM NaCl, pH 7.4). The void volume fractions were collected and the phospholipid concentration was determined by phosphate analysis (Broekhuyse, R. M. Biochim. Biophys. Acta 152 (2005), 307-315; Tao, T. and Cho, J. Biochemistry 18(1979), 2759-2765).

The fluorescence measurements were performed in 2 mL of the isosmotic buffer in a quartz cuvette at room temperature. Aliquots of LUVs were diluted with the iso-osmotic buffer to a final lipid concentration of 50 µM. Fluorescence spectra were obtained at 37° C. using an excitation wavelength of 360 nm and an emission wavelength of 530 nm and a slit width of 5 nm for both excitation and emission monochromators. Fluorescence emission was recorded as a function of time before and after the addition of incremental amounts of peptide. The fluorescence increase due to leakage and subsequent dilution of quenched dye was measured after addition of peptides. Peptides were added to final concentrations of 2, 4 and 8 µM, corresponding to peptide to lipid molar ratios of 1:25, 1:12.5 and 1:6.25, respectively.

Data are presented in terms of fluorescence intensity ($I_F$):

$$I_F = \frac{F - F_0}{F_{max} - F_0}$$

F is the measured fluorescence, $F_0$ the initial fluorescence without peptide and $F_{max}$ the fluorescence corresponding to 100% leakage gained by addition of 1% Triton X-100.

Tryptophan Quenching

Tryptophan fluorescence spectra were obtained at room temperature using an excitation wavelength of 282 nm and a slit width of 5 nm for excitation and emission monochromators. Quenching of Tryptophan was carried out in the presence and absence of phospholipid liposomes (lipid to peptide ratio 25:1) using 0.1, 0.4 and 0.7 M acrylamide. The data were analyzed according to the Stern-Volmer equation:

$$F_0/F = 1 + K_{SV}[Q]$$

where $F_0$ and F represent the fluorescence emission intensities in the absence and presence of the quencher molecule (Q) and $K_{SV}$ is the Stern-Volmer quenching constant, which is a quantitative measure for the accessibility of tryptophan to acrylamide (Tao, T. and Cho, J. Biochemistry 18(1979), 2759-2765).

Cell Lines and Culture

The primary human melanoma cell line SBcl2 and the metastatic melanoma WM164 were maintained in RPMI (Sigma) supplemented with 2% FBS, 2% L-glutamine and 1% Pen/Strep. Glioblastoma (U87-mg) purchased from CLS (Cell Line Service Heidelberg, Germany) and Rhabdomyosarcoma cell lines (TE671) purchased from ECAAC (Health Protection Agency Culture Collections Salisbury, UK) are cultured in Dulbecco's Modified Eagle Medium (DMEM) with addition of 2 mM Glutamine, 10% FBS (fetal bovine serum). Melanoma cell line A375 CLS (Cell Line Service Heidelberg, Germany) was cultured in Dulbecco's Modified Eagle Medium (DMEM)(PAA) with addition of 2 mM Glutamine and 10% FBS (fetal bovine serum. Human melanocytes used as healthy control cells: were isolated from the foreskin). The foreskin was cut into small pieces and incubated with 0.3% trypsin (PAA) overnight at 4° C. and for one hour at 37° C. Epidermis was separated. Cells were mechanically removed from the cell layer and centrifuged at 300 g for 3 min. The pellet was resuspended in melanocyte growth media (Biomedica). Melanocytes were further cultured in human melanocytes growth medium (PromoCell GmbH). Normal human dermal fibroblasts (NHDF) purchased from (PromoCell GmbH) were cultured in fibroblast growth medium 2 (PromoCell GmbH). All cells were kept in a 5% $CO_2$ atmosphere at 37° C. At 90% confluency cell-culture flasks were passaged with accutase. All cell cultures were periodically checked for mycoplasma.

PI-Uptake Assay

For detection of PI-uptake by fluorescence spectroscopy experiments were performed according to the following protocol.

Cells were collected, resuspended in media and diluted to a concentration of $10^6$ cells/ml. Aliquots of $10^5$ cells were incubated with peptides for up to 8 hours at 37° C. and 5% $CO_2$. PI was added and cells were again incubated for 5 min at room temperature in the dark. Excitation and emission wavelengths were 536 nm and 617 nm, respectively.

Cytotoxicity was calculated from the percentage of PI positive cells in media alone ($P_0$) and in the presence of peptide ($P_X$). Triton-X was used to determine 100% of PI positive cells ($P_{100}$).

$$\% \text{ PI-uptake} = \frac{100*(P_X - P_0)}{(P_{100} - P_0)}$$

For detection of PI-uptake by fluorescence microscopy experiments were performed on a Leica DMI6000 B with IMC in connection with a Leica DFC360 FX camera and AF 6000 software.

Cells (1-5×$10^4$) were seeded on Ibidi p-Slide 8 wells and grown in 300 µl media for 2-3 days to a confluent layer. Propidium iodide (PI, 2 µl of 50 µg/ml in PBS) was added to the well and cell status was checked after 5 min of incubation in the dark at room temperature. Then, peptides were added to the desired concentration and peptide effect was followed immediately. Pictures were taken every 5 or 15 min for up to 8 h from the same section of cells. Excitation and emission wavelength were as follows: PI excitation, 535 nm and emission, 617 nm.

MTS Viability Assay

Cell proliferation was measured by using a CellTiter 96 AQ nonradioactive cell proliferation assay (Promega). Cells were plated in 96-well plates and grown until confluence. Peptides were added to a final concentration of 5-100 µM. After incubation for 24 h at 37° C. (5% $CO_2$) MTS [3-(4, 5-dimethylthiazol-2yl)-5-(3-carboxymethoxyphenyl)-2-(4-sulfophenyl)-2H-tetrazolium]-phenozine methosulfate solution (20 µl/well) was added and cells were again incubated for 2 h at 37° C. (5% $CO_2$). The MIS compound is bioreduced by cells into a colored formazan product that is soluble in tissue culture medium. The quantity of the formazan product as measured by the amount of 490 nm absorbance is directly proportional to the number of living cells in culture. Data are calculated as a percentage of the control (untreated) samples and represent the average of three wells in one experiment which was repeated three times per cell line.

Spectrofluorimetric analysis of caspase-3/7 activity 5×$10^5$ cells/ml were seeded into 96-well plate and grown overnight at 37° C. and 5% $CO_2$. Cells were incubated with different concentrations of peptide for 4 hours. Apo-ONE® caspase-3/7 reagent was added in a 1:1 volume ratio and cells were incubated for 4 hours. Cells were then analyzed by fluorescence spectroscopy (GloMax®-Multi+ Microplate Multi-mode Reader with Instinc™). Untreated cells were used as negative control. Analysis was performed with Apo-ONE® Homogeneous Caspase-3/7 Assay (see FIG. 7).

Hemolysis

The hemolytic activity towards human red blood cells (RBCs), which were obtained from heparinized human blood, was determined by the release of hemoglobin following one hour incubation at 37° C. in MHNA (Mueller Hinton cation Non Adjusted). Percentage of hemolysis of RBCs was calculated using 1% Triton as 100% lysis and PBS as 0% lysis, peptide concentration was 500 µg/ml.

Results

In the present examples, toxicity, respectively selectivity of the peptides of the present invention against melanoma, rhabdomyosarcoma and glioblastoma cell lines that expose the negatively charged lipid phosphatidylserine on the outside was examined. Selective peptides are not toxic against normal non-tumor cells as melanocytes and fibroblasts or red blood cells in the same concentration range.

Selective and active peptides can be (retro-) isolated peptides (combination of the peptide moieties) of the present invention with or without linkers exhibiting defined secondary structures (as defined above) and show cancer selective activity in vitro and in cancer model systems.

Exemplarily 4 peptides were chosen to represent the observed effects. The results present data gained on peptide PEP-322 and PEP-318, representative for peptide moieties but non-active peptides, R-DIM-P-PEP-322 representative for cancer active and specific peptides and DIM-PEP-318 representative for cancer and non-cancer active, non-selective peptides (see Table 2).

Besides R-DIM-P-PEP-322 the peptides, DIM-PEP-322, R-DIM-PEP-322, R-DIM-PEP-316, R-DIM-PEP-323, DIM-PEP-324, R-DIM-P-PEP-324, R-DIM-P-PEP-332, R-DIM-P-PEP-334 were shown to be selective for cancer cells.

TABLE 2

Overview of peptide sequences, net charge and hydropho-bicity of the peptides examined

| | sequence | Net charge | $\Delta G_{wif}{}^a$ [kcal/mol] |
|---|---|---|---|
| PEP-322 | PFWRIRIRR (SEQ ID NO: 51) | +5 | n.d. |
| R-DIM-P-PEP-322 | PFWRIRIRRPRRIRIRWFP (SEQ ID NO: 128) | +9 | −2.00/−2.60 |
| PEP-318 | FWQRRIRRWRR (SEQ ID NO: 112) | +7 | n.d. |
| DIM-PEP-318 | FWQRRIRRWRRFWQRRIRRWRR (SEQ ID NO: 113) | +13 | −8.17/−7.91 |

$^a$Peptide hydrophobicity expressed as transfer free energy of peptides from water to bilayer interface ($\Delta G_{wif}$) calculated from the whole-residue hydrophobicity scale taking into account the contribution of the C-terminal amide (Wimley et al., Biochemistry 35 (1995), 5109-5124) and the % helix gained from the respective CD data Since for the short peptides PEP-322 and -318 the CD measurements are not accurate enough the $\Delta G_{wif}$ was only calculated for the isolated peptides.

Peptide Structure—Activity and Selectivity

In Silico—Secondary Structure Prediction

"Isolated peptides" of several PEP peptides were first analyzed by simulation of the secondary structure. The secondary structure of putative membrane active isolated peptides were predicted by the online program PEP-FOLD: http://bioserv.rpbs.univ-paris-diderot.fr/PEP-FOLD/ (Maupetit, J et al. Nucleic Acids Res. 37 (2009), W498-W503). From this analysis several peptides were selected for synthesis and activity studies according to their high proportion of amphipathic β-sheet or α-helical structure.

Figure 13:
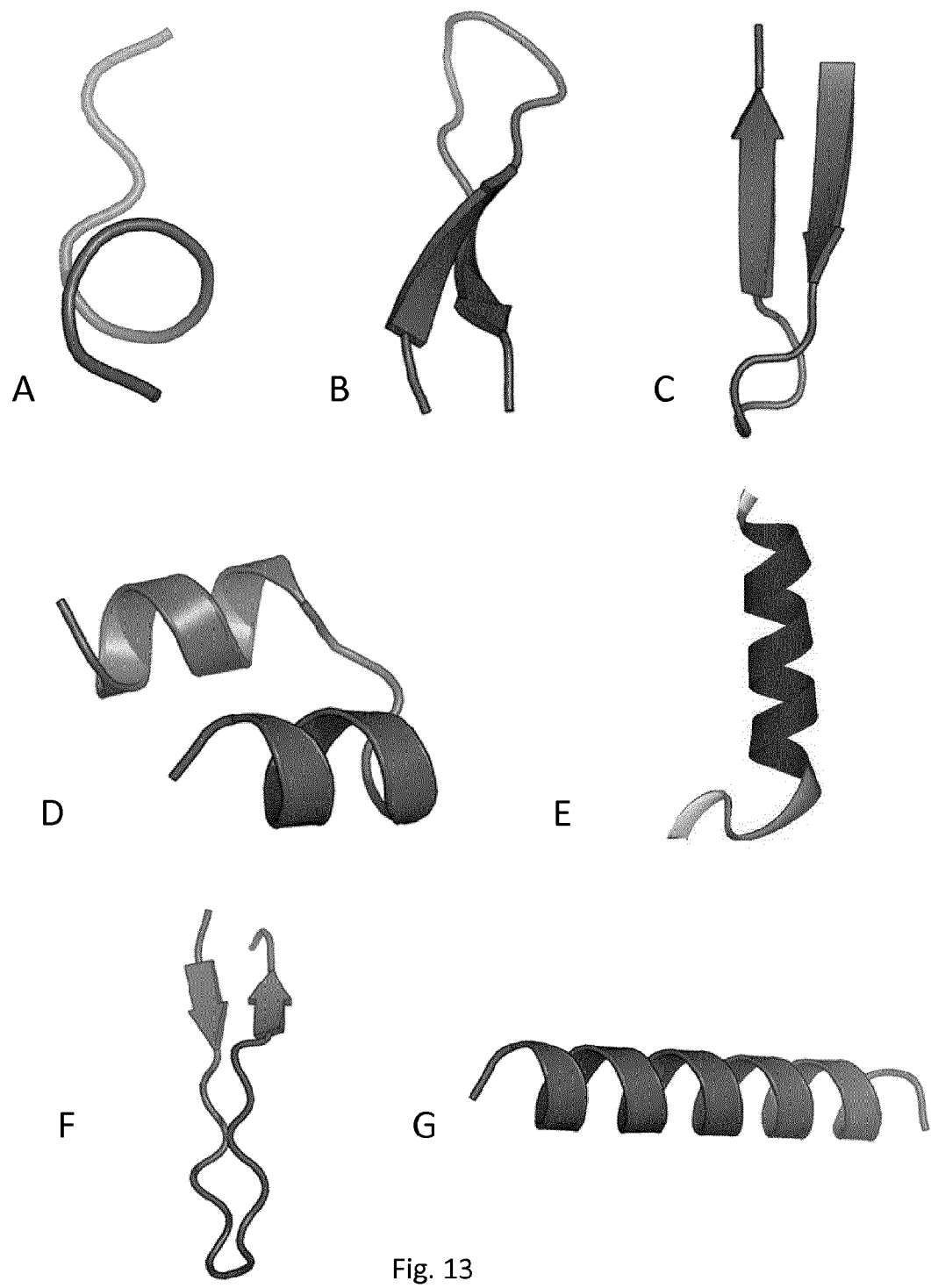
FIG. 13 shows secondary structure predictions of the peptides PEP-322 (A), R-DIM-P-PEP-322 (B), R-DIM-P-PEP-334 (C), R-DIM-PEP-316 (●), R-DIM-PEP-337 (E), DIM-PEP-324 (F) and DIM-318 (G), analyzed by the program PEP-FOLD.

The non-active peptide moieties partially turned out to be too short for assembly of a defined secondary structure. Interestingly the cancer specific peptides (DIM-, R-DIM-, R-DIM-P-PEP-322, DIM-PEP-324 and R-DIM-PEP-316) formed 2 β-strands or 2 α-helices (R-DIM-PEP-316) with a turn in the middle and distribution of cationic and hydrophobic regions. For the active but non-selective peptide DIM-PEP-318 a linear amphipathic α-helix without a loop was predicted (see Table 3, FIG. 13). For human Lactoferricin (hLFcin) (37-61) containing a disulfide bridge via Cys3 and Cys20 a structure with a helical and an extended part linked via a loop was predicted which is in agreement with the structure reported for hLFcin in a membrane mimetic solvent (Gifford, J L et al. Cell. Mol. Life Sci. 62 (2005), 2588-2598).

TABLE 3

List of secondary structure prediction and cancer specificity for isolated peptides (-retro); list includes all sequences in isolated peptide (DIM-) (peptide moiety sequence + peptide moiety sequence as defined herein), isolated peptide retro (R-DIM-) (peptide moiety sequence + peptide moiety retro sequence), isolated peptide with linker X (DIM-X-) (peptide moiety sequence + X + peptide moiety sequence), isolated peptide retro with linker X (R-DIM-X-) (peptide moiety sequence + X + peptide moiety retro sequence). H = helix, T = turn, β = β-strand. For positive or negative peptide specificity for tumor over non tumor cells in the case of studied peptides the respective -fold specificity for melanoma (SBcl2 or A375) over non tumor skin cells (melanocytes or normal human dermal fibroblasts (NHDF-c)) at 20 μM peptide concentration after 8 hours incubation is listed (derived by PI uptake studies).

| peptide moieties | Secondary Structure Prediction | | | | Cancer |
|---|---|---|---|---|---|
| (parents) | DIM- | DIM-X- | R-DIM- | R-DIM-X- | Specificity |
| PEP | H | 2H T | H | 2H T | |
| PEP-313 | H T | 2β T | H | H T β | |
| PEP-314 | 2H | 2β T | 3β 2T | 2β T | |
| PEP-315 | H | 2H T | H | 2H T | |
| PEP-316 | H T | 2H T | 2H T | 2H T | Yes (15fold) (R-DIM-) |
| PEP-317 | H | 2H T | H | 2H T | |
| PEP-318 | H | 2H T | H | 2H T | No (<1fold) (DIM-) |
| PEP-319 | 2H T | 2H T | H | 2H T | |
| PEP-320 | H | 2H T | 2H T | 2H T | |
| PEP-322 | 2β T | 2β T | 2β T | 2β T | yes (50fold) (DIM-), 20fold (R-DIM-), >100fold (R-DIM-X-) |
| PEP-215 | 2β T | 2β T | 2β T | 2β T | |
| PEP-227 | 2H | 2H T | H | 2H T | |
| PEP-323 | 2 β T | 2β T | 2β T | 4β T | |
| PEP-324 | 2β T | 2β T | 2β T | 2β T | yes (7fold) (DIM-), (15fold) (R-DIM-X-) |
| PEP-325 | 2H T | 2H T | H | 2H T | |
| PEP-326 | 2H T | 2H T | H | 2H T | |
| PEP-327 | 2H T | 2H T | H | 2H T | |
| PEP-328 | 2H | 2H T | H | 2H T | |
| PEP-329 | 2H | 2H T | H | 2H T | |
| PEP-330 | 2H | 2H T | H | 2H T | |
| PEP-331 | 2H | 2H T | H | 2H T | |
| PEP-332 | 2H | 2H T | H | 2H T | (5fold) (R-DIM-X-) |
| PEP-333 | 2H | 2H T | H | 2 H T | |
| PEP-334 | 2β T | 2β T | 2β T | 2β T | (15fold) (R-DIM-X-) |
| PEP-335 | 2H | 2H T | H | 2H T | |
| PEP-336 | H | 2H T | H | 2H T | |
| PEP-337 | 2H T | 2H T | H | 2H T | weak (2fold) (R-DIM-) |
| PEP-338 | 2β T | 2β T | =DIM- | =DIM-X- | |
| PEP-339 | 2β T | 2β T | =DIM- | =DIM-X- | |

Model Studies

Circular Dichroism Spectroscopy—Secondary Structure Vs. Activity and Selectivity Strikingly the selective peptide R-DIM-P-PEP-322 (FIG. 1B) exhibits a significant increase of β-sheet conformation in the presence of the cancer mimic SDS, α-helical content is even further decreased. Moreover the structure of the peptide in the presence of the healthy mimic DPC is the same as in solution, giving further hint for the cancer selective toxicity of these peptides (see also FIG. 2).

Percentage secondary structure calculations were done using Dichroweb, CDSSR Convolution Program using reference set 4 (Whitmore et al., Nucleic Acids Res. 32 (2004), W668-W67; Whitmore et al., Biopolymers 89 (2008), 392-400). The α-helical content is shown in dark gray at the bottom; β-turns in light grey; turns in middle grey; random coil structures in dark grey at the top.

FIG. 2 now presents the results of circular dichroism spectroscopy of the non-specific peptide DIM-PEP-318 in contrast to the specific peptide R-DIM-PEP-322. In contrast to the PEP-322 peptide group, DIM-PEP-318 possesses a higher α-helical content in the presence of the cancer mimic SDS as well as in the presence of the non-cancer mimic DPC. DIM-PEP-318 adopts up to 75% α-helical structure without discrimination between cancer and non-cancer cell mimic.

In Vitro Studies—Membrane Permeabilization

PI-Uptake—Increase of Activity by Sequence Doubling

Figure 3:
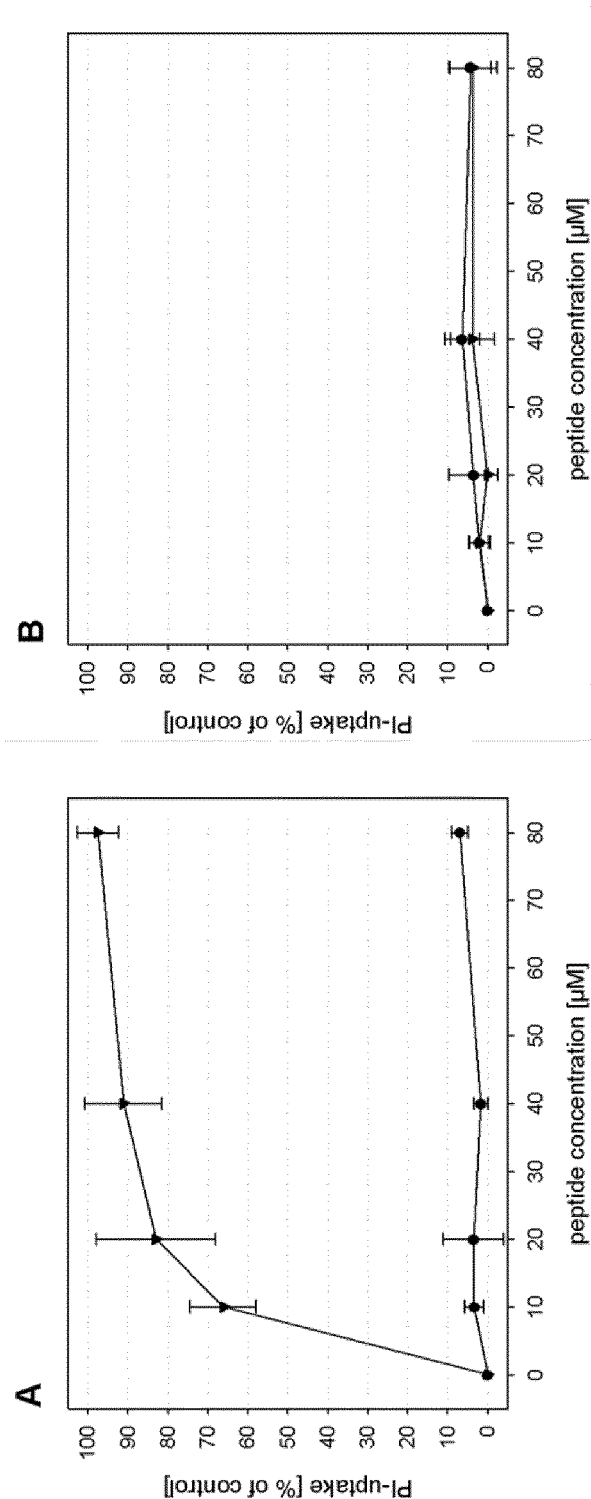
FIG. 3 shows peptide toxicity-PI-uptake of cancer and non-cancer cell lines: (A) Concentration dependent cytotoxic activity of PEP-322 (●) and R-DIM-P-PEP-322 (▼) against melanoma cell line SBcl-2 after 8 hours of incubation with peptides; (B) Concentration dependent cytotoxic activity against primary cultures of differentiated non-tumorigenic melanocytes after 8 hour of incubation with peptides; (C) specificity of peptides at 20 μM peptide concentration after 8 h of incubation displayed as PI-uptake ratio of SBcl-2 vs. melanocytes and WM164 vs. melanocytes.
Figure 3:
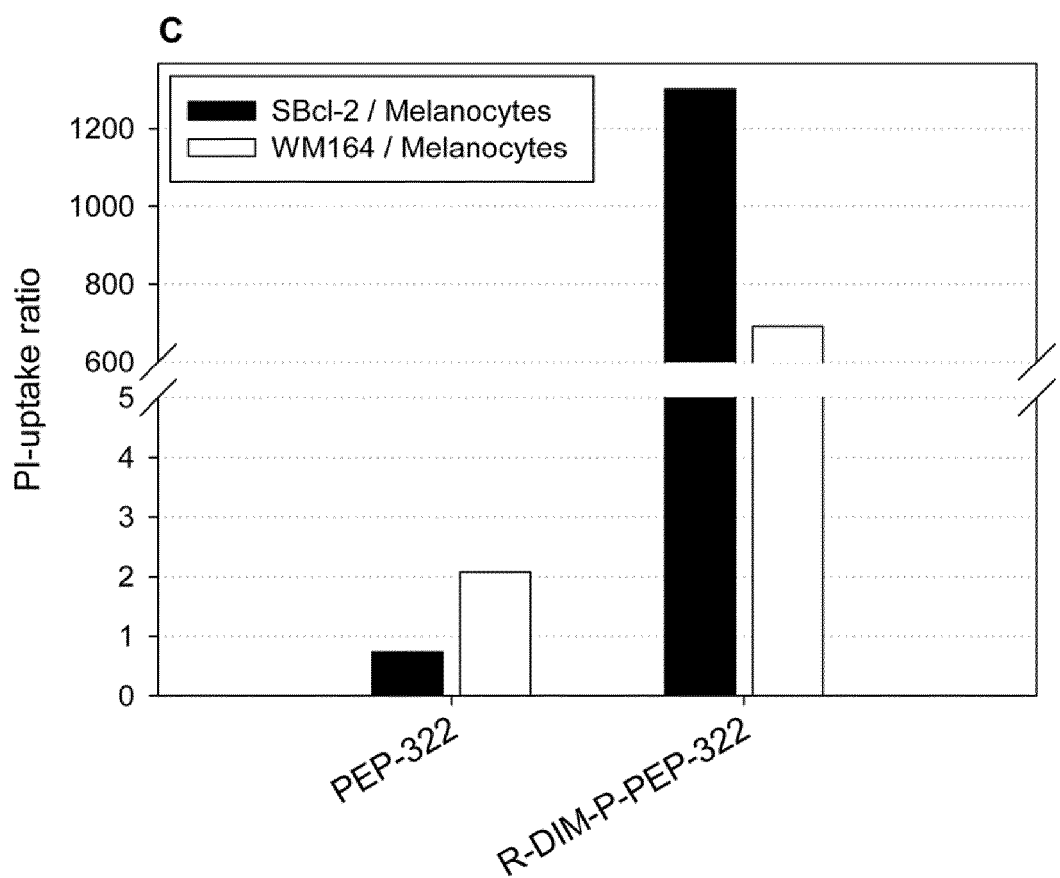

Cytotoxic activity of the peptides towards melanoma cells of primary (SBcl-2) and metastatic lesions (WM164) and differentiated non-tumorigenic melanocytes was determined by measurement of PI-uptake, which only occurs when integrity of the cell membrane is lost. Cells were incubated in media containing serum for 8 h in the presence of peptides. Peptide concentrations were varied from 10 to 80 μM. FIG. 3 illustrates that the peptide moiety PEP-322 is only minor active against the melanoma cell line SBcl-2 with less than 5% killing at a peptide concentration of 80 μM, as well as against melanocytes with a moderate two-fold selectivity for WM164 cells at 20 μM peptide concentration (FIG. 3C). The isolated peptide by combination of the peptide moiety with its retro sequence and a Pro linker R-DIM-P-PEP-322 shows strongly increased activity against SBcl-2 compared to the its peptide moiety with very high specificity for the melanoma cell line. Already at a peptide concentrations of 20 μM, R-DIM-P-PEP-322 yields more than 80% PI positive SBcl-2 cells, while only less than 1% of differentiated non-tumorigenic melanocytes are killed (FIG. 3B), exhibiting a specificity more than 100-fold for cancer cells (see FIG. 3C). The second melanoma cell line, WM164, tested at 20 μM R-DIM-P-PEP-322 peptide concentration is also highly sensitive for the peptide.

Figure 4:
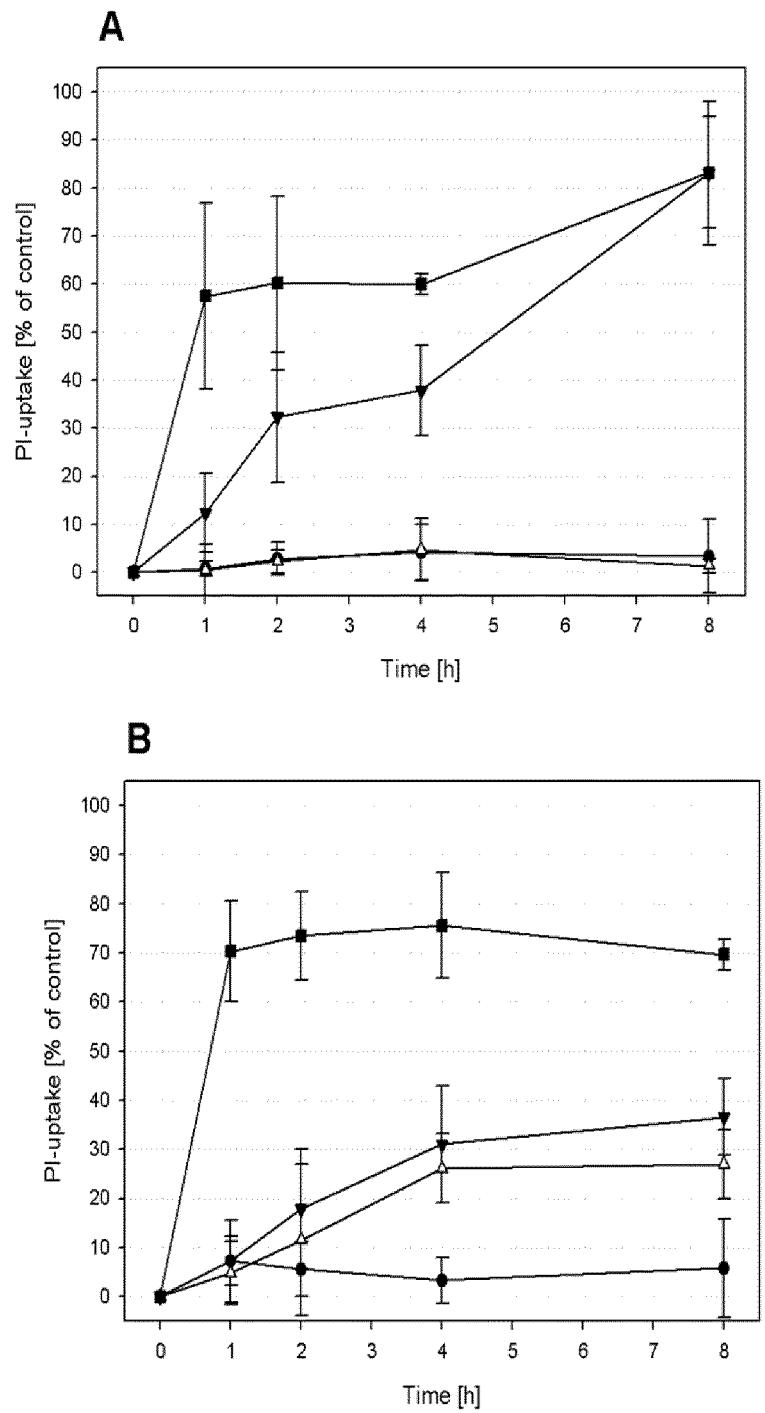
FIG. 4 shows PI-uptake of various cancerous and non-cancerous cell lines upon incubation with 20 μM peptide: Time dependent cytotoxic activity of PEP-322 (●), R-DIM-P-PEP-322 (▼), PEP-318 (Δ) and DIM-PEP-318 (■) against melanoma cell line SBcl-(A), melanoma metastasis WM164 (B), Rhabdomyosarcoma cell line TE671 (C), differentiated non-tumorigenic melanocytes cell lines (D) and normal human dermal fibroblast cell line NHDF (E) at 20 µM peptide concentration is shown.
Figure 4:
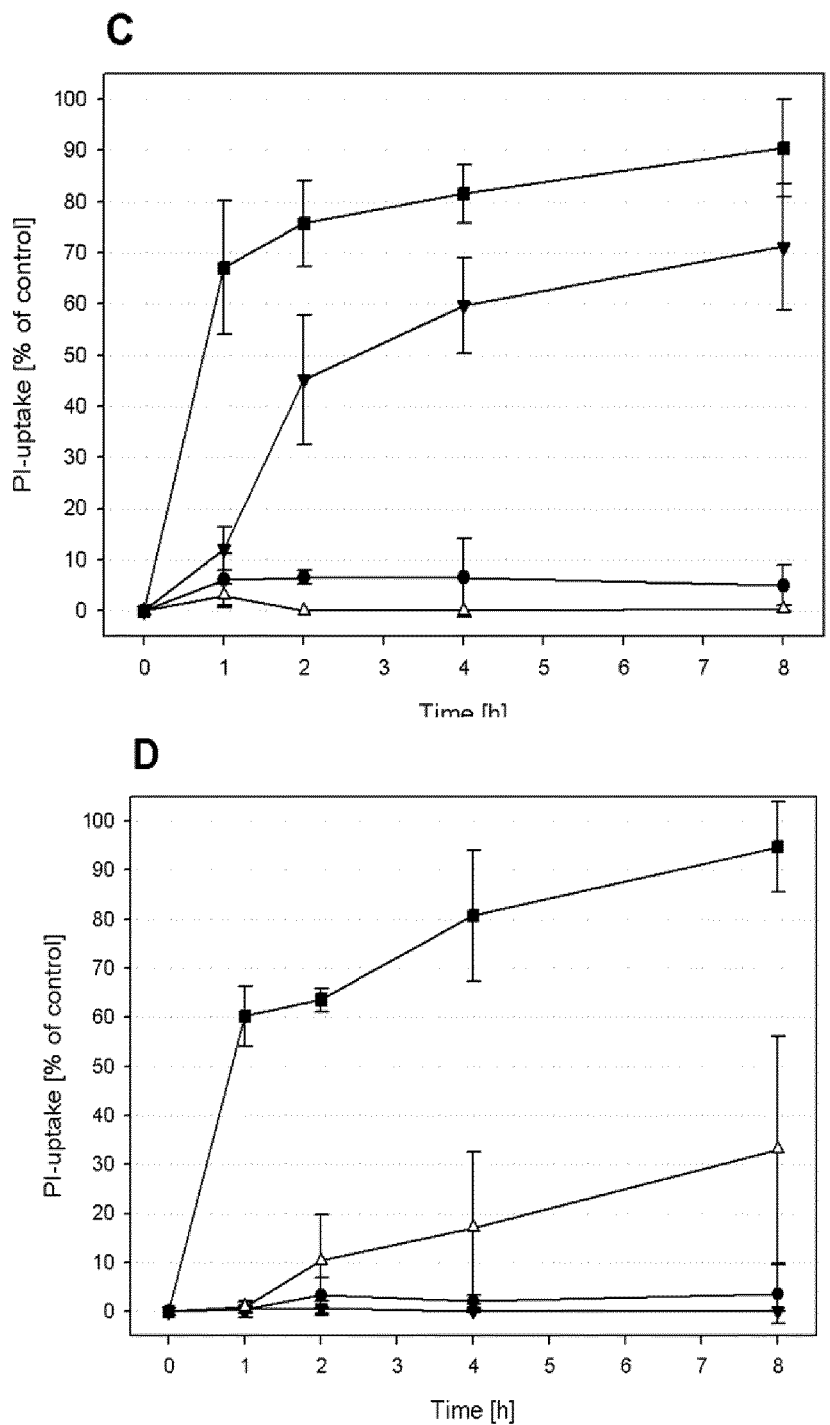
Figure 4:
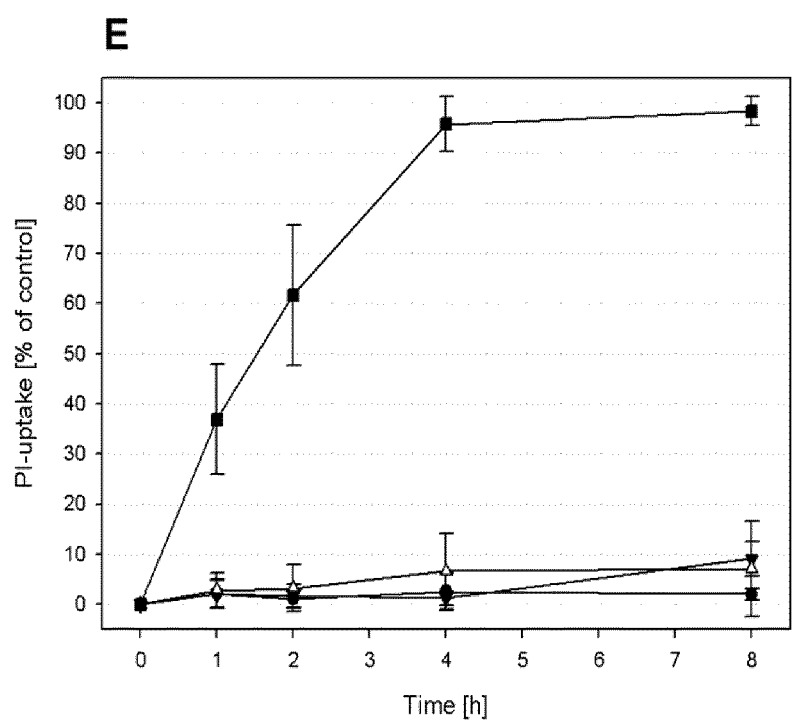
Figure 5:
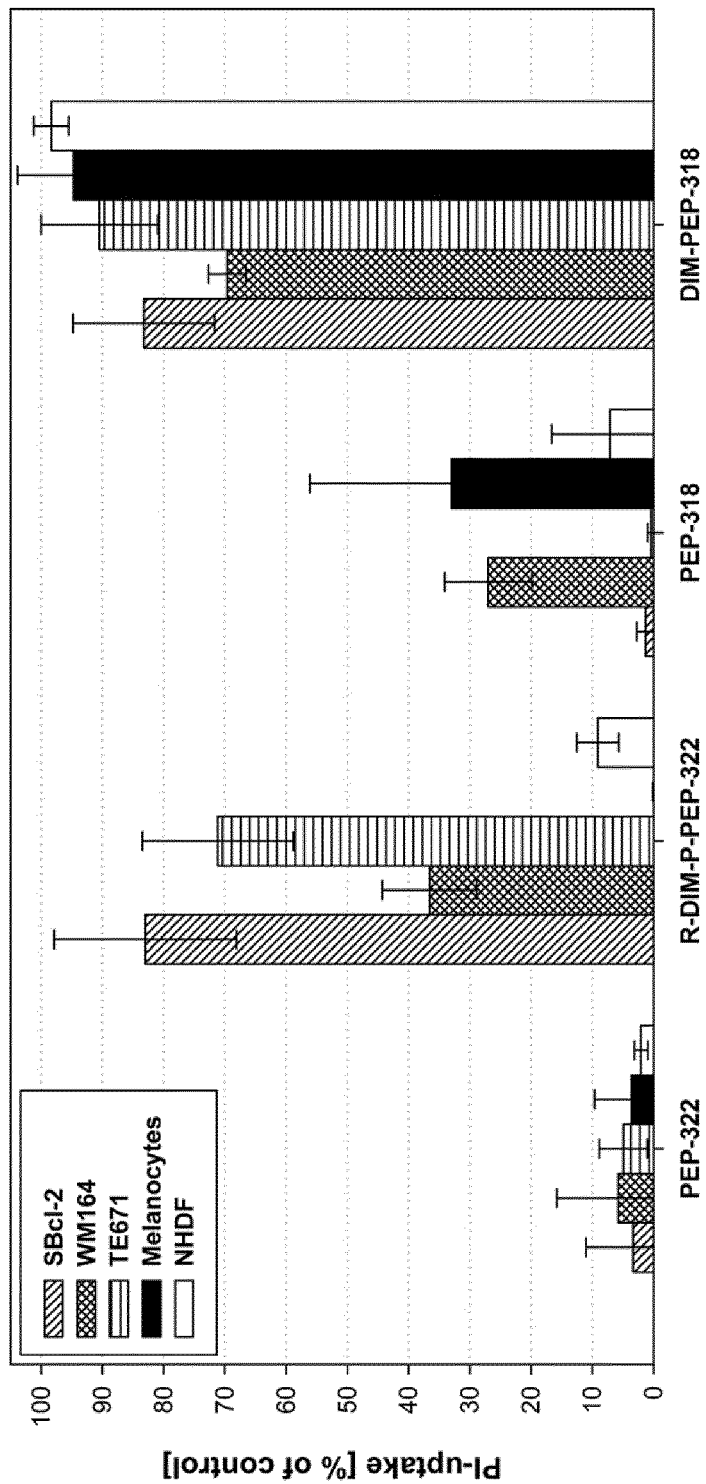
FIG. 5 shows cytotoxicity of peptides after 8 h of incubation against SBcl-2 melanoma cell line, WM164 melanoma metastasis, TE671 rhabdomyosarcoma cell line, differentiated non-tumorigenic melanocyte cell line and NHDF normal human dermal fibroblast cell line.

PI-Uptake—Specificity and Time Dependence of Killing-Correlation of Specificity with Structure Cytotoxic activity of the peptides towards melanoma cells of primary (SBcl-2) and metastatic lesions (WM164), a rhabdomyosarcoma cell line (TE671) and their healthy counterparts differentiated non-tumorigenic melanocytes and normal human dermal fibroblasts (NHDF) was determined by measurement of PI-uptake, which indicates a loss of cell membrane integrity (FIGS. 4 and 5). Cells were incubated in media containing serum for up to 8 h in the presence of peptides at 20 μM peptide concentration.

Figure 11:
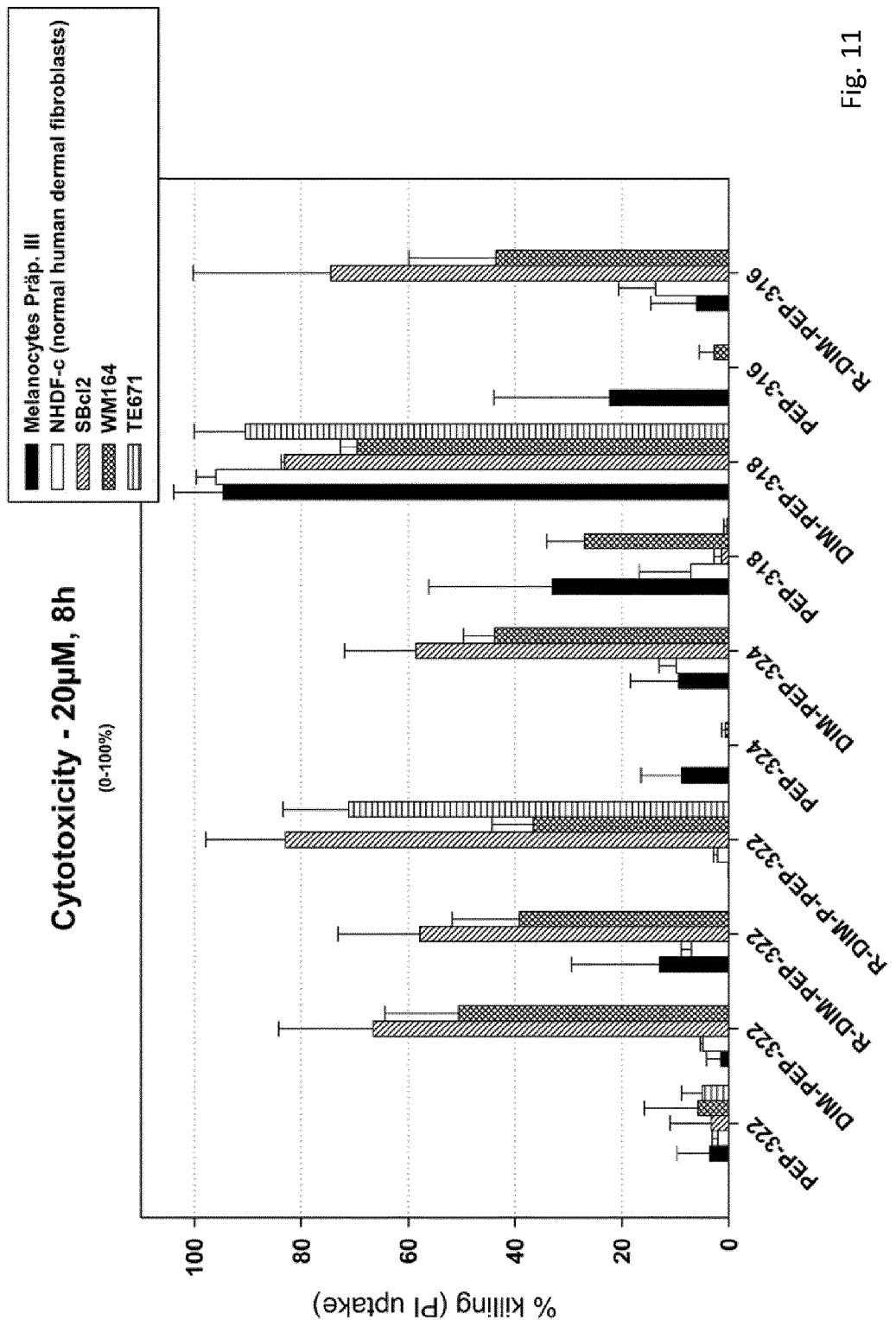
Figure 12:
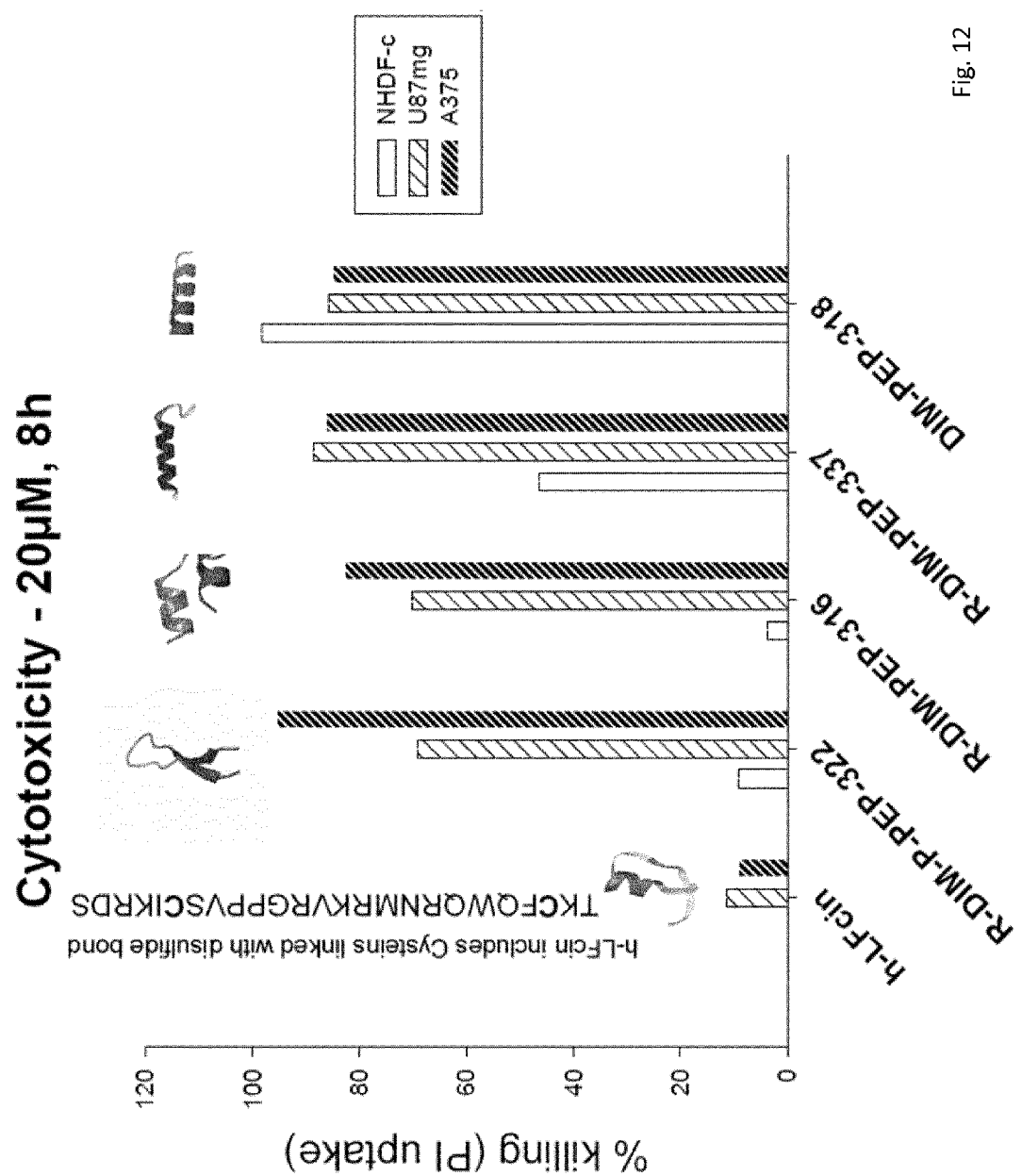
FIG. 12 shows cytotoxicity of specific peptides R-DIM-P-PEP-322 and R-DIM-PEP-316 and less specific peptides R-DIM-PEP-337 and DIM-PEP-318 and weakly active human Lactoferricin (hLFcin) (37-61), which contains two cysteins (Cys3 and Cys20) connected via a disulfide bond, after 8 h of incubation, respectively, against U87 mg glioblastoma cell line, A375 melanoma cell line and NHDF-c normal human dermal fibroblast cell line and PEP-FOLD secondary structure predictions of peptides.

Both peptide moieties PEP-322 as well as PEP-318 are only minor active against cancer cells (<30%, see FIG. 4A-C). However, PEP-318 is even slightly active against non-cancer cells, killing up to ~30% of NHDF. Interestingly, the combination of the peptide moiety PEP-322 and its retro sequence in form of the isolated peptide R-DIM-P-PEP-322 shows high cancer toxicity (up to 80%) but with negligible non-cancer toxicity (see FIG. 4D-E). In contrast to DIM-PEP-318, R-DIM-P-PEP-322 kills quite slowly reaching its highest activity not before 4-8 h. The second peptide moiety combination, namely DIM-PEP-318, possesses the highest and fastest anticancer activity with up to 90% killing within minutes (FIG. 4A-C). However, DIM-PEP-318 reveals to be quite unspecific since it is also highly active against differentiated non-tumorigenic melanocytes as well as against normal human dermal fibroblasts (FIG. 4D-E). Cytotoxic activity of the peptides after 8 h of incubation is given in FIG. 11. As can be seen in FIG. 12 all peptides with structure predictions of an α-helix without a loop exhibit toxicity against non-tumor and tumor cell lines. The parent peptide hLFcin (37-61) comprising contrary to the peptides claimed here within a disulfide bond via two cysteines (Cys3 and Cys20) shows only weak activity against the tested melanoma cell line A375 and glioblastoma cell line U87 mg and no toxicity against normal human dermal fibroblasts NHDF-c.

Figure 14:
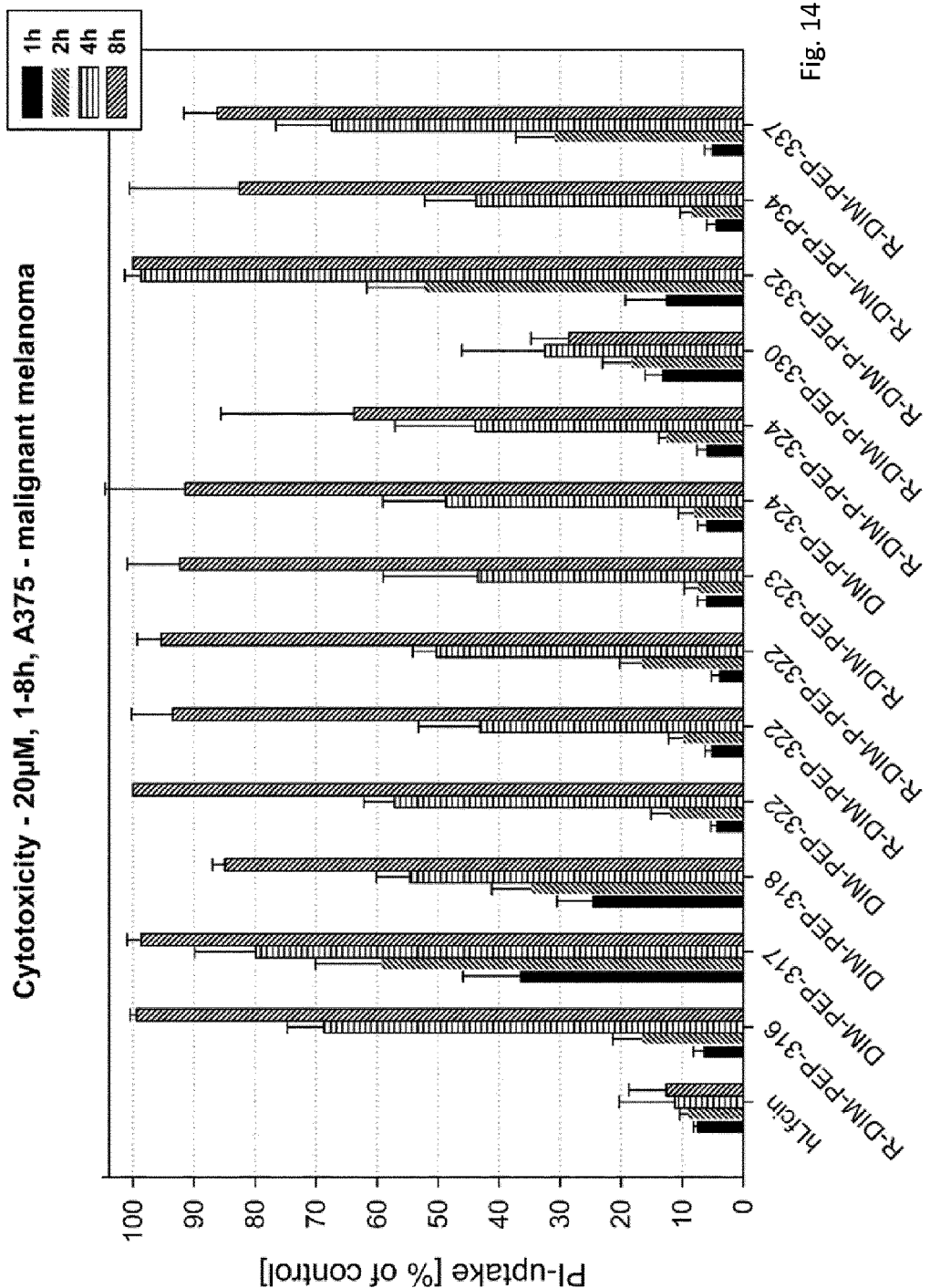
FIG. 14 shows cytotoxicity of peptides R-DIM-P-PEP-316, DIM-PEP-317, DIM-PEP-318, DIM-PEP-322, R-DIM-PEP-322, R-DIM-P-PEP-322, R-DIM-PEP-323, DIM-PEP-324, R-DIM-PEP-324, R-DIM-P-PEP-330, R-DIM-P-PEP-332, R-DIM-P-PEP-334 and R-DIM-PEP-337 and human Lactoferricin (hLFcin)(37-61) after 1 h, 2 h, 4 h and h of incubation, respectively, against A375 melanoma cell line.

As shown in FIGS. 14 and 15 the isolated peptides show high cytotoxicity against the cell lines of malignant melanoma (A375) and glioblastoma (U87 mg) after 8 hours of incubation at 20 μM peptide concentration. The cytotoxicity is very much improved compared to that exhibited by the parent peptide h LFcin. These two cancer types exhibit so far very poor treatability and bad prognosis.

Cell Viability—MTS Cell Proliferation

Figure 6:
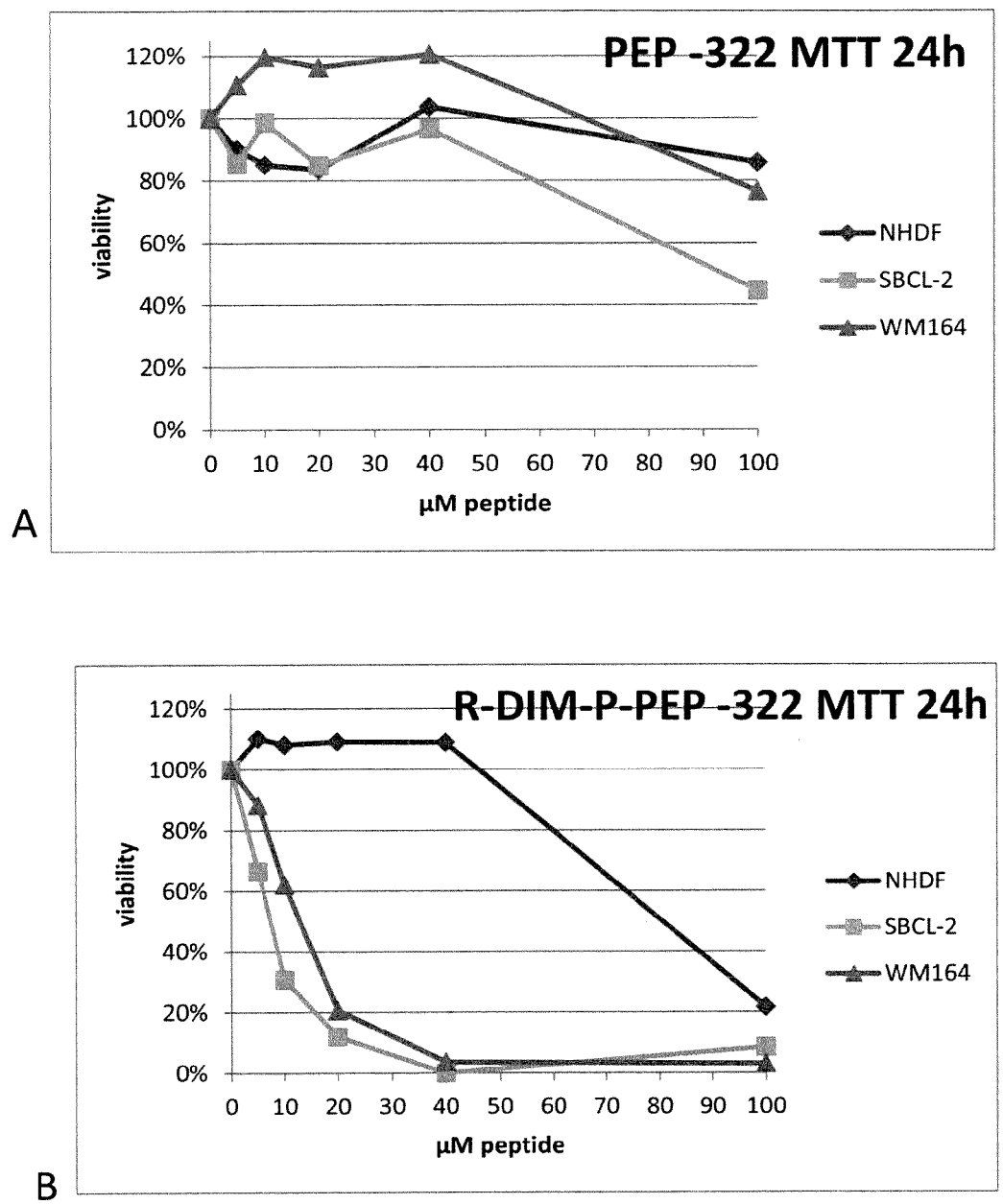
FIG. 6 shows cytotoxic activity of PEP-322 (A), R-DIM-P-PEP-322 (B) and DIM-PEP-318 (C) determined by MTS cell proliferation assay against melanoma cell line SBcl-2 melanoma metastasis WM164 and non-cancer human dermal fibroblasts (NHDF). Cells were kept in the appropriate medium during incubation time of 24 h.
Figure 6:
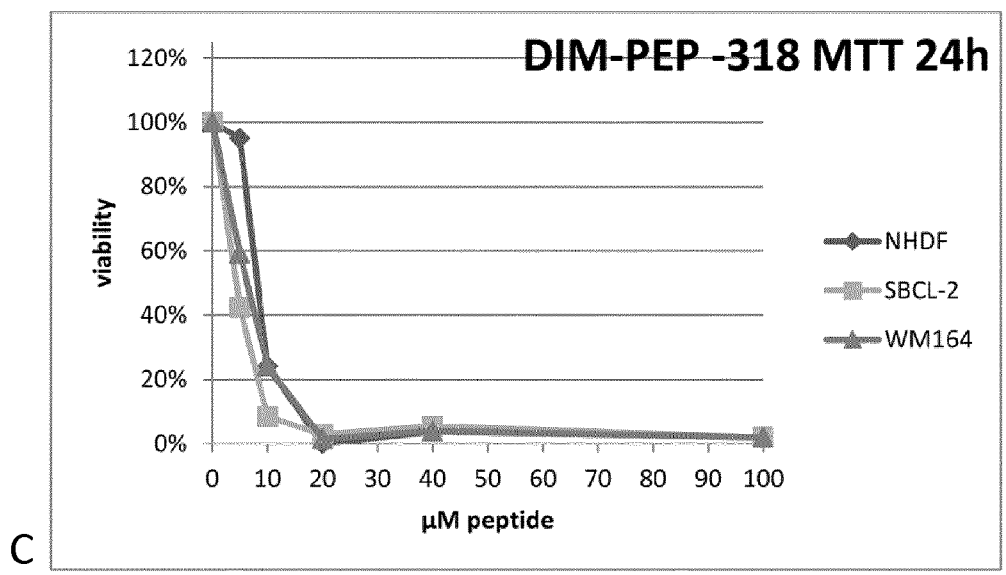

To determine long-time toxicity of peptides, a MTS cell proliferation assay was used to elucidate cell viability upon 24 h incubation with variant peptide concentration and human melanoma cell lines SBcl-2 and WM164 and non-differentiated human skin fibroblast cell line NHDF. As shown in FIG. 6A PEP-322 affects cancer cells and non-cancer cells only marginally even at higher peptide concentrations of 100 μM sustaining more than 70% cell viability ($IC_{50\ WM164\ and\ NHDF}$>100 μM) and 40% ($IC_{50\ SBcl-2}$ 90). Combination of peptide moieties could highly improve anticancer activity. R-DIM-P-PEP-322 exhibits a decreased $IC_{50}$ value of 8 μM and 15 μM for melanoma cell line SBcl-2 and melanoma metastasis WM164, respectively (FIG. 6B) compared to an $IC_{50}$ value of 80 μM for the non-cancer cell line, yielding 8-5-fold selectivity for cancer cells. DIM-PEP-318 shows also high activity against cancer cells resulting in an $IC_{50}$<10 μM (FIG. 6C). As indicated already by PI uptake studies this peptide is as toxic for non-cancer cells, revealed by a very low $IC_{50}$ of 10 μM for NHDF, as well. Results of MTS and PI assay with cancer cells correlated well. An overview of $IC_{50}$ values is given in Table 6.

TABLE 6

Comparison of $IC_{50}$ values determined through PI-uptake (8 h) and MTS cell viability assay (24 h).

|  | SBcl-2 (PI/MTS) | Fibroblasts (PI/MTS) |
| --- | --- | --- |
| PEP-322 | >80 μM/90 μM | >>80 μM/>100 μM |
| R-DIM-P-PEP-322 | 8 μM/8 μM | >>80 μM/80 μM |
| PEP-318 | n.d./n.d. | n.d./n.d. |
| DIM-PEP-318 | <20 μM/6 μM | <20 μM/10 μM |

Hemolytic Activity Against Red Blood Cells—Specificity

Hemolytic activity of peptides against red blood cells was tested at 500 μg/ml peptide and 2.5% red blood cell concentration. It was very surprising that DIM-PEP-318 was not hemolytic, considering the high toxicity towards melanocytes and fibroblasts.

TABLE 7

Hemolytic activity of peptides against human red blood cells

|  | % lysis of 2.5% RBCs[a] | $IC_{50}$ [μg/ml] |
| --- | --- | --- |
| PEP-322 | 2[b] | >500[b] |
| R-DIM-P-PEP-322 | 0.84+ 0.63 | >500 |
| PEP-318 | n.d. | n.d. |
| DIM-PEP-318 | 2.87+ 0.57 | >500 |

Figure 7:
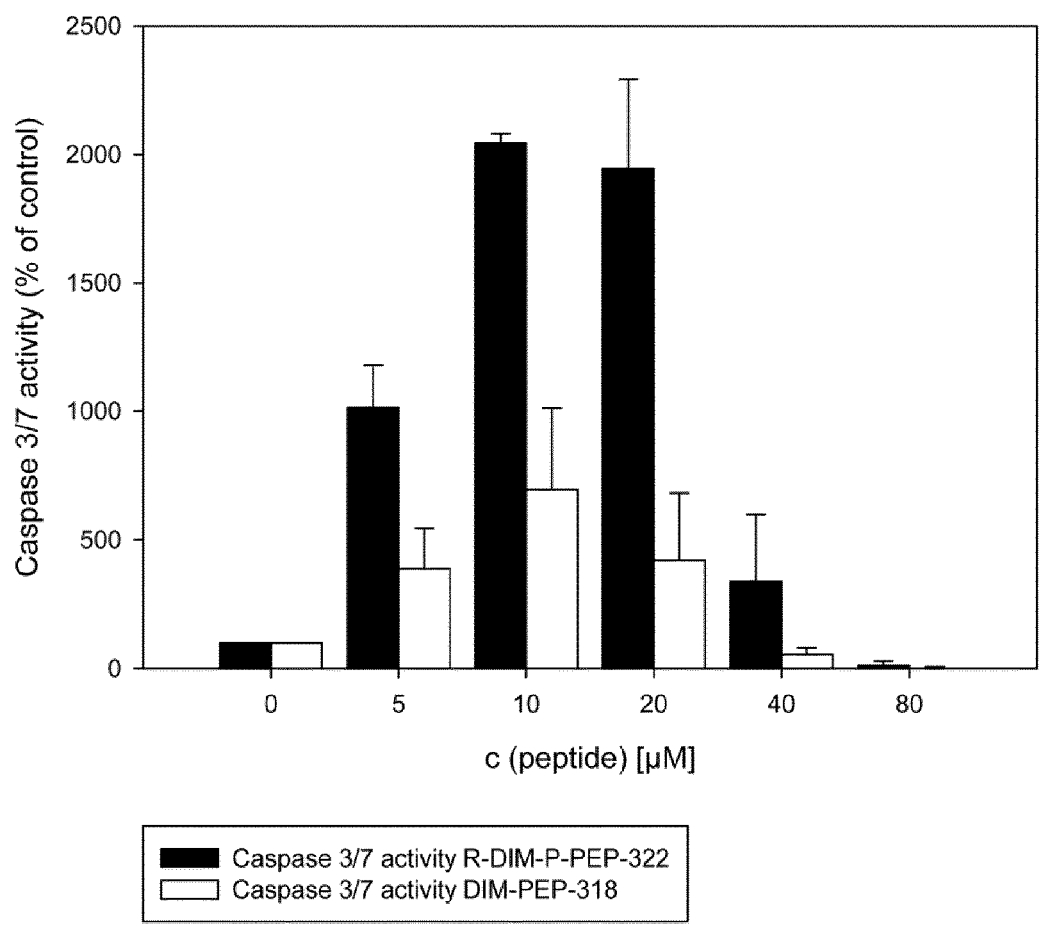
FIG. 7 shows spectrofluorimetric analysis of Caspase 3/7-activity of melanoma cell line SBcl-2 upon incubation of 4 h with different concentrations (5 µM, 10 µM, 20 µM, 40 µM, 80 µM) of peptide R-DIM-P-PEP-322 (black) and DIM-PEP-318 (white).
Figure 8:
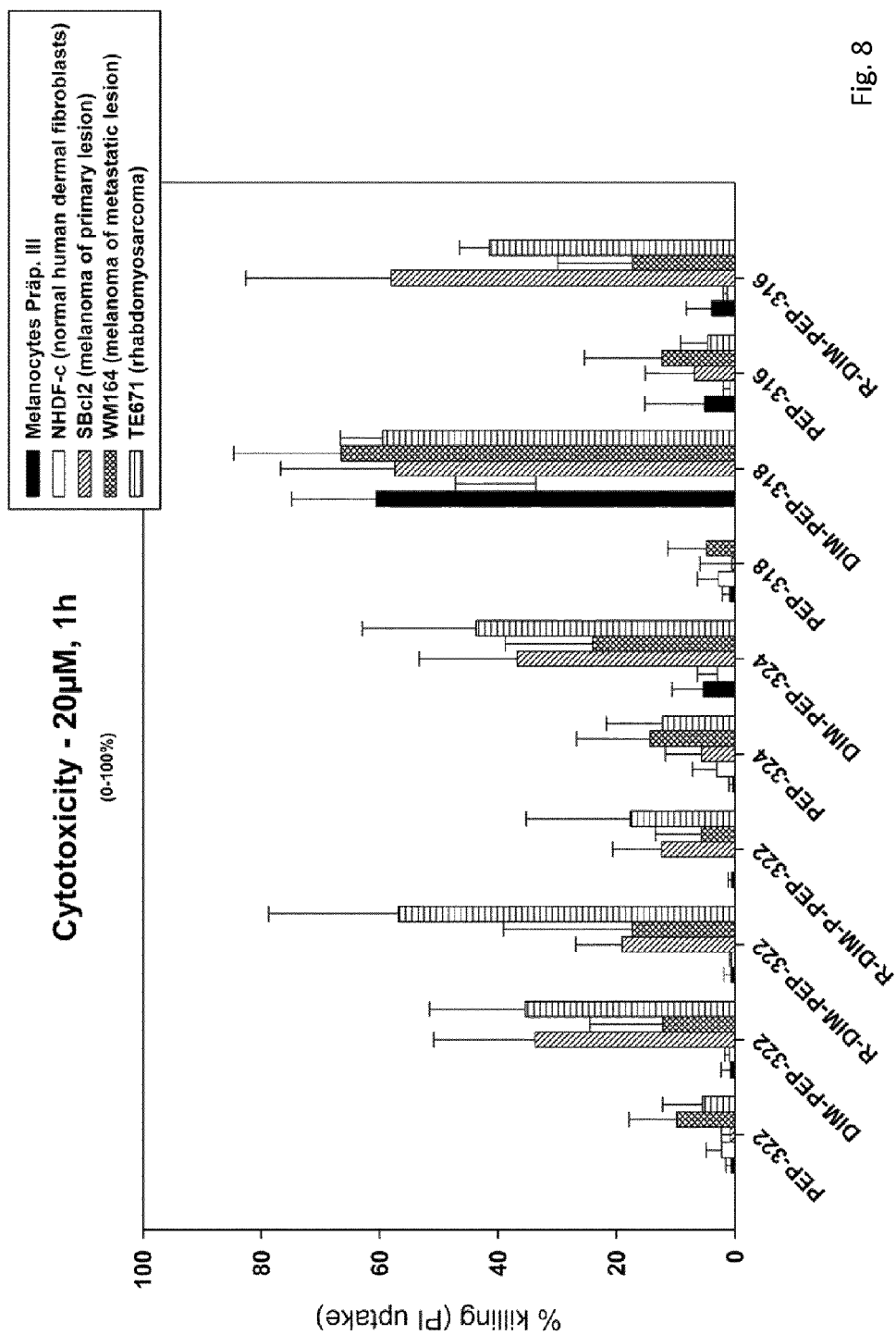
FIGS. 8 to 11 show cytotoxicity of peptides after 1 h, 2 h, 4 h and 8 h of incubation, respectively, against SBcl-2 melanoma cell line, WM164 melanoma metastasis, TE671 rhabdomyosarcoma cell line, differentiated non-tumorigenic melanocyte cell line and NHDF normal human dermal fibroblast cell line.
Figure 9:
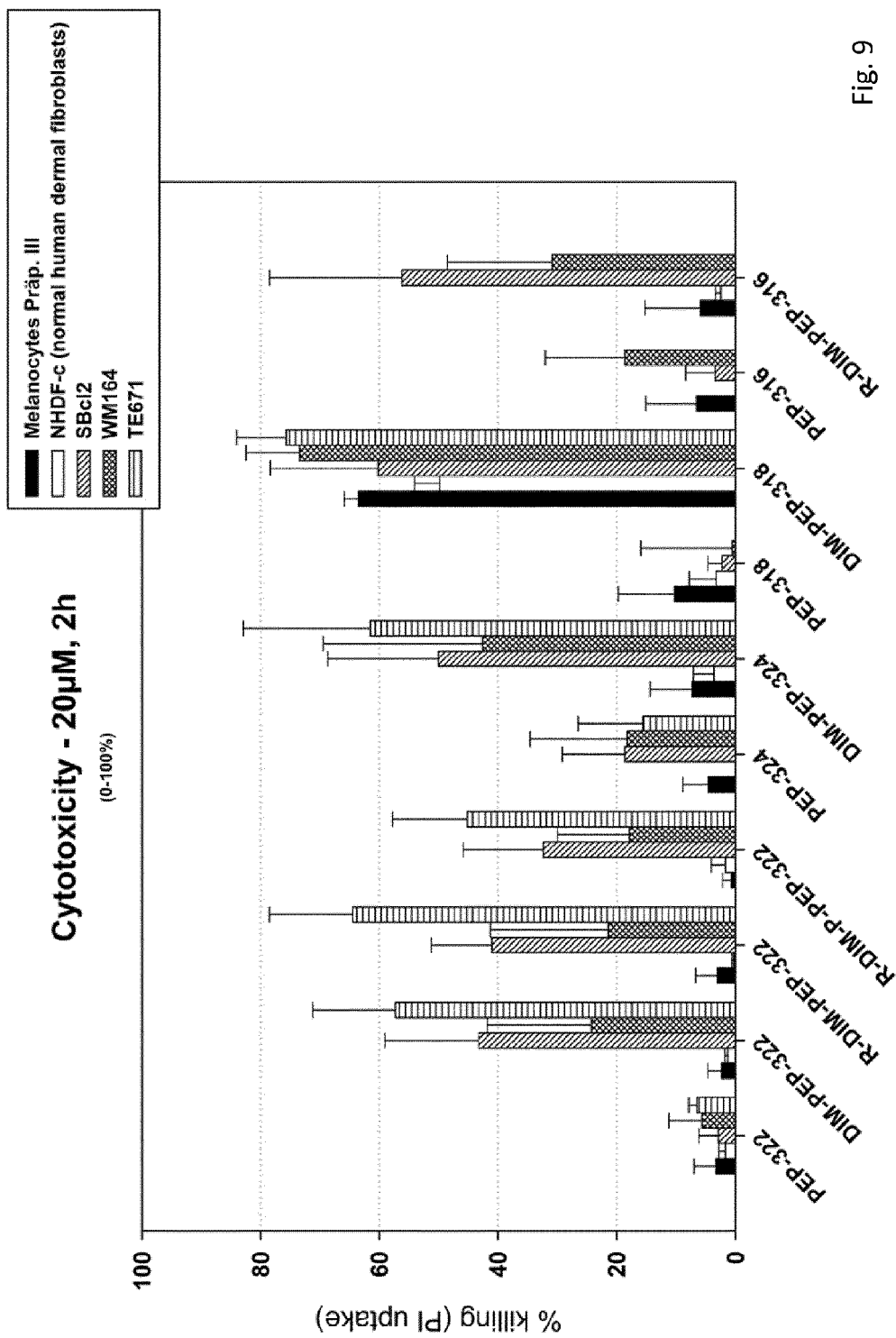
Figure 10:
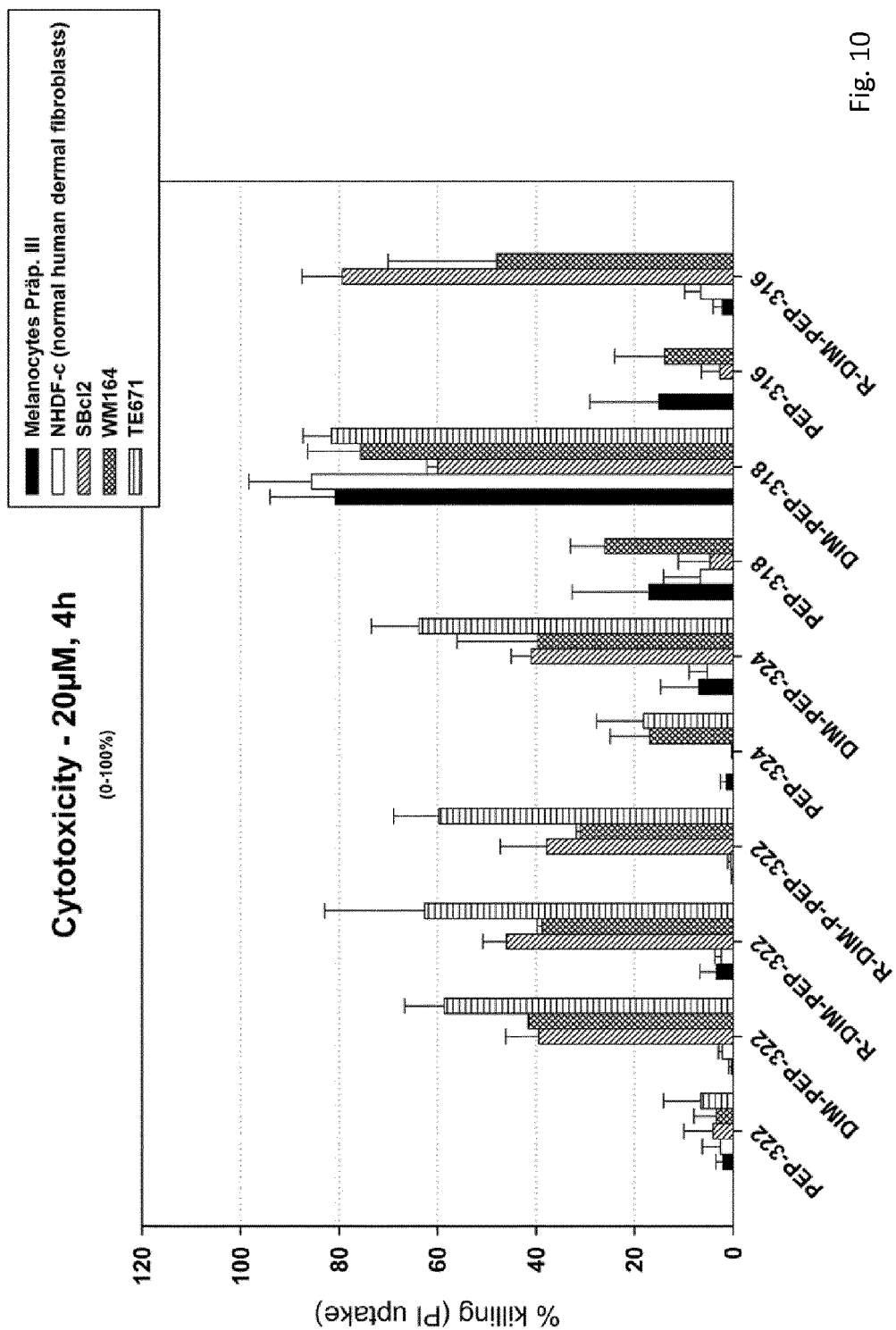

[a]Percentage of hemolysis of human red blood cells (RBCS) was calculated following one hour incubation at 37° C. in PBS using 1% Triton X-100 as 100% lysis and PBS as 0% lysis, peptide concentration was 500 μg/ml.
[b]from Zweytick et al., J. Biol. Chem. 286 (2011),.
n.d. not determined Caspase-3 Cleavage-Apoptosis or Necrosis To clearly differentiate between necrotic and apoptotic killing a caspase-3/7 activity assay was used to detect emergence of apoptosis (FIG. 7). R-DIM-P-PEP-322 showed apoptosis indicated by a strong increase of caspase- 3/7 activity from the time-point of 4 hours of incubation of melanoma cells SBcl-2 with 10-20 µM peptide, indicated by a 200-fold increase of green fluorescence. The non-specific peptide DIM-PEP-318 showed much lower caspase-3/7 activity, indicating a non-apoptotic killing mechanism like necrosis shown by a strong PI-uptake by the peptide (FIG. 8-11).

Additionally, apoptotic like blebbing of the cell membrane is observed during incubation of the rhabdomyosarcoma cell line TE671 in the presence of the peptide.

TABLE 8

Correlation of activity exhibited by peptides PEP-322 and R-DIM-P-PEP-322 in model and in vitro studies.

| Peptide | PEP-322 | R-DIM-P-PEP-322 |
|---|---|---|
| amino acid sequence | PFWRIRIRR-(NH$_2$) | -PRRIRIRWFP-NH$_2$ |
| net charge | +5 | +9 |
| | cancer mimic/healthy mimic | |
| bilayer perturbation-Differential Scanning Calorimetry | +/− | +++/− |
| permeability-ANTS/DPX leakage | +/− | +++/− |
| bilayer affinity-quenching | ++/− | ++/− |
| structure-CD | > β-sheet/as in solution | > β-sheet/as in solution |
| | cancer cells/healthy cells | |
| toxicity-PI uptake, MTT | −/− | +++/− |
| cancer specificity | (+) | ++++ |

TABLE 9

Correlation of activity exhibited by selective peptide R-DIM-P-PEP-322 and non-selective peptide DIM-PEP-318 in model and in vitro studies.

| Peptide | R-DIM-P-PEP-322 | DIM-PEP-318 |
|---|---|---|
| amino acid sequence | PFWRIRIRR-P-RRIRIRWFP-NH$_2$ | FWQRRIRRWRR-FWQRRIRRWRR-NH$_2$ |
| net charge | +9 | +13 |
| | cancer mimic/healthy mimic | |
| bilayer perturbation-Differential Scanning Calorimetry | +++/− | +++/+++ |
| permeability-leakage | +++/− | +++/+ |
| bilayer affinity-quenching | ++/− | ++/+ |
| structure-CD | > β-sheets/as in solution | > α-helical/> α-helical |
| | cancer cells/healthy cells | |
| toxicity-PI uptake, MTT | +++/− | +++/+++ |
| cancer specificity | ++++ | −−− |

Discussion

In this example the selective antitumor activity of the peptides of the present invention could be demonstrated. The peptide moieties (containing no disulfide bridge) derived of the membrane active part of hLFcin such as PEP-322 and hLFcin (37-61) (one disulfide bridge) itself exhibited only weak activity against melanoma cancer cell lines, the combination of peptide moieties in R-DIM-P-PEP-322 (comprising 2 beta-strands separated by a turn) showed highly increased activity. PI-uptake of melanoma cells upon incubation with peptide R-DIM-P-PEP-322 further demonstrates that the peptide operates via a membrane mediated way, since PI can only be taken up by cells that suffer membrane disintegration. Improved interaction of the isolated peptide with the cancer mimic PS correlated with increased activity against the melanoma cancer cell line and non-interaction with the healthy mimic PC correlated with non-toxicity against non-cancer melanocytes. The isolated peptide exhibits a high membrane destabilization emphasized by highly increased membrane permeability of PS bilayers. Besides, permeability studies show that a certain threshold concentration of the isolated peptide is needed for induction of sufficient leakage of ANTS/DPX, differentiating it from highly lytic but mostly unspecific peptides like melittin. In agreement also the effect on neutral lipids is negligible. Moreover by calorimetric studies it could be demonstrated that the effect of the isolated peptide is even much higher than that of the peptide moiety at doubled concentration, rather suggesting a structural effect than a simple mass and charge effect.

Trp localization studies of peptides showed that if a peptide is active against a certain membrane, it exhibits a significant blue shift of Trp emission wavelength upon interaction with the membrane indicating a more hydrophobic environment of Trp due to interaction with the membrane interface. In the case of the peptide moiety PEP-322 and combination of peptide moieties R-DIM-P-PEP-322 the blue shift is only detected in presence of the target lipid PS present on the surface of cancer membranes, whereas in the presence of PC no blue shift appears, going hand-in-hand with a selective toxicity against cancer cells in vitro. These findings are in line with the ability of Trp quenching, which is strongly decreased only in the presence of the target lipid PS. Non-selective peptides like DIM-PEP-318 however reveal a blue shift in the presence of both model systems.

Further structural information on the studied peptides was given by CD experiments. Again structural changes for PEP-322 and the isolated peptide appear only in the presence of the negatively charged cancer mimic (SDS). The peptide DIM-PEP-318 changes its structure in environment of both models conform to its low specificity. Only the non-selective peptide shows an increase of the α-helical content in the presence of both model systems, differently PEP-322 and R-DIM-P-PEP-322 show an increase of the β-sheet content upon presence of the cancer model SDS.

From the differences in activity displayed by the peptide moiety and the combination thereof in the isolated peptide it was however surprising that both peptides show quite similar structural characteristics in solution and model system. Considering the shortness of the moiety PEP-322, it is even questionable if a β-sheet conformation is possible. It is moreover reasonable that two moiety peptide stretches arrange on the lipid surface like a dimer, but not covalently linked. The combined moieties in the isolated peptide however are fixed in this conformation via peptide bond and will create stronger membrane perturbance and finally higher membrane permeabilization, which can explain its highly increased activity in model and cell system.

On the one hand it was demonstrated that high membrane interaction of the isolated peptides derived from the membrane active peptide PEP with anionic PS correlates with high activity against melanoma cells, on the other hand it could be shown that increasing interaction with the healthy mimic neutral PC correlates with decreased specificity indicated by increased interaction with non-cancer cell types like melanocytes or fibroblasts. This was demonstrated for the combination of two peptide moieties PEP-318, namely DIM-PEP-318 also originally derived from PEP. The short peptide moieties PEP-322 and PEP-318 are only minor active against cancer cells even if incubation time is extended to 8 h or higher peptide concentrations are used. Partially the low activity can also be due to less defined structure. In contrast, the combination of these peptide moieties in DIM-PEP-322 and DIM-PEP-318 exhibit increased anticancer activity. However the different peptides seem to operate by different mechanisms, since peptide DIM-PEP-318 reaches its maximum toxicity against cancer cells already after 15 minutes, whereas contrariwise R-DIM-PEP-322 kills much slower reaching its maximum activity not before 8 hours. Nevertheless it shows similar or even increased cancer toxicity compared to DIM-PEP-318, after long time period. The different time dependence of cell killing by the peptides indicates 2 different killing mechanism. The very fast action of DIM-PEP-318 gives strong evidence for a direct membranolytic effect causing necrosis. Prediction of the secondary structure of the peptides proposes an amphiphatic α-helix. Structural analysis through CD spectroscopy of DIM-PEP-318 also reveals induction of a mostly α-helical structure in the presence of the cancer as well as the non-cancer mimic resulting in non-selective lysis of cells. The selective peptide R-DIM-P-PEP-322 obviously acts via a different mechanism. The relatively slow action together with the observation of membrane blebbing and Caspase-3/7 activity is an indication for membrane-mediated apoptosis. For induction of apoptosis the peptide has to enter the cell specifically over probably the PS compartments on the surface and further reach another negatively charged target on the surface of cancer cell mitochondria, like cardiolipin. Successive swelling of mitochondria and release of cytochrome-C activate the caspase dependent pathway of the programmed cell death. Interestingly R-DIM-P-PEP-322 shows induction of an increase in the predominant β-sheet structure with a turn and no changes in structure in the presence of the non-cancer cell mimic. In the secondary structure prediction an arrangement of 2 β-strands with hydrophobic endings with a loop in the middle composed of cationic amino acids was predicted. According to other prediction studies the amphipathic distribution of amino acids with a loop between 2 β-strands or 2 α-helices seem to be important structural features for an active and specific peptide.

The invention claimed is:

1. A method of treating cancer comprising administering an isolated peptide selected from the group consisting of PFWRIRIRRXRRIRIRWFP (SEQ ID NO: 128), PWRIRIRRXRRIRIRWP (SEQ ID No. 184), RWKRINRQWFFWQRNIRKWR (SEQ ID No. 106), PFWRIRIRRPFWRIRIRR (SEQ ID No. 125), PFFWRIRIRRPFFWRIRIRR (SEQ ID No. 141), and PFWRIRIRRRRIRIRWFP (SEQ ID No. 127), wherein "X" is proline (Pro) or glycine(Gly)$_{1-3}$, wherein the cancer is melanoma, glioblastoma, or rhabdomyosarcoma.

2. The method of claim 1, wherein the peptide is SEQ ID No. 128, SEQ ID No. 184, or SEQ ID No. 106.

* * * * *

UNITED STATES PATENT AND TRADEMARK OFFICE
CERTIFICATE OF CORRECTION

PATENT NO. : 9,492,497 B2
APPLICATION NO. : 14/760445
DATED : November 15, 2016
INVENTOR(S) : Dagmar Zweytick, Karl Lohner and Sabrina Riedl It is certified that error appears in the above-identified patent and that said Letters Patent is hereby corrected as shown below:

On the Title Page

Item (71) Applicant:
Delete "ÖSTERREICHISCHE AKADEMIE DER WISSENSCHAFTEN" and replace with
-- NEWFIELD THERAPEUTICS CORPORATION --.

In the Specification

Column 17, Line 37:
Delete "(●)" and replace with -- (D) --.

Signed and Sealed this
Fourth Day of April, 2017

Michelle K. Lee
*Director of the United States Patent and Trademark Office*